US008188056B2

(12) United States Patent  (10) Patent No.: US 8,188,056 B2
Draghia-Akli et al.  (45) Date of Patent: May 29, 2012

(54) REDUCING ARTHRITIS AND LAMENESS IN SUBJECTS BY GROWTH HORMONE RELEASING HORMONE (GHRH) SUPPLEMENTATION

(75) Inventors: Ruxandra Draghia-Akli, Houston, TX (US); Patricia A. Brown, Conroe, TX (US); David Hood, College Station, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 589 days.

(21) Appl. No.: 11/015,935

(22) Filed: Dec. 17, 2004

(65) Prior Publication Data

US 2005/0182014 A1  Aug. 18, 2005

Related U.S. Application Data

(60) Provisional application No. 60/533,756, filed on Dec. 31, 2003.

(51) Int. Cl.
*C61K 48/00* (2006.01)
*A61P 19/08* (2006.01)
*A61K 38/00* (2006.01)
*A61K 38/24* (2006.01)
*C12N 15/87* (2006.01)

(52) U.S. Cl. .................... 514/44 R; 514/11.2; 514/16.7; 514/44; 424/93.1; 435/320.1; 435/461; 530/399

(58) Field of Classification Search .................. None
See application file for complete search history.

(56) References Cited

U.S. PATENT DOCUMENTS

| | | |
|---|---|---|
| 4,223,019 A | 9/1980 | Momany et al. |
| 4,223,020 A | 9/1980 | Momany et al. |
| 4,223,021 A | 9/1980 | Momany et al. |
| 4,224,316 A | 9/1980 | Momany et al. |
| 4,226,857 A | 10/1980 | Momany et al. |
| 4,228,156 A | 10/1980 | Momany et al. |
| 4,228,158 A | 10/1980 | Momany et al. |
| 4,410,512 A | 10/1983 | Bowers et al. |
| 4,833,166 A | 5/1989 | Grosvenor et al. |
| 4,839,344 A | 6/1989 | Bowers et al. |
| 5,023,322 A | 6/1991 | Kovacs et al. |
| 5,036,045 A | 7/1991 | Thorner |
| RE33,699 E | 9/1991 | Drengler |

(Continued)

FOREIGN PATENT DOCUMENTS

WO  WO/95/19805  7/1995

(Continued)

OTHER PUBLICATIONS

Goncalves et al, Bioessays, 2005, 27: 506-517.*

(Continued)

*Primary Examiner* — Robert M Kelly
*Assistant Examiner* — Kelaginamane T Hiriyanna
(74) *Attorney, Agent, or Firm* — Thomas Kim

(57) ABSTRACT

One aspect of the current invention is a method of preventing and/or treating arthritis and/or preventing or treating lameness in a subject. Additionally, subject quality of life and welfare, and body condition scores are improved by utilizing methodology that administers the nucleic acid expression construct encoding a GHRH or functional biological equivalent to a subject through a parenteral route of administration. Following a single dose of nucleic acid expression vector, subjects are healthier and effects are demonstrated long term without additional administration(s) of the expression construct.

3 Claims, 16 Drawing Sheets

U.S. PATENT DOCUMENTS

| | | | |
|---|---|---|---|
| 5,061,690 | A | 10/1991 | Kann et al. |
| 5,084,442 | A | 1/1992 | Felix et al. |
| 5,134,120 | A | 7/1992 | Boyd et al. |
| 5,137,872 | A | 8/1992 | Seely et al. |
| 5,292,721 | A | 3/1994 | Boyd et al. |
| 5,439,440 | A | 8/1995 | Hofmann et al. |
| 5,486,505 | A | 1/1996 | Bowers et al. |
| 5,696,089 | A | 12/1997 | Felix et al. |
| 5,702,359 | A | 12/1997 | Hofmann et al. |
| 5,756,264 | A | 5/1998 | Schwartz et al. |
| 5,776,901 | A | 7/1998 | Bowers et al. |
| 5,792,747 | A | 8/1998 | Schally et al. |
| 5,846,936 | A | 12/1998 | Felix et al. |
| 5,847,066 | A | 12/1998 | Coy et al. |
| 6,423,693 | B1 | 7/2002 | Schwartz et al. |
| 6,551,996 | B1 | 4/2003 | Schwartz et al. |
| 2003/0055017 | A1 | 3/2003 | Schwartz et al. |

FOREIGN PATENT DOCUMENTS

| | | |
|---|---|---|
| WO | WO/96/12006 | 4/1996 |
| WO | WO/96/12520 | 5/1996 |
| WO | WO/97/07826 | 3/1997 |

OTHER PUBLICATIONS

Draghia-Akli, et al., 1999, Nat. Biotech.,17:1179-83.*
Nicol et al., 2002, Gene therapy 9:1351-8.*
Bechtold et al., 2001, J. Endocrinol. Metabol. 86:5737-5744.*
U.S. Appl. No. 10/657,725, filed Sep. 8, 2003, Smith, et al.
Acsadi, G., G. Dickson, D. R. Love, A. Jani, F. S. Walsh, A. Gurusinghe, Wolff, JA, and K. E. Davies. 1991. Human dystrophin expression in mdx mice after intramuscular injection of DNA constructs. Nature 352:815-818.
Aihara, H. and J. Miyazaki. 1998. Gene transfer into muscle by electroporation in vivo. Nat. Biotechnol. 16:867-870.
Almendro, N., T. Belton, C. Rius, P. Lastres, C. Lange, A. Corbi, and C. Bernabeu. 1996. Cloning of the human platelet endothelial cell adhesion molecule-1 promoter and its tissue-specific expression. Structural and functional characterization. J. Immunol. 157:5411-5421.
Aratani, Y., R. Okazaki, and H. Koyama. 1992. End extension repair of introduced targeting vectors mediated by homologous recombination in mammalian cells. Nucl. Acids Res. 20:4795-4801.
Argente, J., J. Pozo, and J. A. Chowen. 1996. The growth hormone axis: control and effects. Hormone Research 45 Suppl 1:9-11.
Babiuk, L. A., R. Pontarollo, S. Babiuk, B. Loehr, and van Drunen Littel-van den Hurk. 2003. Induction of immune responses by DNA vaccines in large animals. Vaccine 21:649-658.
Barr, E. and J. M. Leiden. 1991. Systemic delivery of recombinant proteins by genetically modified myoblasts. Science 254:1507-1509.
Bercu, B. B. and R. F. Walker. 1997. Growth Hormone Secretagogues in Children With Altered Growth. Acta Paediatrica 86:102-106.
Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.
Blethen, S. L. and A. C. Rundle. 1996. Slipped capital femoral epiphysis in children treated with growth hormone. A summary of the National Cooperative Growth Study experience. Horm. Res. 46:113-116.
Bohlen, P., F. Esch, P. Brazeau, N. Ling, and R. Guillemin. 1983. Isolation and characterization of the porcine hypothalamic growth hormone releasing factor. Biochem. Biophys. Res. Commun. 116:726-734.
Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.
Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Caroni, P. and C. Schneider. 1994. Signaling by insulin-like growth factors in paralyzed skeletal muscle: rapid induction of IGF1 expression in muscle fibers and prevention of interstitial cell proliferation by IGF-BP5 and IGF-BP4. J. Neurosci. 14:3378-3388.
Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U. S. A 94:3596-3601.
Chevalier, R. L., S. Goyal, A. Kim, A. Y. Chang, D. Landau, and D. LeRoith. 2000. Renal tubulointerstitial injury from ureteral obstruction in the neonatal rat is attenuated by IGF-1. Kidney Int. 57:882-890.
Chung, C. S., T. D. Etherton, and J. P. Wiggins. 1985. Stimulation of swine growth by porcine growth hormone. J. Anim Sci. 60:118-130.
Cocea, L 1997. Duplication of a region in the multiple cloning site of a plasmid vector to enhance cloning-mediated addition of restriction sites to a DNA fragment. Biotechniques 23:814-816.
Corpas, E., S. M. Harman, M. A. Pineyro, R. Roberson, and M. R. Blackman. 1993. Continuous subcutaneous Infusions of growth hormone (GH) releasing hormone 1-44 for 14 days increase GH and insulin-like growth factor-I levels in old men. J. Clin. Endocilnol. Metab.76:134-138.
Dahler, A., R. P. Wade, G. E. Muscat, and M. J. Waters. 1994. Expression vectors encoding human growth hormone (hGH) controlled by human muscle-specific promoters: prospects for regulated production of hGH delivered by myoblast transfer or Intravenous injection. Gene 145:305-310.
Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.
Danko, I. and J. A. Wolff. 1994. Direct gene transfer into muscle. Vaccine 12:1499-1502.
Darquet, A. M., B. Cameron, P. Wils, D. Scherman, and J. Crouzet. 1997. A new DNA vehicle for nonviral gene delivery: supercoiled minicircle. Gene Ther. 4:1341-1349.
Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.
Davis, H. L., R. G. Whalen, and B. A. Demeneix. 1993. Direct gene transfer into skeletal muscle in vivo: factors affecting efficiency of transfer and stability of expression. Hum. Gene Ther. 4:151-159.
Dhawan, J., L. C. Pan, G. K. Paviath, M. A. Travis, A. M. Lanctot, and H. M. Blau. 1991, Systemic delivery of human growth hormone by injection of genetically engineered myobiasts. Science 254:1509-1512.
Dialynas, E., H. Brown-Borg, and A. Bartke. 1999. Immune function in transgenic mice overexpressing growth hormone (GH) releasing hormone, GH or GH antagonist. Proc. Soc. Exp. Biol. Med. 221:178-183.
Dolnik, V., M. Novotny, and J. Chmelik. 1993. Electromigration behavior of poly-(L-glutamate) conformers in concentrated polyacrylamide gels. Biopolymers 33:1299-1306.
Dorsch-Hasler, K., G. M. Keil. F. Weber, M. Jasin, W. Schaffner, and U. H. Koszlnowski. 1985. A long and complex enhancer activates transcription of the gene coding for the highly abundant immediate early mRNA in murine cytomegalovirus. Proc.Natl.Acad.Sci.U.S.A 82:8325-8329.
Draghia-Akli, R., K. M. Ellis, L. A. Hill, P. B. Malone, and M. L. Florotto. 2003. High-efficiency growth hormone releasing hormone plasmid vector administration into skeletal muscle mediated by electroporation in pigs. FASEB J 17:528-528.
Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.
Draghia-Akli. R., K. A. Hahn, G. K. King, K. Cummings, and R. H. Carpenter. 2002a. Effects of Plasmid Mediated Growth Hormone Releasing Hormone in Severely Debilitated Dogs With Cancer. Mol. Ther. 8:830-838.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technol. Cancer Res. Treat. 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Draghia-Akli, R. and L. C. Smith. 2003. Electrokinetic Enhancement of Plasmid Delivery in Vivo. In: N. S. Templeton and D. D. Lasic (Eds.) Gene Therapy—Therapeutic Mechanisms and Strategies. pp. 245-263. Marcel Dekker, Inc., New York.

Dubreuil, P., D. Petitclerc, G. Pelletier, P. Gaudreau, C. Farmer, Mowles, TF, and P. Brazeau. 1990. Effect of dose and frequency of administration of a potent analog of human growth hormone-releasing factor on hormone secretion and growth in pigs. J. Anim Sci. 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. J. Clin. Endocrinol. Metab. 75:1115-1120.

Erikstrup, C., L. M. Pedersen, L. Heickendorff, T. Ledet, and L. M. Rasmussen. 2001. Production of hyaluronan and chondroitin sulphate proteoglycans from human arterial smooth muscle—the effect of glucose, Insulin, IGF-I or growth hormone. Eur. J Endocrinol. 145:193-198.

Esch, F. S., P. Bohlen, N. C. Ling, P. E. Brazeau, W. B. Wehrenberg, M. O. Thomer, M. J. Cronin, and R. Guillemin. 1982. Characterization of a 40 residue peptide from a human pancreatic tumor with growth hormone releasing activity. Biochem. Biophys. Res. Commun. 109:152-158.

Etherton, T. D., J. P. Wiggins, C. S. Chung, C. M. Evock, J. F. Rebhun, and P. E. Walton. 1986. Stimulation of pig growth performance by porcine growth hormone and growth hormone-releasing factor. J. Anim Sci. 63:1389-1399.

Evans, W. S., M. L. Vance, D. L Kaiser, R. P. Sellers, J. L. Borges, T. R. Downs, L. A. Frohman, J. Rivier, W. Vale, and M. O. Thorner. 1985. Effects of intravenous, subcutaneous, and intranasal administration of growth hormone (GH)-releasing hormone-40 on serum GH concentrations in normal men. J. Clin. Endocrinol. Metab. 61:848-850.

Farmer, C., D. Petitclerc, G. Pelletier, and P. Brazeau. 1992. Lactation performance of sows injected with growth hormone-releasing factor during gestation and(or) lactation. J. Anim Sci. 70:2636-2642.

Farmer, C., S. Robert, and J. J. Matte. 1996. Lactation performance of sows fed a bulky diet during gestation and receiving growth hormone-releasing factor during lactation. J. Anim Sci. 74:1298-1306.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Frisbie, D. D., S. C. Ghivizzani, P. D. Robbins, C. H. Evans, and C. W. McIlwraith. 2002. Treatment of experimental equine osteoarthritis by in vivo delivery of the equine interleukin-1 receptor antagonist gene. Gene Ther. 9:12-20.

Frisbie, D. D. and C. W. McIlwraith. 2000. Evaluation of gene therapy as a treatment for equine traumatic arthritis and osteoarthritis. Clin. Orthop.S273-S287.

Frohman, L. A., T. R. Downs, E. P. Helmer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., J. L. Thominet, C. B. Webb, M. L. Vance, H. Uderman, J. Rivier, W. Vale, and M. O. Thomer. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Fubini, S. L., H. N. Erb, K. P. Freeman, and R. J. Todhunter. 1999. Prognostic factors affecting survival of 507 horses with joint disease: (1983 to 1990). Can. J Vet. Res. 63:253-260.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and . 1995. The insulin gene promoter. A simplified nomenclature. Diabetes 44:1002-1004.

Gopinath, R. and T. D. Etherton. 1989a. Effects of porcine growth hormone on glucose metabolism of pigs: I. Acute and chronic effects on plasma glucose and insulin status. J. Anim. Sci. 67:682-688.

Gopinath, R. and T. D. Etherton. 1989b. Effects of porcine growth hormone on glucose metabolism of pigs: II. Glucose tolerance, peripheral tissue insulin sensitivity and glucose kinetics. J. Anim Sd. 67:689-697.

Gouze, E., S. C. Ghivizzani, G. D. Palmer, J. N. Gouze, P. D. Robbins, and C. H. Evans. 2001. Gene therapy for rheumatoid arthritis. Expert. Opin. Biol. Ther. 1:971-978.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Horlick, R. A. and P. A. Benfield. 1989. The upstream muscle-specific enhancer of the rat muscle creatine kinase gene is composed of multiple elements. Mol. Cell. Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jardieu, P., R. Clark, D. Mortensen, and K. Dorshkind. 1994. In vivo administration of insulin-like growth factor-I stimulates primary B lymphopoiesis and enhances lymphocyte recovery after bone marrow transplantation. J Immunol. 152:4320-4327.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makin, S. Orita, A. Nakata, and T. Kakunaga. 1989. DNA bending and binding factors of the human beta-actin promoter. Nucleic Acids Res. 17:523-537.

Khorram, O., M. Garthwaite, and T. Golos. 2001. The influence of aging and sex hormones on expression of growth hormone-releasing hormone in the human immune system. J Clin. Endocrinol. Metab 86:3157-3161.

Klamut, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10:193-205.

Klindt, J., J. T. Yen, F. C. Buonomo, A. J. Roberts, and T. Wise. 1998. Growth, body composition, and endocrine responses to chronic administration of insulin-like growth factor I and(or) porcine growth hormone in pigs. J. Anim Sci. 76:2368-2381.

Koo, G. C., C. Huang, R. Camacho, C. Trainor, J. T. Blake, A. Sirotina-Meisher, K. D. Schleim, T. J. Wu, K. Cheng, R. Nargund, and G. McKissick. 2001. Immune enhancing effect of a growth hormone secretagogue. J Immunol. 166:4195-4201.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lapierre, H., G. Pelletier, D. Petitclerc, P. Dubreuil, J. Morisset, P. Gaudreau, Y. Couture, and P. Brazeau. 1991. Effect of human growth hormone-releasing factor and(or) thyrotropin-releasing factor on growth, carcass composition, diet digestibility, nutrient balance, and plasma constituents in dairy calves. J. Anim. Sci. 69:587-598.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Ledwith, B. J., S. Manam, P. J. Trollo, A. B. Barnum, C. J. Pauley, T. G. Griffiths, L. B. Harper, C. M. Beare, W. J. Bagdon, and W. W. Nichols. 2000a. Plasmid DNA vaccines: investigation of integration into host cellular DNA following intramuscular injection in mice. Intervirology 43:258-272.

Ledwith, B. J., S. Menem, P. J. Troll, A. B. Barnum, C. J. Pauley, T. G. Griffiths, L. B. Harper, H. B. Schock, H. Zhang, J. E. Faris, P. A. Way, C. M. Beare, W. J. Bagdon, and W. W. Nichols. 2000b. Plasmid DNA vaccines: assay for integration into host genomic DNA. Dev. Biol. (Basel) 104:33-43.:33-43.

Lee, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase. L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Miles, C. Chamsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, J. L. and D. LeRoith. 1999. Insulin-like growth factor I is essential for postnatal growth in response to growth hormone. Endocrinology 140:5178-5184.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lucas, M. L, Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macejak, D. G. and P. Sarnow. 1991. Internal initiation of translation mediated by the 5' leader of a cellular mRNA. Nature 353:90-94.

Malone, E. D. 2002. Managing chronic arthritis. Vet. Clin. North Am. Equine Pract. 18:411-437.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A, I. Tooyama, S. Isobe, Y. Oomura, I. Akiguchi, K. Hanel, J. Kimura, and H. Kimura. 1994. Immunohistochemical localization in the rat brain of an epitope corresponding to the fibroblast growth factor receptor-1. Neuroscience 60:49-66.

Mcnally, M. A., J. S. Lebkowsid, T. B. Okarma, and L. B. Lerch. 1988. Optimizing electroporation parameters for a variety of human hematopoletic cell lines. Biotechniques 6:882-886.

Mi, Z., S. C. Ghivizzani, E. R. Lechman, D. Jaffurs, J. C. Glorioso, C. H. Evans, and P. D. Robbins. 2000. Adenovirus-mediated gene transfer of insulin-like growth factor 1 stimulates proteoglycan synthesis in rabbit joints. Arthritis Rheum. 43:2563-2570.

Miklavcic, D., K. Berays, D. Semrov, M. Cemazar, F. Demsar, and G. Sersa. 1998. The importance of electric field distribution for effective in vivo electroporation of tissues. Biophys. J 74:2152-2158.

Miller, K. F., D. J. Bolt, V. G. Pursel, R. E. Hammer, C. A. Pinkert, R. D. Palmiter, and R. L. Brinster. 1989. Expression of human or bovine growth hormone gene with a mouse metallothionein-1 promoter in transgenic swine alters the secretion of porcine growth hormone and insulin-like growth factor-I. J. Endocrinol. 120:481-488.

Moore, R. A. 2002. The hidden costs of arthritis treatment and the cost of new therapy—the burden of non-steroidal anti-Inflammatory drug gastropathy. Rheumatology. (Oxford) 41 Supp 1:7-15; discussion 35-42.

Mukherjee, P., B. Wu, L. Mayton, S. H. Kim, P. D. Robbins, and P. H. Wooley. 2003. TNF receptor gene therapy results in suppression of IgG2a anticollagen antibody in collagen induced arthritis. Ann. Rheum. Dis. 62:707-714.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Murray, R. C., R. M. DeBowes, E. M. Gaughan, C. F. Zhu, and K. A. Athanasiou. 1998. The effects of intra-articular methylprednisolone and exercise on the mechanical properties of articular cartilage in the horse. Osteoarthritis. Cartilage. 6:106-114.

Murray, R. D. and S. M. Shalet. 2000. Growth hormone: current and future therapeutic applications. Expert. Opin. Pharmacother. 1:975-990.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhnnann, H. Liang, M. Oakley, A. Taye, B. K. Sim, and S. L. Hoffman. 2001. Codon optimization of gene fragments encoding Plasmodium falciparum merzoite proteins enhances DNA vaccine protein expression and immunogenicity in mice. Infect. Immun. 69:7250-7253.

Naughton, M. J. and S. A. Shumaker. 2003. The case for domains of function in quality of life assessment. Qual. Life Res. 12 Suppl 1:73-80.:73-80.

Neidel, J. 2001. Changes in systemic levels of insulin-like growth factors and their binding proteins in patients with rheumatoid arthritis. Clin. Exp. Rheumatol. 19:81-84.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pavasant, P., T. Shizari, and C. B. Underhill. 1996. Hyaluronan synthesis by epiphysial chondrocytes is regulated by growth hormone, Insulin-like growth factor-1, parathyroid hormone and transforming growth factor-beta 1. Matrix Biol. 15:423-432.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:288-276.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U. S. A 81:7161-7165.

Prentice, H., R. A. Kioner, T. Prigozy, T. Christensen, L. Newman, Y. Li, and L. Kedes. 1994. Tissue restricted gene expression assayed by direct DNA injection into cardiac and skeletal muscle. J. Mol. Cell. Cardiology 26:1393-1401.

Pursel, V. G., D. J. Bolt, K. F. Miller, C. A. Pinkert, R. E. Hammer, R. D. Palmiter, and R. L. Brinster. 1990. Expression and performance in transgenic pigs. J. Reprod. Fertil. Suppl 40:235-45:235-245.

Rabinovsky, E. O., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Reginster, J. Y. 2002. The prevalence and burden of arthritis. Rheumatology. (Oxford) 41 Supp 1:3-6.:3-6.

Robbins, K., S. McCabe, T. Scheiner, J. Strasser, R. Clark, and P. Jardieu. 1994. Immunological effects of insulin-like growth factor-I—enhancement of immunoglobulin synthesis. Clin. Exp. Immunol. 95:337-342.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10:187-192.

Skroch, P., C. Buchman, and M. Karin. 1993. Regulation of human and yeast metallothionein gene transcription by heavy metal ions. Prog. Clin. Biol. Res. 380:113-28.113-128.

Smith, L. C. and J. L. Nordstrom. 2000. Advances in plasmid gene delivery and expression in skeletal muscle. Cliff. Opin. Mol. Ther. 2:150-154.

Smith, V. G., A. D. Leman, W. J. Seaman, and F. VanRavenswaay. 1991. Pig weaning weight and changes in hematology and blood chemistry of sows injected with recombinant porcine somatotropin during lactation. J. Anim Sci. 69:3501-3510.

Soubrier, F., B. Cameron, B. Manse. S. Somarriba, C. Dubertret, G. Jaslin, G. Jung, C. L. Caer, D. Deng, J. M. Mouvault, D. Scherman, J. F. Mayaux, and J. Crouzet. 1999. pCOR: a new design of plasmid vectors for nonviral gene therapy. Gene Ther. 8:1482-1488.

Steel, C. M., A. R. Hunt, P. L. Adams, I. D. Robertson, C. Chicken, J. V. Yovich, and J. A. Stick. 1999. Factors associated with prognosis for survival and athletic use in foals with septic arthritis: 93 cases (1987-1994). J Am. Vet Med. Assoc. 215:973-977.

Terada, V., H. Tanaka, T. Okado, S. Inoshita, M. Kuwahara, T. Akiba, S. Sasaki, and F. Marumo. 2001. Efficient and ligand-dependent regulated erythropoletin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. J. Clin. Endocrinol. Metab. 59:846-849.

Thorner, M. O., M. L. Hartman, M. L. Vance, S. S. Pezzoli, and E. J. Ampleford. 1995. Neuroendocrine regulation of growth hormone secretion. Neurosci. Biobehay. Reviews 19:465-468.

Thomer, M. O., M. L. Vance, W. S. Evans, A. D. Rogol, J. Rivier, W. Vale, Blizzard, and RM. 1986. Clinical studies with GHRH in man. Hormone Research 24:91-98.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA injection in combination with electroporation: a novel method for vaccination of farmed ruminants. Scand. J Immunol. 57:229-238.

Toneguzzo, F., A. Keating, S. Glynn, and K. McDonald. 1988. Electric field-mediated gene transfer characterization of DNA transfer and patterns of integration in lymphoid cells. Nucleic Acids Res. 16:5515.5532.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss. and M. Yaniv 1989. The rat albumin promoter: cooperation with upstream elements is required when binding of APF/HNF1 to the proximal element is partially Impaired by mutation or bacterial methylation. Mol. Cell Biol. 9:4759-4766.

Tronche, F., A. Rollier, P. Herbomel, I. Bach, S. Cereghlni, M. Weiss, and M. Yaniv. 1990. Anatomy of the rat albumin promoter. Mol. Blot. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2(XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, and J. M. Isner. 1998. Direct Intramuscular gene transfer of naked DNA encoding vascular endothelial growth factor augments collateral development and tissue perfusion. Circulation 94:3281-3290.

Tur-Kaspa, R., L. Telcher, B. J. Levine, A. I. Skoultchi, and D. A. Shafritz. 1986. Use of electroporation to introduce biologically active foreign genes into primary rat hepatocytes. Mol. Cell Biol. 6:716-718.

Van Rooij, E. M., B. L. Haagmans, H. L. Glansbeek, Y. E. de Visser, M. G. de Bruin, W. Boersma, and A. T. Bianchi. 2000. A DNA vaccine coding for glycoprotein B of pseudorabies virus Induces cell-mediated Immunity in pigs and reduces virus excretion early after infection. Vet. Immunol. Immunopathol. 74:121-136.

Vance, M. L. 1990. Growth-hormone-releasing hormone. Clinical Chemistry 36:415-420.

Vance, M. L., D. L. Kaiser, W. S. Evans, R. Furlanetto, W. Vale, J. Rivier, and M. O. Thomer. 1985. Pulsatile growth hormone secretion in normal man during a continuous 24-hour infusion of human growth hormone releasing factor (1-40). Evidence for intermittent somatostatin secretion. J. Clin. Invest 75:1584-1590.

Veldhuis, J. D., A. Iranmanesh, and A. Weltman. 1997. Elements in the Pathophysiology of Diminished Growth Hormone (GH) Secretion in Aging Humans. Endocrine 7:41-48.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stavenaert, and A. Beckers. 1997. Two years of replacement therapy in adults with growth hormone deficiency. Clin. Endocrinol. (Oxf) 47:485-494.

Vilquin, J. T., P. F. Kennel, M. Patumeau-Jouas, P. Chapdelaine, N. Bolssel, P. Delaere, J. P. Tremblay, D. Schennan, M. Y. Fiszman, and K. Schwartz. 2001. Electrotransfer of naked DNA in the skeletal muscles of animal models of muscular dystrophies. Gene Thar. 8:1097-1107.

Vittone, J., M. R. Blackman, J. Busby-Whitehead, C. Tslao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wolff, J. A., R. W. Malone, P. Williams, W. Chong, G. Acsadi, A. Jani, Feigner, and PL. 1990. Direct gene transfer into mouse muscle in vivo. Science 247:1465-1468.

Wu, H. K., J. A. Squire, Q. Song, and R. Weksberg. 1997. Promoter-dependent tissue-spectfic expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Blophys. J. 65:1684-1689.

Yasui, A., K. Oda, H. Usunomiya, K Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

PCT Invitation to Pay Additional Fees, dated Jul. 6, 2005.

PCT International Search Report and Written Opinion Dated Jul. 20, 2005.

Draghia-Akli R, Ellis KM, Hill LA, Malone PB, Florotto ML. "High-Efficiency Growth Hormone-Releasing Hormone Plasmid Vector Administration into Skeletal Muscle Mediated by Electroporation in Pigs." FASEB J. Mar. 17, 2003(3):526-8. Epub Jan. 2, 2003.

Draghia-Akli R, Hahn KA, King GK, Cummings KK, Carpenter RH. "Effects of Plasmid-Mediated Growth Hormone-Releasing Hormone in Severely Debilitated Dogs with Cancer." Mol Ther. Dec. 6, 2002(6):830-6.

* cited by examiner

```
Translation of GHRH species (SHORT):

bovine GHRH  (1) YADAIFTNSYRKVLGQLSARKLLQDIMNRQQGERNQEQGA
        ovine GHRH  (1) YADAIFTNSYRKILGQLSARKLLQDIMNRQQGERNQEQGA
          cat GHRH  (1) YADAIFTNSYRKVLGQLSARKLLQDIMSRQQGERNQEQGA
      chicken GHRH  (1) HADGIFSKAYRKLLGQLSARNYLHSLMAKRVGSGLGDEAEPLS
horse GHRH (partial)(1) -ADAIFTNNYRKVLGQLSARKILQDIMSR----------
           HV-GHRH  (1) HVDAIFTNSYRKVLAQLSARKLLQDILNRQQGERNQEQGA
           TI-GHRH  (1) YIDAIFTNSYRKVLAQLSARKLLQDILNRQQGERNQEQGA
   wt-porcine GHRH  (1) YADAIFTNSYRKVLGQLSARKLLQDIMSRQQGERNQEQGA
          dog GHRH  (1) YADAIFTNSYRKVLGQLSARKLLQDIMSRQQGERNREQGA Consensus  (1) YADAIFTNSYRKVLGQLSARKLLQDIMSRQQGERNQEQGA Translation of GHRH species (LONG):

bovine GHRH  (1) MVLWVFFLVTLTLSSGSHGSLPS-QPLRIPRYADAIFTNSYRKVLGQLSARKLLQDIMNRQQGERNQEQGA
        ovine GHRH  (1) MVLWVFFLVTLTLSSGSHGSLPS-QPLRIPRYADAIFTNSYRKILGQLSARKLLQDIMNRQQGERNQEQGA
          cat GHRH  (1) MVLWVFFLVILTLDSGSHCSPPS-LPLRMPRYADAIFTNSYRKVLGQLSARKLLQDIMSRQQGERNQEQGA---
      chicken GHRH  (1) -MALWVFFLILTTSGSHCSLPPSPPFRVRRHADGIFSKAYRKLLGQLSARNYLHSLMAKRVGSGLGDEAEPLS
horse GHRH (partial)(1) -----------------------------ADAIFTNNYRKVLGQLSARKILQDIMSR------------
           HV-GHRH  (1) MVLWVFFFVILTLSNSSHCSPPPPLTLRMRRHVDAIFTNSYRKVLAQLSARKLLQDILNRQQGERNQEQGA---
           TI-GHRH  (1) MVLWVFFFVILTLSNSSHCSPPPPLTLRMRRYIDAIFTNSYRKVLAQLSARKLLQDILNRQQGERNQEQGA---
   wt-porcine GHRH  (1) MVLWVFFFVILTLSNSSHCSPPPPLTLRMRRYADAIFTNSYRKVLGQLSARKLLQDIMSRQQGERNQEQGA---
          dog GHRH  (1) MVLWVFFLVILTLSSGSHSSPPS-LPIRIPRYADAIFTNSYRKVLGQLSARKLLQDIMSRQQGERNREQGA---

Consensus  (1) MVLWVFF VILTLSSGSHCSPP  LPLRM RYADAIFTNSYRKVLGQLSARKLLQDIMSRQQGERNQEQGA
```

Figure 16

REDUCING ARTHRITIS AND LAMENESS IN SUBJECTS BY GROWTH HORMONE RELEASING HORMONE (GHRH) SUPPLEMENTATION

RELATED APPLICATIONS

This application claims priority to U.S. Provisional Patent Application, Ser. No. 60/533,756, entitled "REDUCING ARTHRITIS AND LAMENESS IN SUBJECTS BY GROWTH HORMONE RELEASING HORMONE (GHRH) SUPPLEMENTATION," filed on Dec. 31, 2003, having Ruxandra Draghia-Akli, Patricia A. Brown, and David Hood listed as inventors, the entire content of which is hereby incorporated by reference.

BACKGROUND

This invention pertains to an isolated composition and a method of treating arthritis or lameness in a subject. More specifically, the invention pertains to specific growth hormone releasing hormone ("GHRH") compositions, and methods of use thereof. The GHRH is an isolated composition or an isolated nucleic acid molecule that encodes the GHRH or functional biological equivalent. Another aspect of the current invention includes a method for delivering the composition of this invention to a subject for treating arthritis or lameness in a subject, such as a horse or other animal having arthritis or lameness.

Arthritis: The prevalence of arthritis is high, with osteoarthritis being one of the most frequent disorders in the population. In 1997, approximately 16% of the US population had some form of arthritis. This prevalence is expected to increase in the coming years, as arthritis more often affects the elderly, a proportion of the population that is increasing. The economic burden of such musculoskeletal diseases is also high, accounting for up to 1-2.5% of the gross national product of western nations. This burden comprises both the direct costs of medical interventions and indirect costs, such as premature mortality and chronic and short-term disability. The impact of arthritis on quality-of-life indicators is of particular importance. Musculoskeletal disorders are associated with some of the poorest quality-of-life indicators, particularly in terms of bodily pain. For example, bodily pain and physical functioning due to musculoskeletal disorders have mean quality-of-life indicator scores consisting of 52.1 and 49.9, respectively (values were derived from the MOS 36-item Short Form Health Survey, wherein low scores tend to indicate a limiting physical, psychic and relational health aspects of a patient and higher scores tend to indicate non-limiting aspects). In comparison to musculoskeletal disorders, the quality-of-life scale for gastrointestinal conditions is less limiting (e.g. bodily pain 52.9 and physical functioning 55.4). Other examples include: chronic respiratory diseases (e.g. bodily pain 72.7 and physical functioning 65.4); and cardiovascular conditions (e.g. bodily pain 64.7, and physical functioning 59.3) (Reginster, 2002).

Joint disease is a significant social and economic problem that needs continued research improvements for therapeutics. Pain associated with arthritis is very common throughout the world and is an increasing problem in the ageing population (Moore, 2002). Because horses have osteoarthritis conditions that are similar to human osteoarthritis conditions, the horse can be chosen as a species to investigate gene transfer as a potential therapeutic modality for the treatment of osteoarthritis (Frisbie and McIlwraith, 2000). Many compounds are being investigated for the control of symptoms of osteoarthritis in people and animals. Ideally, treatment should include analgesia, inflammation control, and chondroprotection. Currently available treatments may include: lavage of the affected joints if septic, intra-articular administration of antibiotics, hyaluronidase (e.g. Legend®, Bayer, drug used in horses) or corticosteroids, arthroscopic debridement with or without partial synovectomy, systemic administration of antibiotics, anti-inflamatory or chondroprotective drugs (Fubini et al., 1999; Murray et al., 1998; Steel et al., 1999). With further progress in this area, combination therapies tailored to the needs of the individual animal should enable us to maximize efficacy and minimize side effects. Only a few of the newer therapies and pharmaceutical agents have been investigated in the horse as a model for human arthritis, however arthritis therapies that employ biological agents are currently limited by possible side effects such as the occurrence or reemergence of viral and bacterial infections as well as their exorbitant expense (Malone, 2002). The need for a comprehensive therapy for both the joint problems and general health and welfare of the animal is critical (Naughton and Shumaker, 2003).

Growth Hormone Releasing Hormone ("GHRH") and Growth Hormone ("GH") Axis: To better understand utilizing GHRH plasmid mediated gene supplementation as a treatment of arthritis, the mechanisms and current understanding of the GHRH/GH axis will be addressed. Although not wanting to be bound by theory, the central role of growth hormone ("GH") is controlling somatic growth in humans and other vertebrates. The physiologically relevant pathways regulating GH secretion from the pituitary are fairly well known. The GH production pathway is composed of a series of interdependent genes whose products are required for normal growth. The GH pathway genes include: (1) ligands, such as GH and insulin-like growth factor-I ("IGF-I"); (2) transcription factors such as prophet of pit 1, or prop 1, and pit 1: (3) agonists and antagonists, such as growth hormone releasing hormone ("GHRH") and somatostatin ("SS"), respectively; and (4) receptors, such as GHRH receptor ("GHRH-R") and the GH receptor ("GH-R"). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism. GH synthesis and secretion from the anterior pituitary is stimulated by GHRH and inhibited by somatostatin, both hypothalamic hormones. GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

Several studies in different animal models and human have shown that GHRH has an immune stimulatory effect, both through stimulation of the GH axis and directly as an immune-modulator (Dialynas et al., 1999; Khorram et al., 2001). GH has been known to enhance immune responses, whether directly or through the IGF-I, induced by GH. Recently, a GH secretagogue ("GHS"), was found to induce the production of GH by the pituitary gland, but also determined a statistically significant increase in thymic cellularity and differentiation in old mice. When inoculated with a transplantable lymphoma cell line, EL4, the treated old mice showed statistically significant resistance to the initiation of tumors and the subsequent metastases. Generation of CTL to EL4 cells was also enhanced in the treated mice, suggesting that GHS has a considerable immune enhancing effect (Koo et al., 2001). The immune function is also modulated by IGF-I, which has two major effects on B cell development: potentiation and maturation, and as a B-cell proliferation cofactor that works together with interlukin-7 ("IL-7"). These activities were identified through the use of anti-IGF-I antibodies, antisense sequences to IGF-I, and the use of recombinant IGF-I to substitute for the activity. There is evidence that macrophages are a rich source of IGF-I. The treatment of mice with recombinant IGF-I confirmed these observations as it increased the number of pre-B and mature B cells in bone marrow (Jardieu et al., 1994). The mature B cell remained sensitive to IGF-I as immunoglobulin production was also stimulated by IGF-I in vitro and in vivo (Robbins et al., 1994).

In aging mammals, the GHRH-GH-IGF-I axis undergoes considerable decrement having reduced GH secretion and IGF-I production associated with a loss of skeletal muscle mass (sarcopenia), osteoporosis, arthritis, increased fat deposition and decreased lean body mass (Caroni and Schneider, 1994; Veldhuis et al., 1997). It has been demonstrated that the development of these changes can be offset by recombinant GH therapy. It has also been shown in culture, in vitro that the production of hyaluronan and condroitin sulphate proteoglycans is regulated by GH, IGF-I, and that these molecules may be of significant importance in the therapy of joint pathology (Erikstrup et al., 2001; Pavasant et al., 1996). For instance, gene transfer of IGF-I into rabbit knee joints promotes proteoglycan synthesis without significantly affecting inflammation or cartilage breakdown, or adverse effects. As a result, local gene transfer of IGF-I to joints was suggested as a therapeutic strategy to stimulate new matrix synthesis in both rheumatoid arthritis and osteoarthritis (Mi et al., 2000). It has been also shown that increased levels of IGF-binding proteins in arthritis may result in the reduced availability of free IGFs that can bind to IGF receptors. The observed changes in the IGF system may thus participate in the catabolic processes in rheumatoid arthritis, and the development of cachexia and wasting in these patients (Neidel, 2001). A therapy that would address both the arthritic disease and the wasting would be a major step forward in the well-being and quality of life of patients.

The production of recombinant proteins in the last 2 decades provided a useful tool for the treatment of many diverse conditions. For example, GH has been used successfully in GH-deficiencies in short stature children, or as an anabolic agent in burn, sepsis, and AIDS patients. However, resistance to GH action has been reported in malnutrition and infection. Clinically, GH replacement therapy is used widely in both children and the elderly. Current GH therapy has several shortcomings, however, including frequent subcutaneous or intravenous injections, insulin resistance and impaired glucose tolerance (Rabinovsky et al., 1992); children are also vulnerable to premature epiphyseal closure and slippage of the capital femoral epiphysis (Liu and LeRoith, 1999). A "slow-release" form of GH (from Genentech) has been developed that only requires injections every 14 days. However, this GH product appears to perturb the normal physiological pulsatile GH profile, and is also associated with frequent side effects.

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (Esch et al., 1982; Thorner et al., 1984). Administration of recombinant GHRH to GH-deficient children or adult humans augments IGF-I levels, increases GH secretion proportionally to the GHRH dose, yet still invokes a response to bolus doses of recombinant GHRH (Bercu and Walker, 1997). Thus, GHRH administration represents a more physiological alternative of increasing subnormal GH and IGF-I levels (Corpas et al., 1993).

GH is released in a distinctive pulsatile pattern that has profound importance for its biological activity (Argente et al., 1996). Secretion of GH is stimulated by the GHRH, and inhibited by somatostatin, and both hypothalamic hormones (Thorner et al., 1995). GH pulses are a result of GHRH secretion that is associated with a diminution or withdrawal of somatostatin secretion. In addition, the pulse generator mechanism is timed by GH-negative feedback. Effective and regulated expression of the GH and IGF-I pathway is essential for optimal linear growth, homeostasis of carbohydrate, protein, and fat metabolism, and for providing a positive nitrogen balance (Murray and Shalet, 2000). Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (Dubreuil et al., 1990; Vance, 1990; Vance et al., 1985). Although recombinant GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical.

Wild-type GHRH has a relatively short half-life in the circulatory system, both in humans (Frohman et al., 1984) and in farm animals. After 60 minutes of incubation in plasma, 95% of the GHRH(1-44)NH2 is degraded, while incubation of the shorter (1-40)OH form of the hormone under similar conditions, shows only a 77% degradation of the peptide (Frohman et al., 1989). Incorporation of cDNA coding for a particular protease-resistant GHRH analog in a therapeutic nucleic acid vector results in a molecule with a longer half-life in serum, increased potency, and provides greater GH release in plasmid-injected animals (Draghia-Akli et al., 1999), herein incorporated by reference. Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors (Draghia-Akli et al., 1999).

Growth Hormone ("GH") and Growth Hormone Releasing Hormone ("GHRH") in Farm animals: The administration of recombinant growth hormone ("GH") or recombinant GHRH has been used in subjects for many years, but not as a pathway to treat arthritis, or to increase the arthritic patient welfare. More specifically, recombinant GH treatment in farm animals has been shown to enhance lean tissue deposition and/or milk production, while increasing feed efficiency (Etherton et al., 1986; Klindt et al., 1998). Numerous studies have shown that recombinant GH markedly reduces the amount of carcass fat and consequently the quality of products increases. However, chronic GH administration has practical, economical and physiological limitations that potentially mitigate its usefulness and effectiveness (Chung et al., 1985; Gopinath and Etherton, 1989b). Experimentally, recombinant GH-releasing hormone ("GHRH") has been used as a more physiological alternative. The use of GHRH in large animal species (e.g. pigs or cattle) not only enhances growth performance and milk production, but more importantly, the efficiency of production from both a practical and metabolic perspective (Dubreuil et al., 1990; Farmer et al., 1992). For example, the use of recombinant GHRH in lactating sows has beneficial effects on growth of the weanling pigs, yet optimal nutritional and hormonal conditions are needed for GHRH to exert its full potential (Farmer et al., 1996). Administration of GHRH and GH stimulate milk production, with an increase in feed to milk conversion. This therapy enhances growth primarily by increasing lean body mass (Lapierre et al., 1991; van Rooij et al., 2000) with overall improvement in feed efficiency. Hot and chilled carcass weights are increased and carcass lipid (percent of soft-tissue mass) is decrease by administration of GHRH and GH (Etherton et al., 1986).

Transgene Delivery and in vivo Expression: Although not wanting to be bound by theory, the delivery of specific transgenes to somatic tissue to correct inborn or acquired deficiencies and imbalances is possible. Such transgene-based drug delivery offers a number of advantages over the administration of recombinant proteins. These advantages include: the conservation of native protein structure; improved biological activity; avoidance of systemic toxicities; and avoidance of infectious and toxic impurities. Because the protein is synthesized and secreted continuously into the circulation, plasmid mediated therapy allows for prolonged production of the protein in a therapeutic range. In contrast, the primary limitation of using recombinant protein is the limited availability of protein after each administration.

In a plasmid-based expression system, a non-viral transgene vector may comprise of a synthetic transgene delivery system in addition to the nucleic acid encoding the therapeutic genetic product. In this way, the risks associated with the use of most viral vectors can be avoided, including the expression of viral proteins that can induce immune responses against target tissues and the possibility of DNA mutations or activations of oncogenes. The non-viral expression vector products generally have low toxicity due to the use of "species-specific" components for gene delivery, which minimizes the risks of immunogenicity generally associated with viral vectors. Additionally, integration of plasmid sequences into host chromosomes is below the rate of spontaneous mutation, so that this type of nucleic acid vector therapy should neither activate oncogenes nor inactivate tumor suppressor genes (Ledwith et al., 2000b; Ledwith et al., 2000a). As episomal systems residing outside the chromosomes, plasmids have defined pharmacokinetics and elimination profiles, leading to a finite duration of gene expression in target tissues.

Direct plasmid DNA gene transfer is currently the basis of many emerging nucleic acid therapy strategies and does not require viral components or lipid particles (Aihara and Miyazaki, 1998; Muramatsu et al., 2001). Skeletal muscle is target tissue, because muscle fiber has a long life span and can be transduced by circular DNA plasmids that are expressed in immunocompetent hosts (Davis et al., 1993; Tripathy et al., 1996). Plasmid DNA constructs are attractive candidates for direct therapy into the subjects skeletal muscle because the constructs are well-defined entities that are biochemically stable and have been used successfully for many years (Acsadi et al., 1991; Wolff et al., 1990). The relatively low expression levels of an encoded product that are achieved after direct plasmid DNA injection are sometimes sufficient to indicate bio-activity of secreted peptides (Danko and Wolff, 1994; Tsurumi et al., 1996). Previous reports demonstrated that human GHRH cDNA could be delivered to muscle by an injectable myogenic expression vector in mice where it transiently stimulated GH secretion to a modest extent over a period of two weeks (Draghia-Akli et al., 1997).

There are several different approaches that can be utilized for the treatment of arthritis. Because arthritis is a chronic condition, effective treatment may require the presence of therapeutic agents for extended periods of time. In the case of proteins, this is problematic. Gene therapeutic approaches may offer a solution to this problem. Experimental studies have confirmed the feasibility, efficacy and safety of gene therapy for the treatment of animal models of arthritis. Several different approaches have shown promise in this regard, including gene transfer to the synovial lining cells of individual joints and the systemic delivery of genes to extra-articular locations. One unexpected finding has been the 'contralateral effect' in which gene delivery to one joint of an animal with poly-articular disease leads to improvement of multiple joints. Investigation of this phenomenon has led to interest in cell trafficking and the genetic modification of antigen-presenting cells (Gouze et al., 2001). Different types of molecules have been used. For instance, therapeutic strategies to block tumor necrosis factor alpha (TNF-alpha) activity in experimental autoimmune arthritis models and rheumatoid arthritis have proved highly successful, and provide sustained beneficial effects (Mukherjee et al., 2003); gene transfer of interleukin-1 receptor antagonist was also used as a treatment modality for the equine patients and offers future promise for human patients with osteoarthritis (Frisbie et al., 2002). Plasmid mediated GHRH supplementation that determines a reduction in TNF-alpha levels in dogs with spontaneous malignancies may act further through this route in the treatment of arthritis (Draghia-Akli et al., 2002a).

Efforts have been made to enhance the delivery of plasmid DNA to cells by physical means including electroporation, sonoporation, and pressure. Although not wanting to be bound by theory, the administration of a nucleic acid construct by electroporation involves the application of a pulsed electric field to create transient pores in the cellular membrane without causing permanent damage to the cell, which allows exogenous molecules to enter the cell (Smith and Nordstrom, 2000). By adjusting the electrical pulse generated by an electroporetic system, nucleic acid molecules can travel through passageways or pores in the cell that are created during the procedure. U.S. Pat. No. 5,704,908 titled "Electroporation and iontophoresis catheter with porous balloon," issued on Jan. 6, 1998 with Hofmann et al., listed as inventors describes an electroporation apparatus for delivering molecules to cells at a selected location within a cavity in the body of a patient. Similar pulse voltage injection devices are also described in: U.S. Pat. No. 5,702,359 titled "Needle electrodes for mediated delivery of drugs and genes," issued on Dec. 30, 1997, with Hofmann, et al., listed as inventors; U.S. Pat. No. 5,439,440 titled "Electroporation system with voltage control feedback for clinical applications," issued on Aug. 8, 1995 with Hofmann listed as inventor; PCT application WO/96/12520 titled "Electroporetic Gene and Drug Therapy by Induced Electric Fields," published on May 5, 1996 with Hofmann et al., listed as inventors; PCT application WO/96/12006 titled "Flow Through Electroporation Apparatus and Method," published on Apr. 25, 1996 with Hofmann et al., listed as inventors; PCT application WO/95/19805 titled "Electroporation and Iontophoresis Apparatus and Method For insertion of Drugs and genes into Cells," published on Jul. 27, 1995 with Hofmann listed as inventor; and PCT application WO/97/07826 titled "In Vivo Electroporation of Cells," published on Mar. 6, 1997, with Nicolau et al., listed as inventors, the entire content of each of the above listed references is hereby incorporated by reference.

Recently, significant progress to enhance plasmid delivery in vivo and subsequently to achieve physiological levels of a secreted protein was obtained using the electroporation technique. Electroporation has been used very successfully to transfect tumor cells after injection of plasmid (Lucas et al., 2002; Matsubara et al., 2001)) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Previous studies using GHRH showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). Intramuscular injection of plasmid followed by electroporation has been used successfully in ruminants for vaccination purposes (Babiuk et al., 2003; Tollefsen et al., 2003). It has been observed that the electrode configuration affects the electric field distribution, and subsequent results (Gehl et al., 1999; Miklavcic et al., 1998). Although not wanting to be bound by theory, needle electrodes give consistently better results than external caliper electrodes in a large animal model.

The ability of electroporation to enhance plasmid uptake into the skeletal muscle has been well documented. Similarly, plasmids formulated with poly-L-glutamate ("PLG") or polyvinylpyrrolidone ("PVP") were observed to have an increase in plasmid transfection, which consequently increased the expression of a desired transgene. For example, plasmids formulated with PLG or PVP were observed to increase gene expression to up to 10 fold in the skeletal muscle of mice, rats, and dogs (Fewell et al., 2001; Mumper et al., 1998). Although not wanting to be bound by theory, the anionic polymer sodium PLG enhances plasmid uptake at low plasmid concentrations and reduces any possible tissue damage caused by the procedure. PLG is a stable compound and it is resistant to relatively high temperatures (Dolnik et al., 1993). PLG has been used to increase stability of anti-cancer drugs (Li et al., 2000) and as "glue" to close wounds or to prevent bleeding from tissues during wound and tissue repair (Otani et al., 1996; Otani et al., 1998). PLG has been used to increase stability in vaccine preparations (Matsuo et al., 1994) without increasing their immunogenicity. PLG also has been used as an anti-toxin after antigen inhalation or exposure to ozone (Fryer and Jacoby, 1993).

Although not wanting to be bound by theory, PLG increases the transfection of the plasmid during the electroporation process, not only by stabilizing the plasmid DNA and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002b) and will increase plasmid stability in vitro prior to injection. There are studies directed to electroporation of eukaryotic cells with linear DNA (McNally et al., 1988; Neumann et al., 1982) (Toneguzzo et al., 1988) (Aratani et al., 1992; Nairn et al., 1993; Xie and Tsong, 1993; Yorifuji and Mikawa, 1990), but these examples illustrate transfection into cell suspensions, cell cultures, and the like, and such transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

Although not wanting to be bound by theory, a GHRH cDNA can be delivered to muscle of mice and humans by an injectable myogenic expression vector where it can transiently stimulate GH secretion over a period of two weeks (Draghia-Akli et al., 1997). This injectable vector system was optimized by incorporating a powerful synthetic muscle promoter (Li et al., 1999) coupled with a novel protease-resistant GHRH molecule with a substantially longer half-life and greater GH secretory activity (pSP-HV-GHRH) (Draghia-Akli et al., 1999). Highly efficient electroporation technology was optimized to deliver the nucleic acid construct to the skeletal muscle of an animal (Draghia-Akli et al., 2002b). Using this combination of vector design and electric pulses plasmid delivery method, the inventors were able to show increased growth and favorably modified body composition in pigs (Draghia-Akli et al., 1999; Draghia-Akli et al., 2003) and rodents (Draghia-Akli et al., 2002c). The modified GHRH nucleic acid constructs increased red blood cell production in companion animals with cancer and cancer treatment-associated anemia (Draghia-Akli et al., 2002a). In pigs, available data suggested that the modified porcine HV-GHRH analog (SEQID# 1) was more potent in promoting growth and positive body composition changes than the wild-type porcine GHRH (Draghia-Akli et al., 1999).

Administering novel GHRH analog proteins (U.S. Pat. Nos. 5,847,066; 5846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833, 166; 4,228,158; 4,228,156; 4,226,857; 4,224,316; 4,223,021; 4,223,020; 4,223,019) for the purpose of increasing release of growth hormone have been reported. A GHRH analog containing the following mutations have been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. Pat. No. 6,551,996 titled "Super-active porcine growth hormone releasing hormone analog," issued on Apr. 22, 2003 with Schwartz, et al., listed as inventors ("the '996 Patent"), which teaches application of a GHRH analog containing mutations that improve the ability to elicit the release of growth hormone. In addition, the '996 Patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

U.S. Pat. No. 5,874,534 ("the '534 patent") and U.S. Pat. No. 5,935,934 ("the '934 patent") describe mutated steroid receptors, methods for their use and a molecular switch for nucleic acid vector therapy, the entire content of each is hereby incorporated by reference. A molecular switch for regulating expression in nucleic acid vector therapy and methods of employing the molecular switch in humans, animals, transgenic animals and plants (e.g. GeneSwitch®) are described in the '534 patent and the '934 patent. The molecular switch is described as a method for regulating expression of a heterologous nucleic acid cassette for nucleic acid vector therapy and is comprised of a modified steroid receptor that includes a natural steroid receptor DNA binding domain attached to a modified ligand binding domain. The modified binding domain usually binds only non-natural ligands, antihormones or non-native ligands. One skilled in the art readily recognizes natural ligands do not readily bind the modified ligand-binding domain and consequently have very little, if any, influence on the regulation or expression of the gene contained in the nucleic acid cassette.

In summary preventing or treating arthritis, and preventing and treating lameness particularly in animals, and improving the welfare of an arthritic subject were previously uneconomical and restricted in scope. The related art has shown that it is possible to improve these different conditions in a limited capacity utilizing recombinant protein technology, but these treatments have some significant drawbacks. It has also been taught that nucleic acid expression constructs that encode recombinant proteins are viable solutions to the problems of frequent injections and high cost of traditional recombinant therapy. There is a need in the art to expanded treatments for subjects with a disease by utilizing nucleic acid expression constructs that are delivered into a subject and express stable therapeutic proteins in vivo.

SUMMARY

One aspect of the current invention is a method of preventing or treating arthritis in a subject, and lameness, particularly in animals, improving the body condition score, quality of life and welfare of an arthritic or lame subject. The method generally comprises delivering into a tissue of the farm animals a nucleic acid expression construct that encodes a growth-hormone-releasing-hormone ("GHRH") or functional biological equivalent thereof. Specific embodiments of this invention encompass various modes of delivering into the tissue of the farm animals the nucleic acid expression construct (e.g. an electroporation method, a viral vector, in conjunction with a carrier, by parenteral route, or a combination thereof). In a first preferred embodiment, the nucleic acid expression construct is delivered via an electroporation method comprising: a) penetrating the tissue in the farm animal with a plurality of needle electrodes, wherein the plurality of needle electrodes are arranged in a spaced relationship; b) introducing the nucleic acid expression construct into the tissue between the plurality of needle electrodes; and c) applying an electrical pulse to the plurality of needle electrodes. A second preferred embodiment includes the nucleic acid expression construct being delivered in a single dose, and the single dose comprising a total of about a 0.1-5 mg of nucleic acid expression construct. Generally, the nucleic acid expression construct is delivered into a tissue of the farm animals comprising diploid cells (e.g. muscle cells). In a third specific embodiment, the nucleic acid expression construct used for transfection comprises a HV-GHRH plasmid, pAV0224 (SEQID#25). Other specific embodiments utilize other nucleic acid expression constructs (e.g. an optimized bovine GHRH plasmid, pAV0236 (SEQID#28); a TI-GHRH plasmid, pAV0239 (SEQID#30); wt-porcine GHRH plasmid, pAV0225 (SEQID#26); ovine GHRH plasmid, pAV0240 (SEQID#31); chicken GHRH plasmid, pAV0241 (SEQID#32); dog GHRH plasmid, pAV0235 (SEQID#27); cat GHRH plasmid, pAV0238 (SEQID#29); horse GHRH plasmid, pAV0242 (SEQID#33). In a fourth specific embodiment, the nucleic acid expression construct further comprises, a transfection-facilitating polypeptide (e.g. a charged polypeptide, or poly-L-glutamate). After delivering the nucleic acid expression construct into the tissues of the farm animals, expression of the encoded GHRH or functional biological equivalent thereof is initiated. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQID#14). The animal comprises a human, a food animal, a work animal (e.g. a pig, cow, sheep, goat or chicken), or a pet (e.g. horse, dog, cat).

Another aspect of the current invention are compositions comprising an isolated nucleic acid comprising a sequence that encodes a polypeptide of SeqID#9; an isolated nucleic acid expression construct comprising horse pAV0242 (SEQID#33); and an isolated nucleic acid consisting of HV-GHRH pAV0224 (SEQID#25); pig pAV0225 (SEQID#26); dog pAV0235 (SEQID#27); bovine pAV0236 (SEQID#28); cat pAV0238 (SEQID#29); TI-GHRH pAV0239 (SEQID#30); ovine pAV0240 (SEQID#31); chicken pAV0241 (SEQID#32); or horse pAV0242 (SEQID#33).

BRIEF DESCRIPTION OF THE DRAWINGS:

FIG. 16 shows the translation and consensus sequence of different species GHRH.

DETAILED DESCRIPTION OF THE PREFERRED EMBODIMENTS

Figure 1:
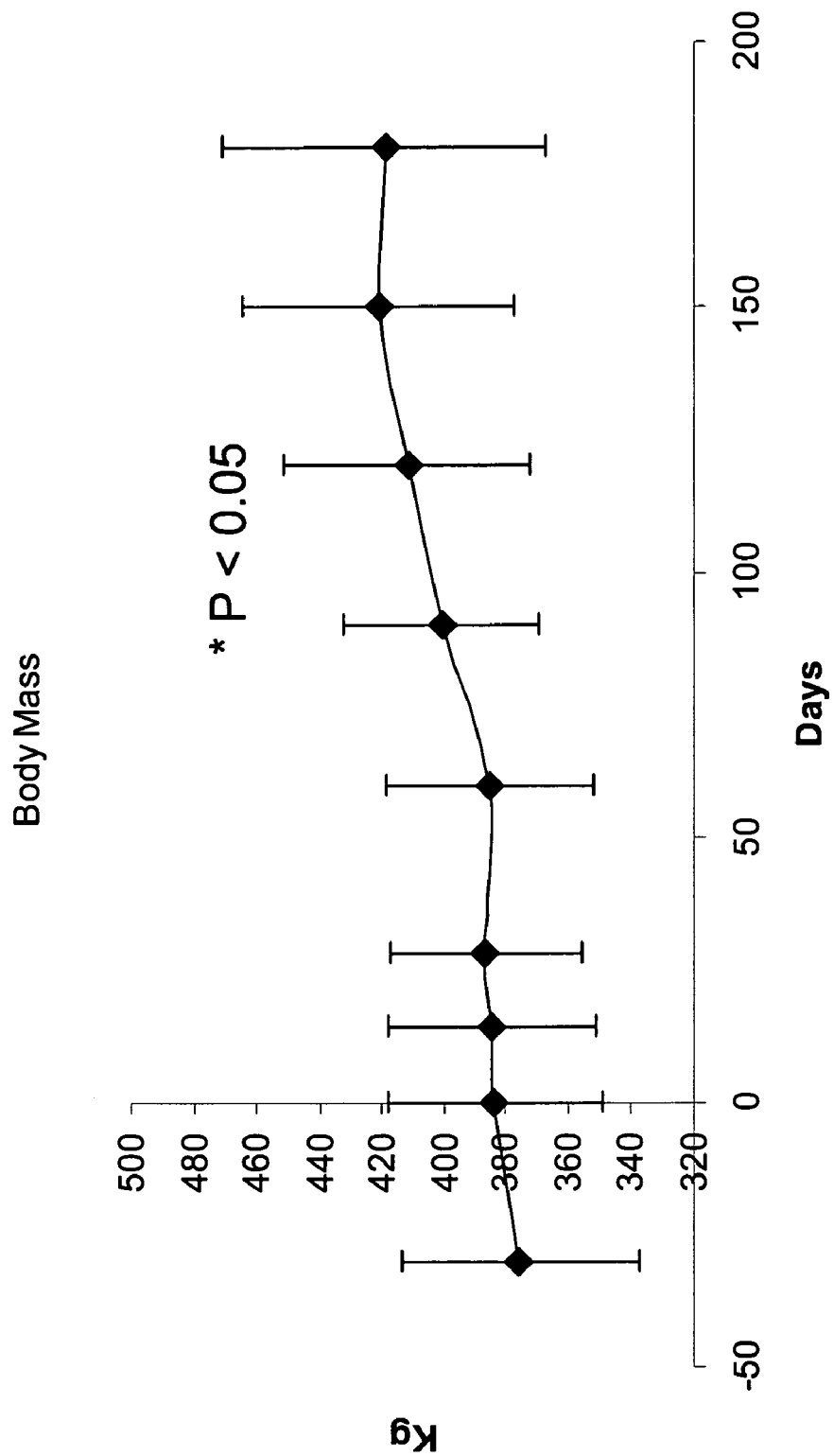
FIG. 1 shows body mass is significantly increased during a 180 days toxicology trial in healthy horses treated with a GHRH-expressing plasmid. Data is presented as mean±1SE, *P<0.05.

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "analog" as used herein includes any mutant of GHRH, or synthetic or naturally occurring peptide fragments of GHRH, such as HV-GHRH (SEQID#1), pig-GHRH (SEQID#2), bovine-GHRH (SEQID#3), dog-GHRH (SEQID#4), cat-GHRH (SEQID#5), TI-GHRH (SEQID#6), ovine-GHRH (SEQID#7), chicken-GHRH (SEQID#8), horse-GHRH (SEQID#9), TV-GHRH (SEQID#11), 15/27/28-GHRH (SEQID#12), (1-44)NH2 (SEQID#13), (1-40)OH (SEQID#10) forms, or any shorter form to no less than (1-29) amino acids.

The term "arthritis" as used herein is defined as a debilitating, chronic, systemic disease of unknown etiology that causes destruction of joint cartilage and bone. In humans, it generally occurs between the fourth and sixth decades of life, but juvenile forms are also common. It is characterized by joint stiffness, pain, and swelling, and is accompanied by a loss of body cell mass or cachexia that predominates in skeletal muscle, but also occurs in the viscera and immune system.

The term "bodily fat proportion" as used herein is defined as the body fat mass divided by the total body weight.

The term "body condition score" (BCS) as used herein is defined as a method to evaluate the overall nutrition and management of horses or any other farm animal.

The term "cassette" as used herein is defined as one or more transgene expression vectors.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "coding region" as used herein refers to any portion of the DNA sequence that is transcribed into messenger RNA (mRNA) and then translated into a sequence of amino acids characteristic of a specific polypeptide.

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "chronically ill" as used herein is defined as patients with conditions as chronic obstructive pulmonary disease, chronic heart failure, stroke, dementia, rehabilitation after hip fracture, chronic renal failure, arthritis, rheumatoid arthritis, and multiple disorders in the elderly, with doctor visits and/or hospitalization once a month for at least two years.

The term "donor-subject" as used herein refers to any species of the animal kingdom wherein cells have been removed and maintained in a viable state for any period of time outside the subject.

The term "donor-cells" as used herein refers to any cells that have been removed and maintained in a viable state for any period of time outside the donor-subject.

The term "electroporation" as used herein refers to a method that utilized electric pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide of growth hormone releasing hormone.

The term "functional biological equivalent" of GHRH as used herein is a polypeptide that has a distinct amino acid sequence from a wild type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis.

The term "GeneSwitch®" (a registered trademark of Valentis, Inc.; Burlingame, Calif.) as used herein refers to the technology of a mifepristone-inducible heterologous nucleic acid sequences encoding regulator proteins, GHRH, biological equivalent or combination thereof. A skilled artisan recognizes that antiprogesterone agent alternatives to mifepristone are available, including onapristone, ZK112993, ZK98734, and 5α pregnane-3,2-dione.

The term "growth hormone" ("GH") as used herein is defined as a hormone that relates to growth and acts as a chemical messenger to exert its action on a target cell. In a specific embodiment, the growth hormone is released by the action of growth hormone releasing hormone.

The term "growth hormone releasing hormone" ("GHRH") as used herein is defined as a hormone that facilitates or stimulates release of growth hormone, and in a lesser extent other pituitary hormones, such as prolactin.

The term "heterologous nucleic acid sequence" as used herein is defined as a DNA sequence comprising differing regulatory and expression elements.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

The term "immunotherapy" as used herein refers to any treatment that promotes or enhances the body's immune system to build protective antibodies that will reduce the symptoms of a medical condition and/or lessen the need for medications.

The term "lameness" as used herein is defined as an abnormal gait or locomotion characterized by limping (claudication) or not bearing full weight on a leg, usually associated with pain in the musculoskeletal system. Affected subjects may have reduced activity in standing up and moving including limping, sagging or stiffness and lack of flexion, and adoption of unusual postures.

The term "lean body mass" ("LBM") as used herein is defined as the mass of the body of an animal attributed to non-fat tissue such as muscle.

The term "modified cells" as used herein is defined as the cells from a subject that have an additional nucleic acid sequence introduced into the cell.

The term "modified-donor-cells" as used herein refers to any donor-cells that have had a GHRH-encoding nucleic acid sequence delivered.

The term "molecular switch" as used herein refers to a molecule that is delivered into a subject that can regulate transcription of a gene.

The term "nucleic acid expression construct" as used herein refers to any type of an isolated genetic construct comprising a nucleic acid coding for a RNA capable of being transcribed. The term "expression vector" can also be used interchangeably herein. In specific embodiments, the isolated nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter. The term "DNA fragment" as used herein refers to a substantially double stranded DNA molecule. Although the fragment may be generated by any standard molecular biology means known in the art, in some embodiments the DNA fragment or expression construct is generated by restriction digestion of a parent DNA molecule. The terms "expression vector," "expression cassette," or "expression plasmid" can also be used interchangeably. Although the parent molecule may be any standard molecular biology DNA reagent, in some embodiments the parent DNA molecule is a plasmid.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate" ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding GHRH or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing a nucleic acid-expression construct in vivo.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly linear DNA fragments, into the cells of the organism.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "quality of life" or "health related quality of life" of a subject as used herein refers to those attributes valued by patients and their owners, including: their resultant comfort and well-being; the extent to which they are able to maintain reasonable physical, emotional, and intellectual function; and the degree to which they retain their ability to participate in valued activities within the family, in the workplace, and in the community.

The term "welfare" of a subject as used herein refers at a state of being or doing well, performing tasks and activities at functional levels; condition of health, happiness, and comfort; well-being; prosperity.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "residual linear plasmid backbone" as used herein comprises any fragment of the plasmid backbone that is left at the end of the process making the nucleic acid expression plasmid linear.

The term "recipient-subject" as used herein refers to any species of the animal kingdom wherein modified-donor-cells can be introduced from a donor-subject.

The term "regulator protein" as used herein refers to any protein that can be used to control the expression of a gene, and that is increasing the rate of transcription in response to an inducing agent.

The term "secretagogue" as used herein refers to an agent that stimulates secretion. For example, a growth hormone secretagogue is any molecule that stimulates the release of growth hormone from the pituitary when delivered into an animal. Growth hormone releasing hormone is a growth hormone secretagogue.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (cows, chicken, fish, lambs, pigs, etc); and all others known in the art.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of linear DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly A sequence, or a 3' or 5' UTR.

The term "transfects" as used herein refers to introduction of a nucleic acid into a eukaryotic cell. In some embodiments, the cell is not a plant tissue or a yeast cell.

The term "vector" as used herein refers to any vehicle that delivers a nucleic acid into a cell or organism. Examples include plasmid vectors, viral vectors, liposomes, or cationic lipids. The term also refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

The term "viral backbone" as used herein refers to a nucleic acid sequence that does not contain a promoter, a gene, and a 3' poly A signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The term "vascular pressure pulse" refers to a pulse of pressure from a large volume of liquid to facilitate uptake of a vector into a cell. A skilled artisan recognizes that the amount and duration of the vascular pressure pulse is dependent on the tissue, size, and overall health of the recipient animal, and furthermore knows how to determine such parameters empirically.

Arthritis and lameness are major problems in human medicine and farm animal industry. One specific embodiment of the current invention is a method of treating a subject having arthritis. The method comprises: penetrating a muscle tissue in the subject with a plurality of needle electrodes, wherein the plurality of needle electrodes are arranged in a spaced relationship; delivering into the muscle tissue of the subject a nucleic acid expression construct that encodes a growth-hormone-releasing-hormone ("GHRH"), such that an amount of expressed GHRH is effective to alleviate a symptom of arthritis; and applying an electrical pulse to the plurality of needle electrodes, wherein the electrical pulse allows the nucleic acid expression construct to traverse a muscle cell membrane. A range of 0.1-5 mg of nucleic acid expression construct with a defined concentration of poly-L-glutamate polypeptide is delivered into the muscle tissue of the subject, and the nucleic acid expression construct comprises a sequence that encodes a polypeptide having an amino acid sequence that is at least 90% identical to the encoded GHRH of SEQID#14. The preferred subjects commprises a human, a ruminant animal, a food animal, a horse, or a work animal. While there are many symptoms that indicate arthritis a few examples comprise: joint stiffness, joint pain, joint swelling, lameness or a combination thereof. Other specific embodiments of this invention encompass various modes of delivering into the tissue of the subject the nucleic acid expression construct (e.g. an electroporation method, a viral vector, in conjunction with a carrier, by parenteral route, or a combination thereof).

A second preferred embodiment includes the nucleic acid expression construct being delivered in a single dose, and the single dose comprising a total of about a 0.1-5 mg of nucleic acid expression construct. Generally, the nucleic acid expression construct is delivered into a tissue of the subject comprising diploid cells (e.g. muscle cells).

In a third specific embodiment, the nucleic acid expression construct used for transfection comprises a HV-GHRH plasmid (SEQID#25). Other specific embodiments utilize other nucleic acid expression constructs (e.g. an optimized bovine GHRH plasmid, pAV0236 (SEQID#28); a TI-GHRH plasmid, pAV0239 (SEQID#30); wt-porcine GHRH plasmid, pAV0225 (SEQID#26); ovine GHRH plasmid, pAV0240 (SEQID#31); chicken GHRH plasmid, pAV0241 (SEQID#32); dog GHRH plasmid, pAV0235 (SEQID#27); cat GHRH plasmid, pAV0238 (SEQID#29); horse GHRH plasmid, pAV0242 (SEQID#33).

In a fourth specific embodiment, the nucleic acid expression construct further comprises, a transfection-facilitating polypeptide (e.g. a charged polypeptide, or poly-L-glutamate). After delivering the nucleic acid expression construct into the tissues of the subject, expression of the encoded GHRH or functional biological equivalent thereof is initiated. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQID#14). The animal comprises a human, a food animal, a work animal (e.g. a pig, cow, sheep, goat or chicken), or a pet (e.g. dog, cat, horse).

A second aspect of the current invention includes a method of improving a body condition score ("BCS") in arthritic subjects or lame animals comprising: delivering into a tissue of the subject a nucleic acid expression construct that encodes a growth-hormone-releasing-hormone ("GHRH") or functional biological equivalent thereof; wherein the BCS is an aid used to improve the overall nutritional state of the affected subject. The method generally comprises delivering into a tissue of the subject a nucleic acid expression construct that encodes a growth-hormone-releasing-hormone ("GHRH") or functional biological equivalent thereof. Specific embodiments of the second aspect of this invention encompass various modes of delivering into the tissue of the subject the nucleic acid expression construct (e.g. an electroporation method, a viral vector, in conjunction with a carrier, by parenteral route, or a combination thereof). In a fifth preferred embodiment, the nucleic acid expression construct is delivered via an electroporation method comprising: a) penetrating the tissue in the farm animal with a plurality of needle electrodes, wherein the plurality of needle electrodes are arranged in a spaced relationship; b) introducing the nucleic acid expression construct into the tissue between the plurality of needle electrodes; and c) applying an electrical pulse to the plurality of needle electrodes. A sixth preferred embodiment includes the nucleic acid expression construct being delivered in a single dose, and the single dose comprising a total of about a 0.1-5 mg of nucleic acid expression construct. Generally, the nucleic acid expression construct is delivered into a tissue of the farm animals comprising diploid cells (e.g. muscle cells). In a seventh specific embodiment, the nucleic acid expression construct used for transfection comprises a HV-GHRH plasmid (SEQID#1). Other specific embodiments utilize other nucleic acid expression constructs (e.g. an optimized bovine GHRH plasmid, pAV0236 (SEQID#28); a TI-GHRH plasmid, pAV0239 (SEQID#30); wt-porcine GHRH plasmid, pAV0225 (SEQID#26); ovine GHRH plasmid, pAV0240 (SEQID#31); chicken GHRH plasmid, pAV0241 (SEQID#32); dog GHRH plasmid, pAV0235 (SEQID#27); cat GHRH plasmid, pAV0238 (SEQID#29); horse GHRH plasmid, pAV0242 (SEQID#33). In a eighth specific embodiment, the nucleic acid expression construct further comprises, a transfection-facilitating polypeptide (e.g. a charged polypeptide, or poly-L-glutamate). After delivering the nucleic acid expression construct into the tissues of the subject expression of the encoded GHRH or functional biological equivalent thereof is initiated. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQID#14). The animal comprises a human, food animal, or a work animal (e.g. a pig, cow, sheep, goat or chicken), or a pet (e.g. dog, cat, horse).

The current invention also pertains to methods useful for increasing quality of life and welfare in an arthritic subject or lame animal. The general method of this invention comprises treating a subject with plasmid mediated gene supplementation. The method comprises delivering a nucleic acid expression construct that encodes a growth-hormone-releasing-hormone ("GHRH") or functional biological equivalent thereof into a tissue, such as a muscle, of the subject. Specific embodiments of this invention are directed toward treating or preventing arthritis or lameness in a subject, increasing body condition scores in treated animals, and enhancing immune function in treated animals. The subsequent in vivo expression of the GHRH or biological equivalent in the subject is sufficient to enhance welfare. It is also possible to enhance this method by placing a plurality of electrodes in a selected tissue, then delivering nucleic acid expression construct to the selected tissue in an area that interposes the plurality of electrodes, and applying a cell-transfecting pulse (e.g. electrical) to the selected tissue in an area of the selected tissue where the nucleic acid expression construct was delivered. However, the cell-transfecting pulse need not be an electrical pulse, a different method, such as vascular pressure pulse can also be utilized. Electroporation, direct injection, gene gun, or gold particle bombardment are also used in specific embodiments to deliver the nucleic acid expression construct encoding the GHRH or biological equivalent into the subject. The subject in this invention comprises an animal (e.g. a human, a pig, a horse, a cow, a mouse, a rat, a monkey, a sheep, a goat, a dog, or a cat).

Recombinant GH replacement therapy is widely used in agriculture and clinically, with beneficial effects, but generally, the doses are supraphysiological. Such elevated doses of recombinant GH are associated with deleterious side-effects, for example, up to 30% of the recombinant GH treated subjects develop at a higher frequency insulin resistance (Gopinath and Etherton, 1989a; Gopinath and Etherton, 1989b; Verhelst et al., 1997) or accelerated bone epiphysis growth and closure in pediatric patients (Blethen and Rundle, 1996). In addition, molecular heterogeneity of circulating GH may have important implications in growth and homeostasis (Satozawa et al., 2000; Tsunekawa et al., 1999; Wada et al., 1998). Unwanted side effects result from the fact that treatment with recombinant exogenous GH protein raises basal levels of GH and abolishes the natural episodic pulses of GH. In contradistinction, no side effects have been reported for recombinant GHRH therapies. The normal levels of GHRH in the pituitary portal circulation range from about 150-to-800 pg/ml, while systemic circulating values of the hormone are up to about 100-500 pg/ml. Some patients with acromegaly caused by extracranial tumors have level that is nearly 100 times as high (e.g. 50 ng/ml of immunoreactive GHRH) (Thomer et al., 1984). Long-term studies using recombinant GHRH therapies (1-5 years) in children and elderly humans have shown an absence of the classical GH side-effects, such as changes in fasting glucose concentration or, in pediatric patients, the accelerated bone epiphysal growth and closure or slipping of the capital femoral epiphysis (Chevalier et al., 2000) (Duck et al., 1992; Vittone et al., 1997).

Numerous studies in humans, sheep or pigs showed that continuous infusion with recombinant GHRH protein restores the normal GH pattern without desensitizing GHRH receptors or depleting GH supplies (Dubreuil et al., 1990). As this system is capable of a degree of feed-back which is abolished in the GH therapies, GHRH recombinant protein therapy may be more physiological than GH therapy. However, due to the short half-life of GHRH in vivo, frequent (one to three times per day) intravenous, subcutaneous or intranasal (requiring 300-fold higher dose) administrations are necessary (Evans et al., 1985; Thorner et al., 1986). Thus, as a chronic therapy, recombinant GHRH protein administration is not practical. A gene transfer approach, however could overcome this limitations to GHRH use. Moreover, a wide range of doses can be therapeutic. The choice of GHRH for a gene therapeutic application is favored by the fact that the gene, cDNA and native and several mutated molecules have been characterized for the pig, cattle and other species (Bohlen et al., 1983; Guillemin et al., 1982); we have isolated the cDNA of cat, dog and horse specific GHRH. The measurement of therapeutic efficacy is straightforward and unequivocal.

Among the non-viral techniques for gene transfer in vivo, the direct injection of plasmid DNA into muscle is simple, inexpensive, and safe. The inefficient DNA uptake into muscle fibers after simple direct injection had led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996). Recently, significant progress to enhance plasmid delivery in vivo and subsequently to achieve physiological levels of a secreted protein was obtained using the electroporation technique. Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Preliminary experiments indicated that for a large animal model, needle electrodes give consistently better reproducible results than external caliper electrodes.

The ability of electroporation to enhance plasmid uptake into the skeletal muscle has been well documented, as described above. In addition, plasmid formulated with PLG or polyvinylpyrrolidone ("PVP") has been observed to increase gene transfection and consequently gene expression to up to 10 fold in the skeletal muscle of mice, rats and dogs (Fewell et al., 2001; Mumper et al., 1998). Although not wanting to be bound by theory, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency.

The plasmid supplementation approach to enhance animal quality of life and welfare, prevent or treat arthritis and/or prevent or treat lameness, and increase body condition scores described herein offers advantages over the limitations of directly injecting recombinant GH or GHRH protein. Expression of novel biological equivalents of GHRH that are serum protease resistant can be directed by an expression plasmid controlled by a synthetic muscle-specific promoter. Expression of such GHRH or biological equivalent thereof elicited high GH and IGF-I levels in subjects that have had the encoding sequences delivered into the cells of the subject by intramuscular injection and in vivo electroporation. Although in vivo electroporation is the preferred method of introducing the heterologous nucleic acid encoding system into the cells of the subject, other methods exist and should be known by a person skilled in the art (e.g. electroporation, lipofectamine, calcium phosphate, ex vivo transformation, direct injection, DEAE dextran, sonication loading, receptor mediated transfection, microprojectile bombardment, etc.). For example, it may also be possible to introduce the nucleic acid sequence that encodes the GHRH or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). The GHRH sequence can be cloned into an adenovirus vector or an adeno-associated vector and delivered by simple intramuscular injection, or intravenously or intra-arterially. Plasmid DNA carrying the GHRH sequence can be complexed with cationic lipids or liposomes and delivered intramuscularly, intravenously or subcutaneous.

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establishing controlled expression of any specific nucleic acid sequence within tissues at certain levels that are useful for plasmid mediated supplementation. The preferred means for administration of vector and use of formulations for delivery are described above.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhanced utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determine the bioavailability of the vector within the body. Other elements of the formulation function as ligands that interact with specific receptors on the surface or interior of the cell. Other elements of the formulation function to enhance entry into the cell, release from the endosome, and entry into the nucleus.

Delivery can also be through use of DNA transporters. DNA transporters refer to molecules that bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand that recognizes specific receptors or other functional groups such as a protein complexed with a cationic group that binds to DNA. Examples of cations which may be used are spermine, spermine derivatives, histone, cationic peptides and/or polylysine; one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs plasmid-mediated supplementation and the genetically engineered cells can also be easily put back with out causing damage to the patient's muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 region of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

Although not wanting to be bound by theory, it is believed that in order to provide an acceptable safety margin for the use of such heterologous nucleic acid sequences in humans, a regulated gene expression system is mandated to possess low levels of basal expression of GHRH, and still retain a high ability to induce. Thus, target gene expression can be regulated by incorporating molecular switch technology. The HV-GHRH (SEQID# 1) or biological equivalent molecule displays a high degree of stability in serum, with a half-life of 6 hours, versus the natural GHRH, that has a 6-12 minutes half-life. Thus, by combining the powerful electroporation DNA delivery method with stable and regulable GHRH or biological equivalent encoded nucleic acid sequences, a therapy can be utilized that will enhance animal welfare, decrease culling rates and increase body condition scores.

Vectors

The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operatively linked coding sequence in a particular host cell. In addition to control sequences that govern transcription and translation, vectors and expression vectors may contain nucleic acid sequences that serve other functions as well and are described infra.

Plasmid Vectors

In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. Other plasmids contain genes for kanamycin or neomycin, or have a non-antibiotic selection mechanism. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is derived from pBlueScript KS+ and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase ("GST") soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCRTM, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | Relevant References |
|---|---|
| β-Actin | (Kawamoto et al., 1988; Kawamoto et al., 1989) |
| Muscle Creatine Kinase (MCK) | (Horlick and Benfield, 1989; Jaynes et al., 1988) |
| Metallothionein (MTII) | (Inouye et al., 1994; Narum et al., 2001; Skroch et al., 1993) |
| Albumin | (Pinkert et al., 1987; Tronche et al., 1989) |
| β-Globin | (Tronche et al., 1990; Trudel and Costantini, 1987) |
| Insulin | (German et al., 1995; Ohlsson et al., 1991) |
| Rat Growth Hormone | (Larsen et al., 1986) |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| Cytomegalovirus (CMV) | (Boshart et al., 1985; Dorsch-Hasler et al., 1985) |
| Synthetic muscle specific promoters (c5-12, c1-28) | (Draghia-Akli et al., 1999; Draghia-Akli et al., 2002c; Li et al., 1999) |

TABLE 2

Element/Inducer

| Element | Inducer |
|---|---|
| MT II | Phorbol Ester (TFA) |
|  | Heavy metals |
| MMTV (mouse mammary tumor virus) | Glucocorticoids |
| β-Interferon | Poly(rI)x/Poly(rc) |
| Adenovirus 5 E2 | E1A |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | E1A, SV40 Large T Antigen |
| Proliferin | Phorbol Ester-TPA |

TABLE 2-continued

Element/Inducer

| Element | Inducer |
|---|---|
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), DIA dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (Li et al., 1999), which contains a proximal serum response element ("SRE") from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame"with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites ("IRES") elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, (Chandler et al., 1997).

Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal, skeletal alpha actin 3' UTR or the human or bovine growth hormone polyadenylation signal, convenient and known to function well in various target cells. Polyadenylation may increase the stability of the transcript or may facilitate cytoplasmic transport.

Origins of Replication

In order to propagate a vector in a host cell, it may contain one or more origins of replication sites (often termed "ori"), which is a specific nucleic acid sequence at which replication is initiated. Alternatively, an autonomously replicating sequence ("ARS") can be employed if the host cell is yeast.

Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase ("tk") or chloramphenicol acetyltransferase ("CAT") may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Mutagenesis

Where employed, mutagenesis was accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as $E.\ coli$ polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as $E.\ coli$ cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multi-residue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances maintain a resting transmembrane potential of circa 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the interelectrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol, and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

Overcoming the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. It is desirable that the voltage pulse be as homogenous as possible and of the correct amplitude. Excessive field strength results in the lysing of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation in the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

One example of an electroporation device that may be used to effectively facilitate the introduction of a macromolecule into cells of a selected tissue of a subject was described in U.S. patent application Ser. No. 10/657,725 filed on Sep. 8, 2003, titled "CONSTANT CURRENT ELECTROPORATION DEVICE AND METHODS OF USE," with Smith et al., listed as inventors, the entirty of which is hereby encorporated by reference. The electroporation device comprises an electro-kinetic device ("EKD") whose operation is specified by software or firmware. The EKD produces a series of programmable constant-current pulse patterns between electrodes in an array based on user control and input of the pulse parameters and allows the storage and acquisition of current waveform data. The electroporation device also comprises a replaceable electrode disk having an array of needle electrodes, a central injection channel for an injection needle, and a removable guide disk.

Restriction Enzymes

In some embodiments of the present invention, a linear DNA fragment is generated by restriction enzyme digestion of a parent DNA molecule. Examples of restriction enzymes are provided below.

| Name | Recognition Sequence |
|---|---|
| AatII | GACGTC |
| Acc65 I | GGTACC |
| Acc I | GTMKAC |
| Aci I | CCGG |
| Acl I | AACGTT |
| Afe I | AGCGGT |
| Afl II | CTTAAG |
| Afl III | ACRYGT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |

| Name | Recognition Sequence |
|---|---|
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| BsI I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CAGGAG |
| BstAP I | GCANNNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |

| Name | Recognition Sequence |
| --- | --- |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspA1 I | CMGCKG |
| Msp I | CCGG |
| Mwo I | GCNNNNNNNGC |
| Nae I | GCCGGC |
| Nar I | GGCGCC |
| NaoMI V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| PleI | GAGTC |

| Name | Recognition Sequence |
| --- | --- |
| Pme I | GTTTAAAC |
| Pml I | CACGTG |
| PpuM I | RGGWCCY |
| PshA I | GAGNNNNGTC |
| Psi I | TTATAA |
| PspG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCGGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |

-continued

| Name | Recognition Sequence |
|---|---|
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG |
| Xho I | CTCGAG |
| Xma I | CCCGGG |
| Xmn I | GAANNNNTTC |

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Restriction enzymes are used to ensure plasmid integrity and correctness.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Construction of DNA Vectors and Methods in Animal Subject

DNA constructs: In order to prevent or treat arthritis and/or prevent or treat lameness in affected subjects, increase body condition scores, and quality of life and welfare in arthritic or lame subjects by utilizing plasmid mediated gene supplementation, it was first necessary to design several GHRH constructs. Briefly, the plasmid vectors contained the muscle specific synthetic promoter SPc5-12 (SEQID#15)(Li et al., 1999) attached to a wild type species-specific or analog GHRH. Some wild-type GHRH sequences were cloned in our laboratory (dog, cat and horse); others (chicken, ovine, bovine, porcine) were synthesized according to the specialized literature. The analog GHRH sequences were generated by site directed mutagenesis as described (Draghia-Akli et al., 1999). Briefly, mammalian GHRH analog cDNA's were generated by site directed mutagenesis of GHRH cDNA (SEQID#18) (Altered Sites II in vitro Mutagenesis System, Promega, Madison, Wis.), and cloned into the BamHI/Hind III sites of pSPc5-12, to generate the specific GHRH construct. The 3' untranslated region (3'UTR) of growth hormone was cloned downstream of GHRH cDNA. The resultant plasmids contained mammalian analog coding region for GHRH, and the resultant amino acid sequences were not naturally present in mammals. Although not wanting to be bound by theory, the prevention or treatment of arthritis and/or prevention or treatment of lameness in affected subjects, increased body condition scores, and quality of life and welfare in arthritic or lame subjects are determined ultimately by the circulating levels of GHRH hormones. Several different plasmids encoded different mutated or wild type amino acid sequences of GHRH or functional biological equivalents thereof, for example:

```
Plasmid
Encoded Amino Acid Sequence
HV-GHRH:
                                            (SEQID#1)
HVDAIFTNSYRKVLAQLSARKLLQDILNRQQGERNQEQGA-OH Pig-GHRH:
                                            (SEQID#2)
YADAIFTNSYRKVLGQLSARKLLQDIMSRQQGERNQEQGA-OH Bovine-GHRH:
                                            (SEQID#3)
YADAIFTNSYRKVLGQLSARKLLQDIMNRQQGERNQEQGA-OH Dog-GHRH:
                                            (SEQID#4)
YADAIFTNSYRKVLGQLSARKLLQDIMSRQQGERNREQGA-OH Cat-GHRH:
                                            (SEQID#5)
YADAIFTNSYRKVLGQLSARKLLQDIMSRQQGERNQEQGA-OH TI-GHRH:
                                            (SEQID#6)
YIDAIFTNSYRKVLAQLSARKLLQDILNRQQGERNQEQGA-OH Ovine-GHRH:
                                            (SEQID#7)
YADAIFTNSYRKILGQLSARKLLQDIMNRQQGERNQEQGA-OH Chicken-GHRH:
                                            (SEQID#8)
HADGIFSKAYRKLLGQLSARNYLHSLMAKRVGSGLGDEAEPLS-OH Horse-GHRH (partial):
                                            (SEQID#9)
-ADAIFTNNYRKVLGQLSARKILQDIMSR----------OH human-GHRH:
                                            (SEQID#10)
YADAIFTNSYRKVLGQLSARKLLQDIMSRQQGESNQERGA-OH TV-GHRH:
                                            (SEQID#11)
YVDAIFTNSYRKVLAQLSARKLLQDILNRQQGERNQEQGA-OH TA-15/27/28-GHRH:
                                            (SEQID#12)
YADAIFTNSYRKVLAQLSARKLLQDILNRQQGERNQEQGA-OH
```

In general, the encoded GHRH or functional biological equivalent thereof is of formula:

```
                                              (SEQID#14)
-X1-X2-DAIFTNSYRKVL-X3-QLSARKLLQDI-X4-X5-RQQGE-X6-
N-X7-E-X8-GA-OH
``` wherein: $X_1$ is a D- or L-isomer of an amino acid selected from the group consisting of tyrosine ("Y"), or histidine ("H"); $X_2$ is a D- or L-isomer of an amino acid selected from the group consisting of alanine ("A"), valine ("V"), or isoleucine ("I"); $X_3$ is a D- or L-isomer of an amino acid selected from the group consisting of alanine ("A") or glycine ("G"); $X_4$ is a D- or L-isomer of an amino acid selected from the group consisting of methionine ("M"), or leucine ("L"); $X_5$ is a D- or L-isomer of an amino acid selected from the group consisting of serine ("S") or asparagines ("N"); $X_6$ is a D- or L-isomer of an amino acid selected from the group consisting of arginine ("R"), or serine ("S"); $X_7$ is a D- or L-isomer of an amino acid selected from the group consisting of arginine ("R"), or glutamine ("Q"); and $X_8$ is a D- or L-isomer of an amino acid selected from the group consisting of arginine ("R"), or glutamine ("Q").

The plasmids described above do not contain polylinker, IGF-I gene, a skeletal alpha-actin promoter or a skeletal alpha actin 3' UTR/NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and poly-nucleotides) in selected amino acids (or codons) may be substituted. A peptide comprising a functional biological equivalent of GHRH is a polypeptide that has been engineered to contain distinct amino acid sequences while simultaneously having similar or improved biologically activity when compared to GHRH. For example one biological activity of GHRH is to facilitate growth hormone ("GH") secretion in the subject.

Figure 8:
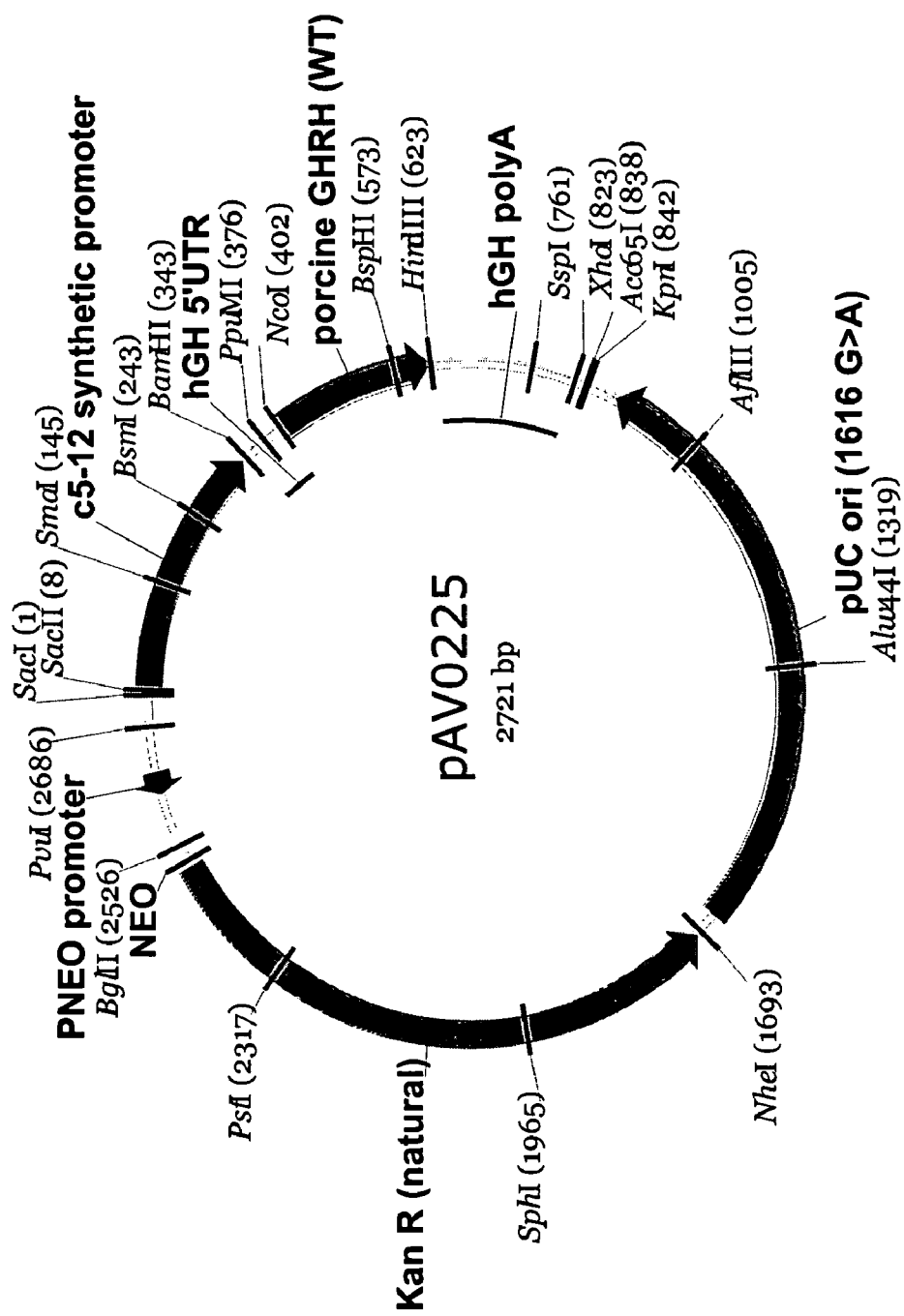
FIG. 8 shows a restriction map of pAV0225 expression plasmid.
Figure 9:
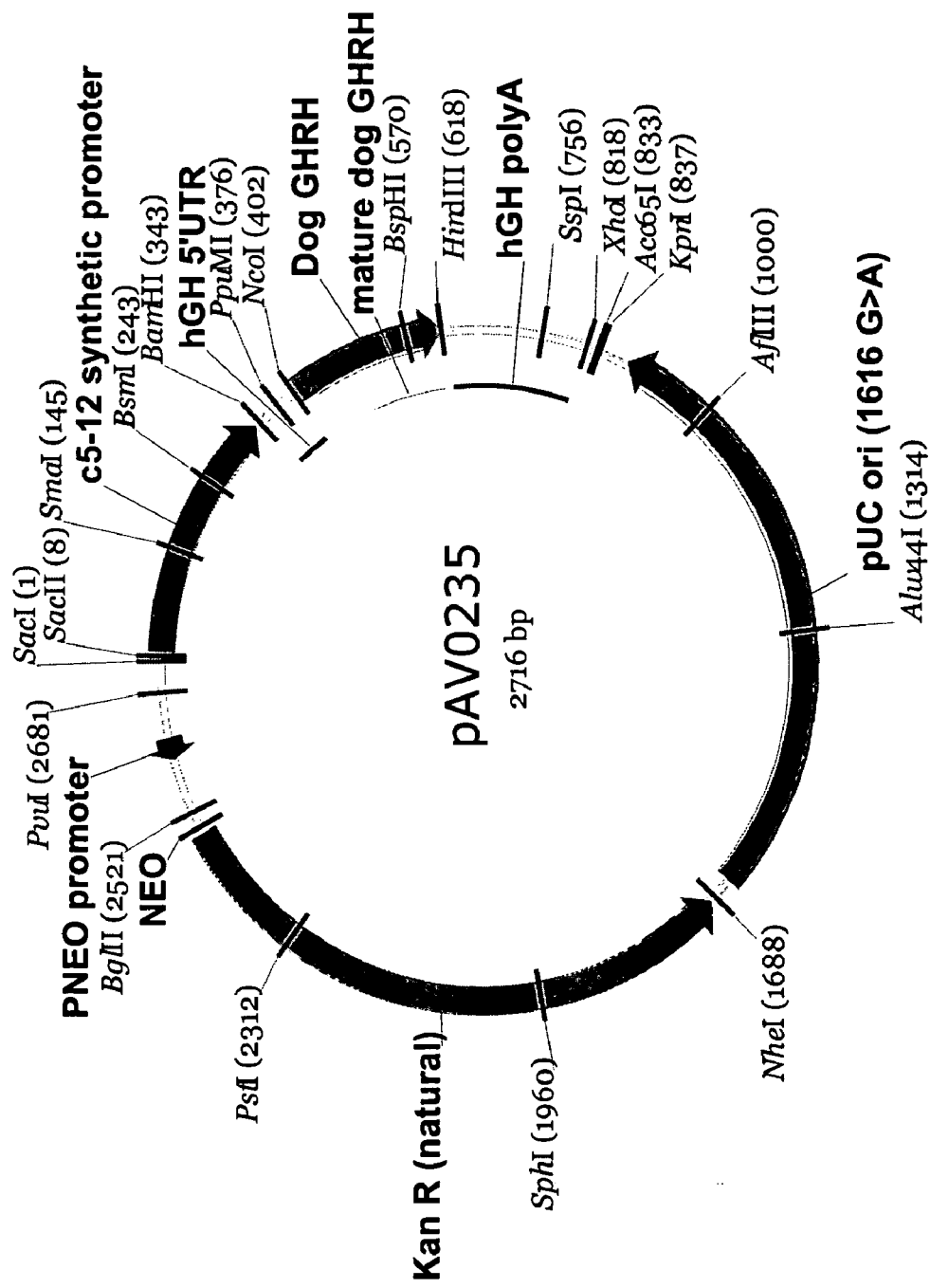
FIG. 9 shows a restriction map of pAV0235 expression plasmid.
Figure 10:
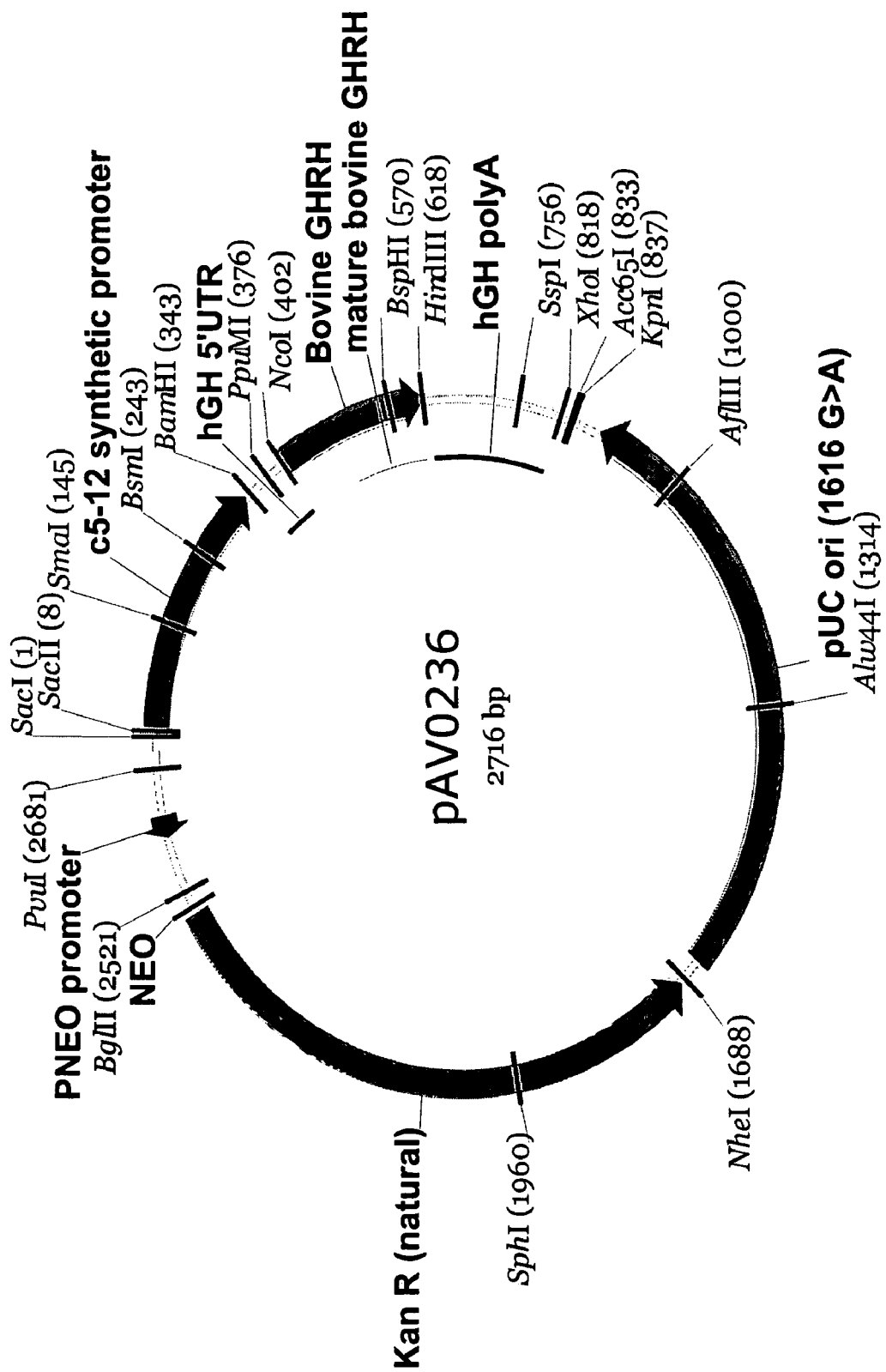
FIG. 10 shows a restriction map of pAV0236 expression plasmid.
Figure 11:
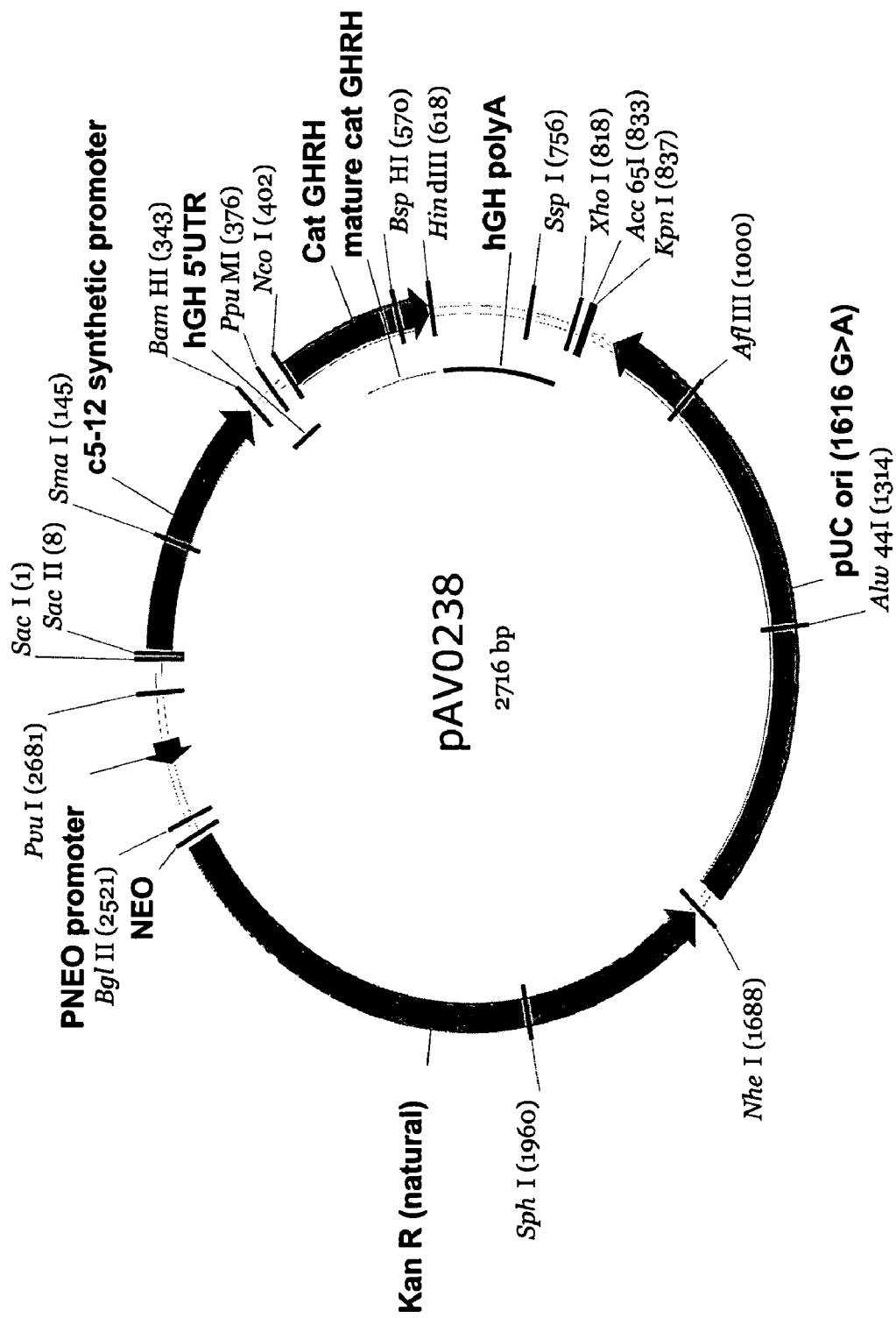
FIG. 11 shows a restriction map of pAV0238 expression plasmid.
Figure 12:
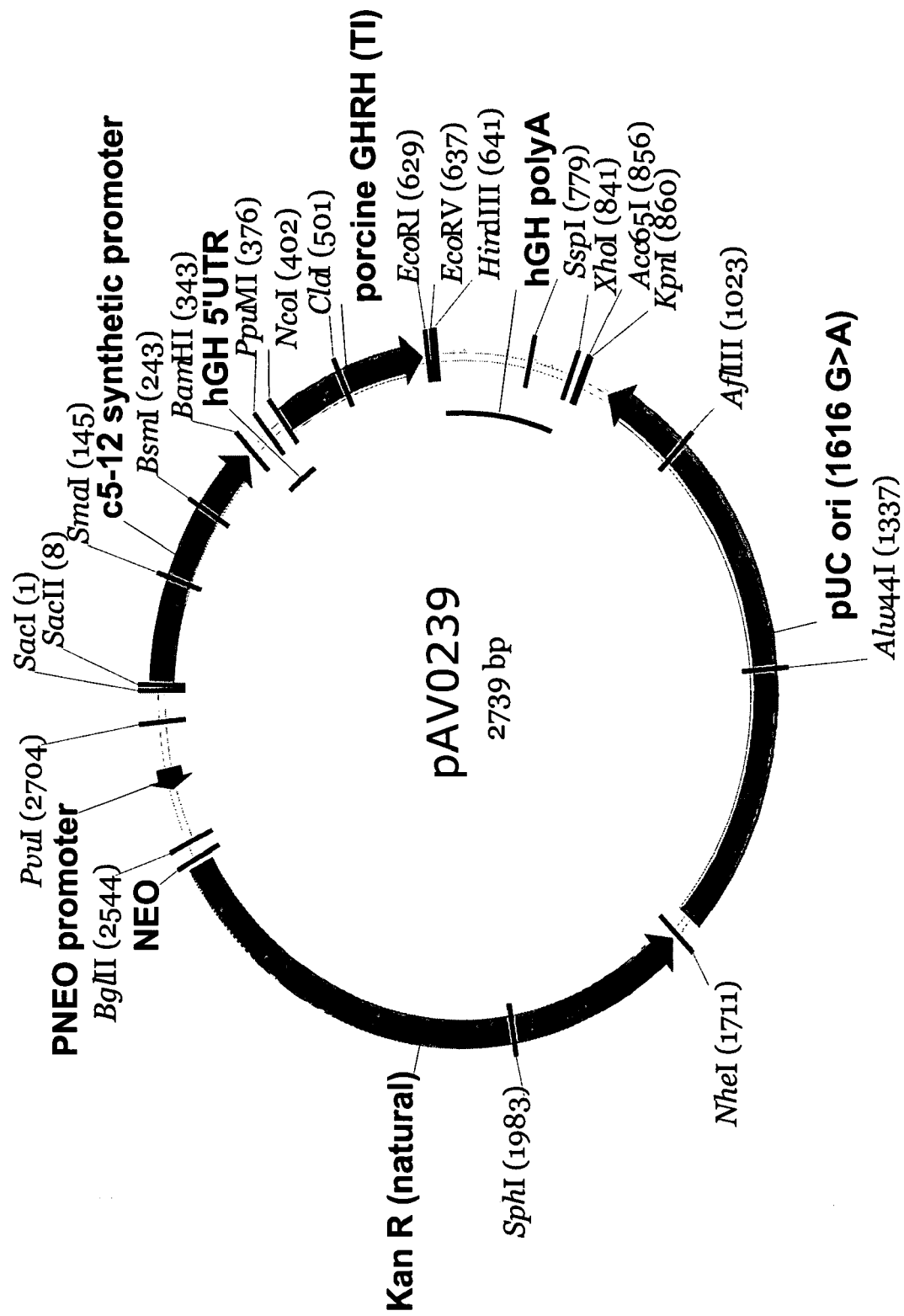
FIG. 12 shows a restriction map of pAV0239 expression plasmid.
Figure 13:
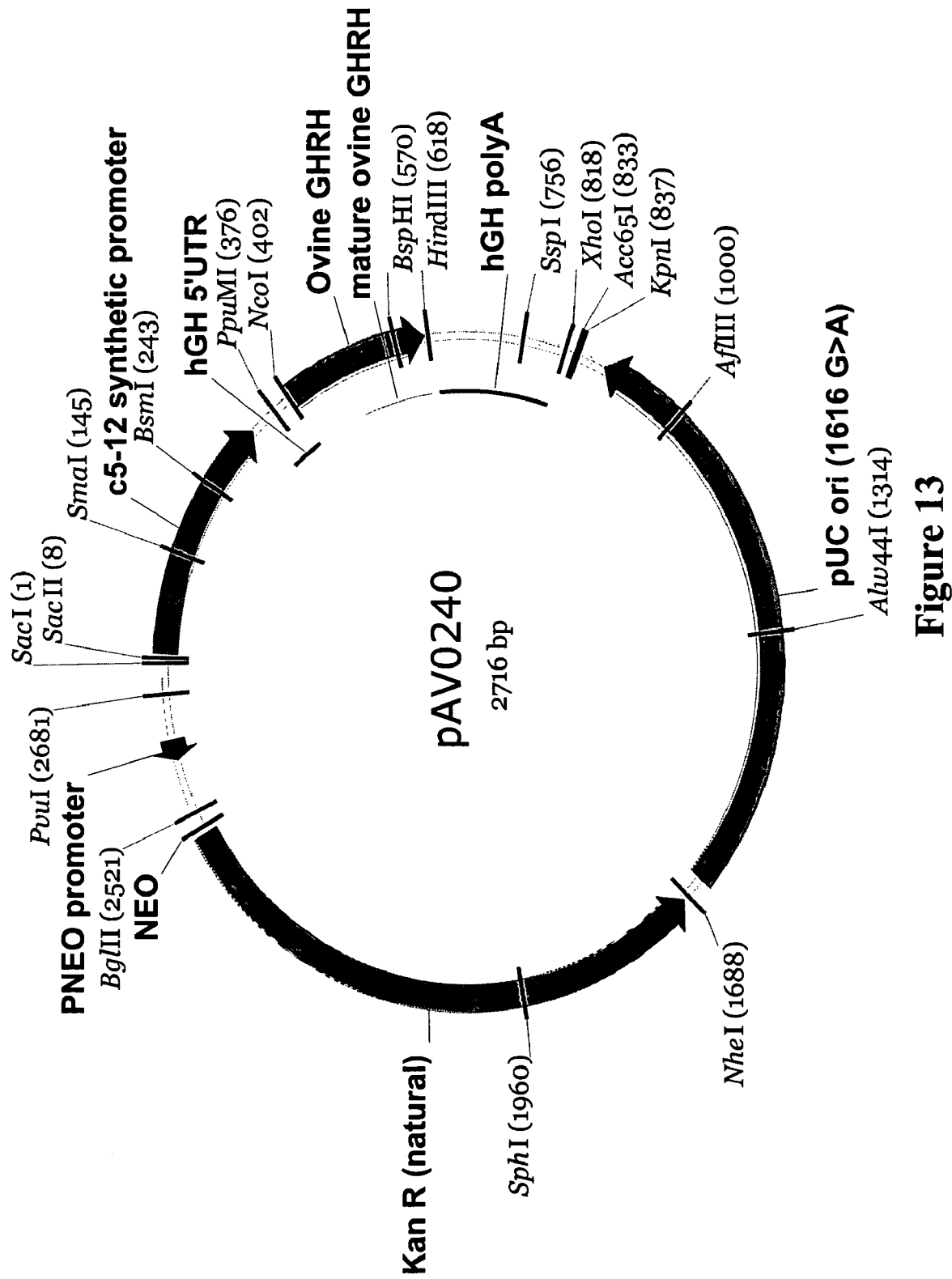
FIG. 13 shows a restriction map of pAV0240 expression plasmid.
Figure 14:
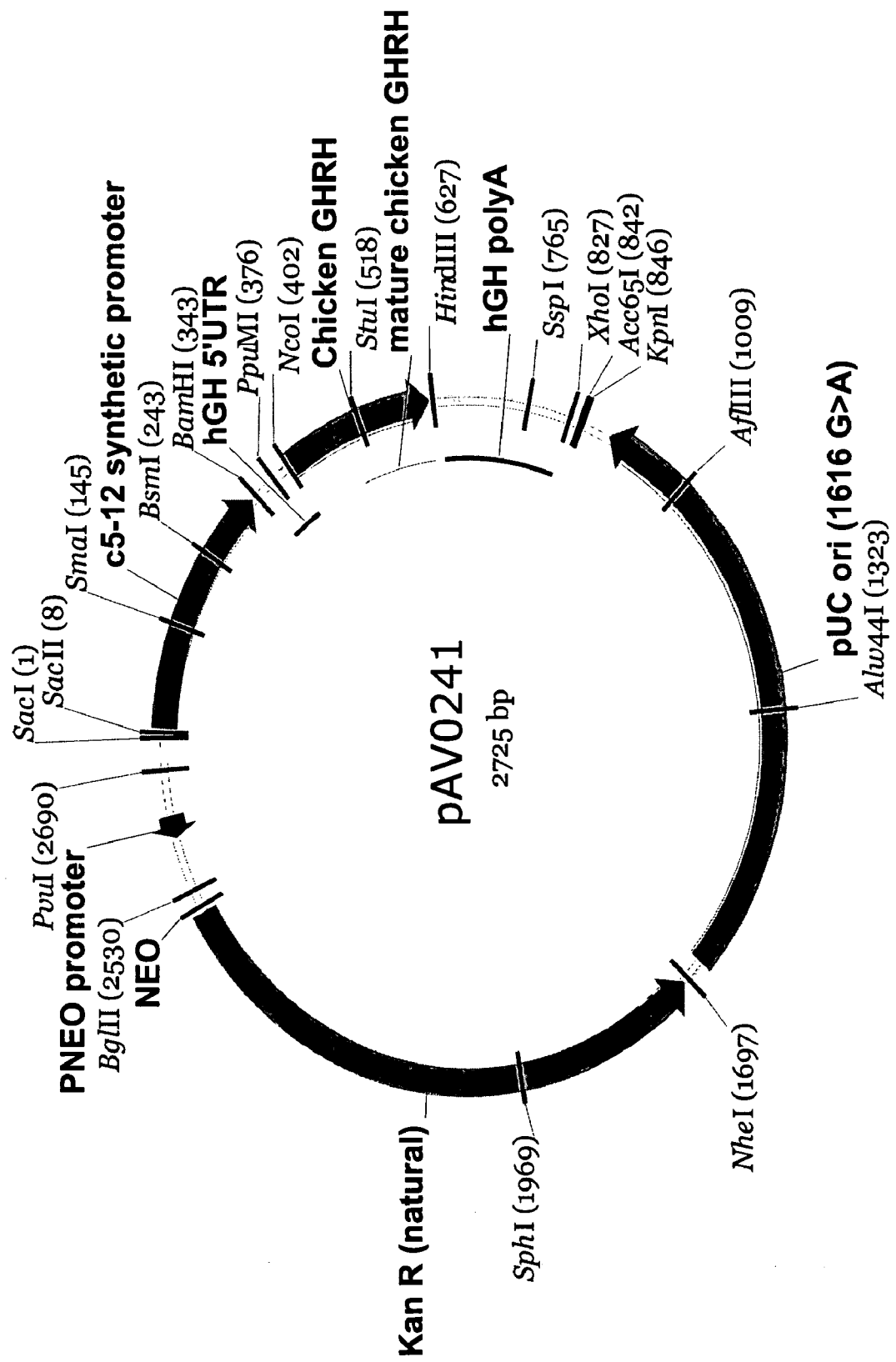
FIG. 14 shows a restriction map of pAV0241 expression plasmid.
Figure 15:
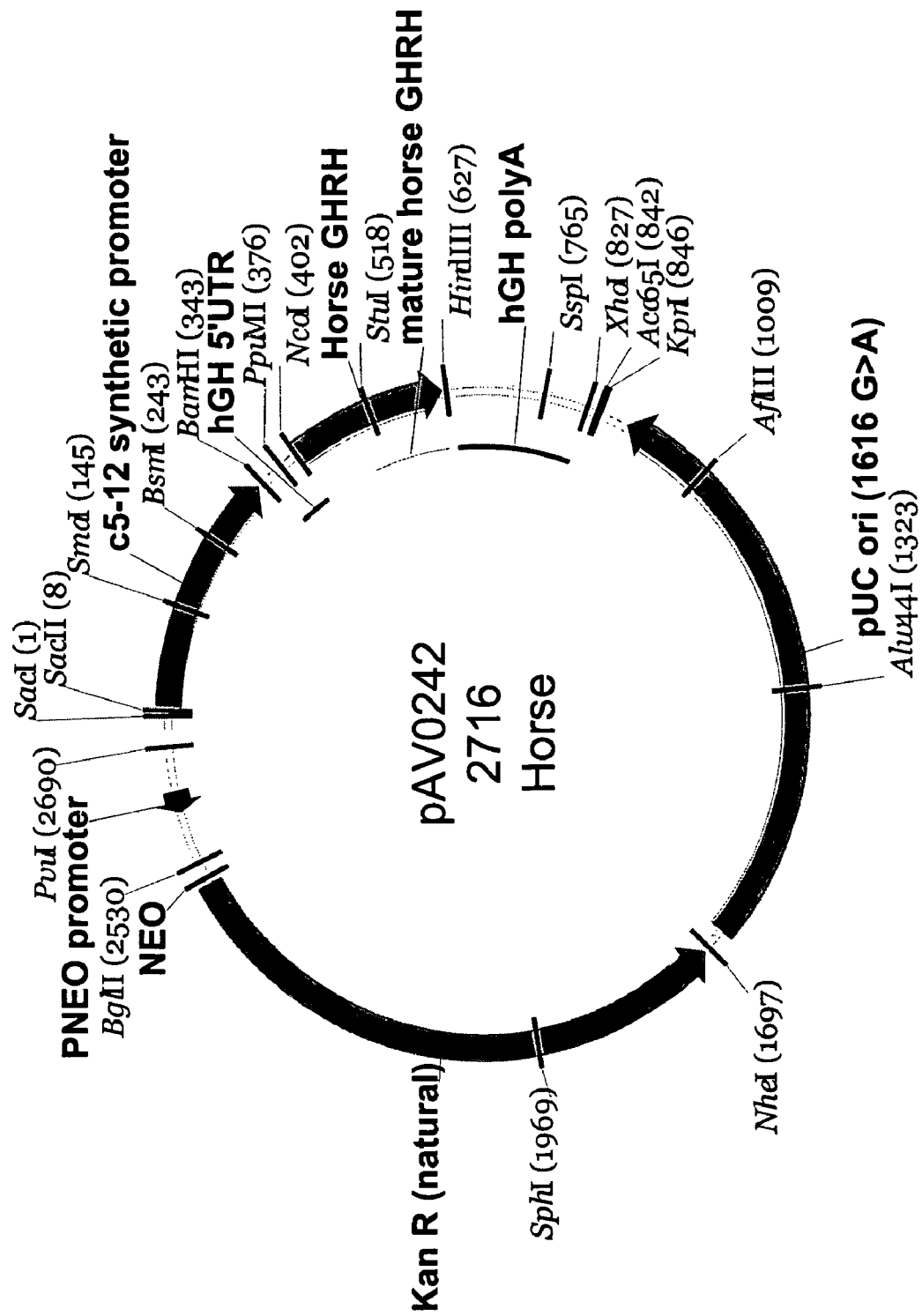
FIG. 15 shows a restriction map of pAV0242 expression plasmid.

Optimized Plasmid Backbone. One aspect of the current invention is the optimized plasmid backbone. The synthetic plasmids presented below contain eukaryotic sequences that are synthetically optimized for species-specific mammalian transcription. An existing pSP-HV-GHRH plasmid ("pAV0125") (SEQID#22), was synthetically optimized to form a new plasmid (SEQID#25). The plasmid pAV0125 was described in U.S. Pat. No. 6,551,996 titled "Super-active porcine growth hormone releasing hormone analog," issued on Apr. 22, 2003 with Schwartz, et al., listed as inventors ("the Schwartz '996 Patent"), which teaches application of a GHRH analog containing mutations that improve the ability to elicit the release of growth hormone. This 3,534 bp plasmid pAV0125 (SEQID #22) contains a plasmid backbone with various component from different commercially available plasmids, for example, a synthetic promoter SPc5-12 (SEQID #15), a modified porcine GHRH sequence (SEQID #20), and a 3' end of human growth hormone (SEQID #37). Other specific examples of optimized synthetic plasmids include an optimized wt-porcine GHRH plasmid, pAV0225 (SEQID#26) FIG. 8; dog GHRH plasmid, pAV0235 (SEQID#27) FIG. 9; bovine GHRH plasmid, pAV0236 (SEQID#28) FIG. 10; cat GHRH plasmid, pAV0238 (SEQID#29) FIG. 11; a TI-GHRH plasmid, pAV0239 (SEQID#30) FIG. 12; ovine GHRH plasmid, pAV0240 (SEQID#31) FIG. 13; chicken GHRH plasmid, pAV0241 (SEQID#32) FIG. 14; horse GHRH plasmid, pAV0242 (SEQID#33) FIG. 15. The therapeutic encoded gene for such optimized plasmids may also include optimized nucleic acid sequences that encode modified GHRH molecules or functional biological equivalents thereof (e.g. see FIG. 16).

Example 2

Toxicology Studies in Horses

The purpose of this study was to determine if the GHRH plasmid delivery by intramuscular injection followed by electroporation was safe and effective in horses. Animal were treated at day 0 with 2.5mg codon optimized pSP-wt-GHRH (pAV0225) (SEQID#26) FIG. 8, followed at 80 seconds by electroporation using the electroporator device and needle delivery device described in U.S. patent application Ser. No. 10/657,725, the entire content of which is hereby incorporated by reference. The electroporator settings were 1 Amp-intensity of the electric field, 5 pulses, 52 milliseconds/pulse, 1 second interval between pulses. Needles were 21 gauge, 1 inch in length, and completed inserted into the muscle trough the intact skin. The plasmid was formulated in a 0.01% poly-L-glutamate solution, as described (Draghia-Akli et al., 2002b; Draghia-Akli and Smith, 2003). The injection was performed under light anesthesia to avoid involuntary movements of the animals. This 180-days study involved 6 normal adult mares (mean age 4.8±1.06 years, range 4-7 years) using a longitudinal self-controlled experimental design. The mares had a mean body mass of 375.75±38 kg, range 306-397 kg. General body condition, behavior, complete blood counts, clinical chemistries and selected endocrine parameters were used to assess the safety and effectiveness of the treatment. All mares were subjected to two control data set collected 30 days and 7 days prior to electroporation. Each data set consisted of a physical examination, including determination of body mass and blood collection. Following treatment by 2.5 mg plasmid injection and electroporation, additional data sets were collected at days 14, 28, 60, 90, 120, 150, and 180.

None of the horse used in the study suffered any detectable adverse reactions or complications following treatment. There were no significant reactions at the treatment site, no adverse changes in body condition, and none of the measured parameters exceeded the normal range expected for the normal horse.

Figure 2:
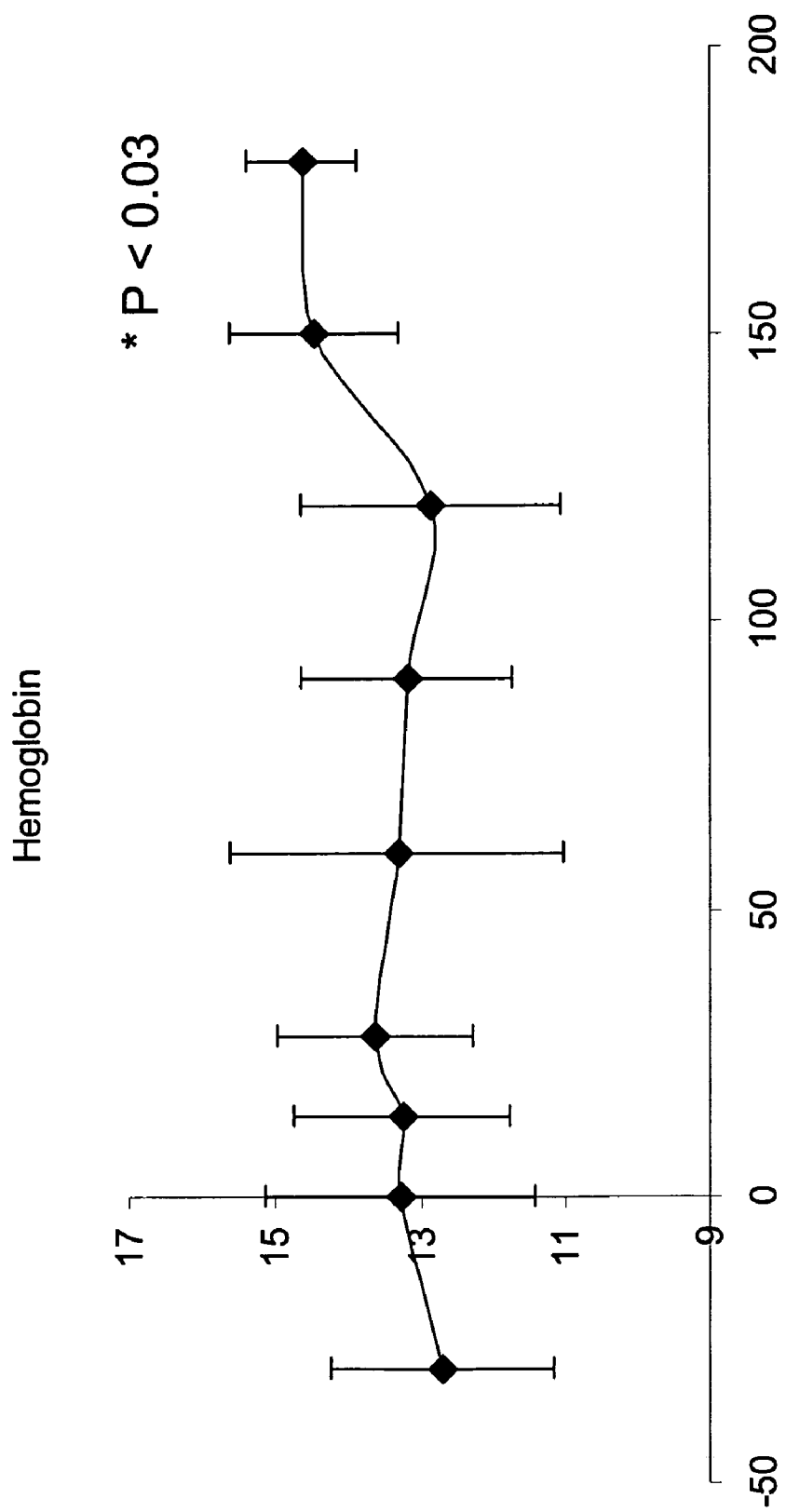
FIG. 2 shows hemoglobin levels are significantly increased during a 180 days toxicology trial in healthy horses treated with a GHRH-expressing plasmid. Data is presented as mean±1SE, *P<0.03.
Figure 3:
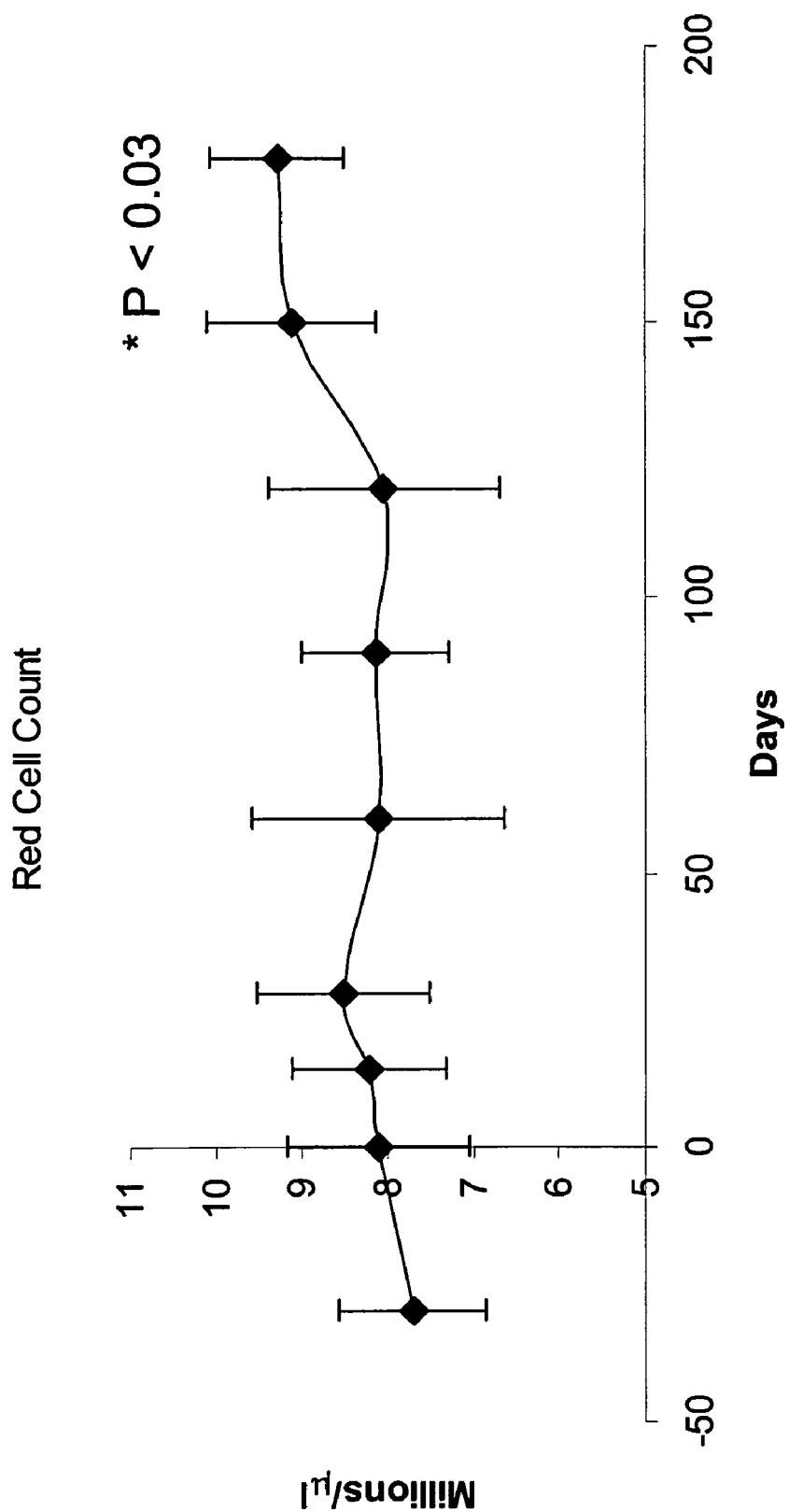
FIG. 3 shows red blood cell counts (RBC) are significantly increased during a 180 days toxicology trial in healthy horses treated with a GHRH-expressing plasmid. Data is presented as mean±1SE, *P<0.03.
Figure 4:
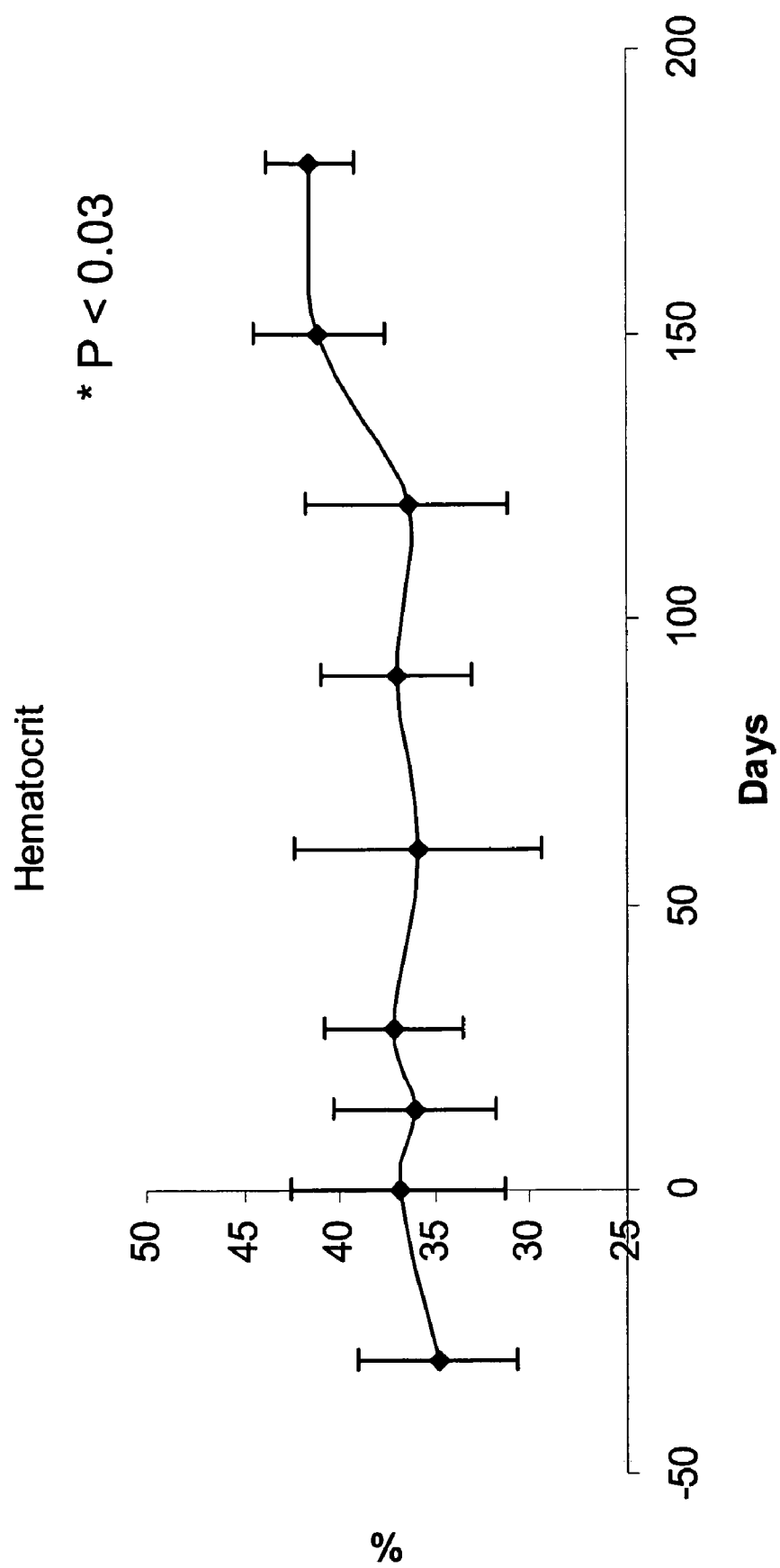
FIG. 4 shows hematocrit levels that are significantly increased during a 180 days toxicology trial in healthy horses treated with a GHRH-expressing plasmid. Data is presented as mean±1SE, *P<0.03.
Figure 5:
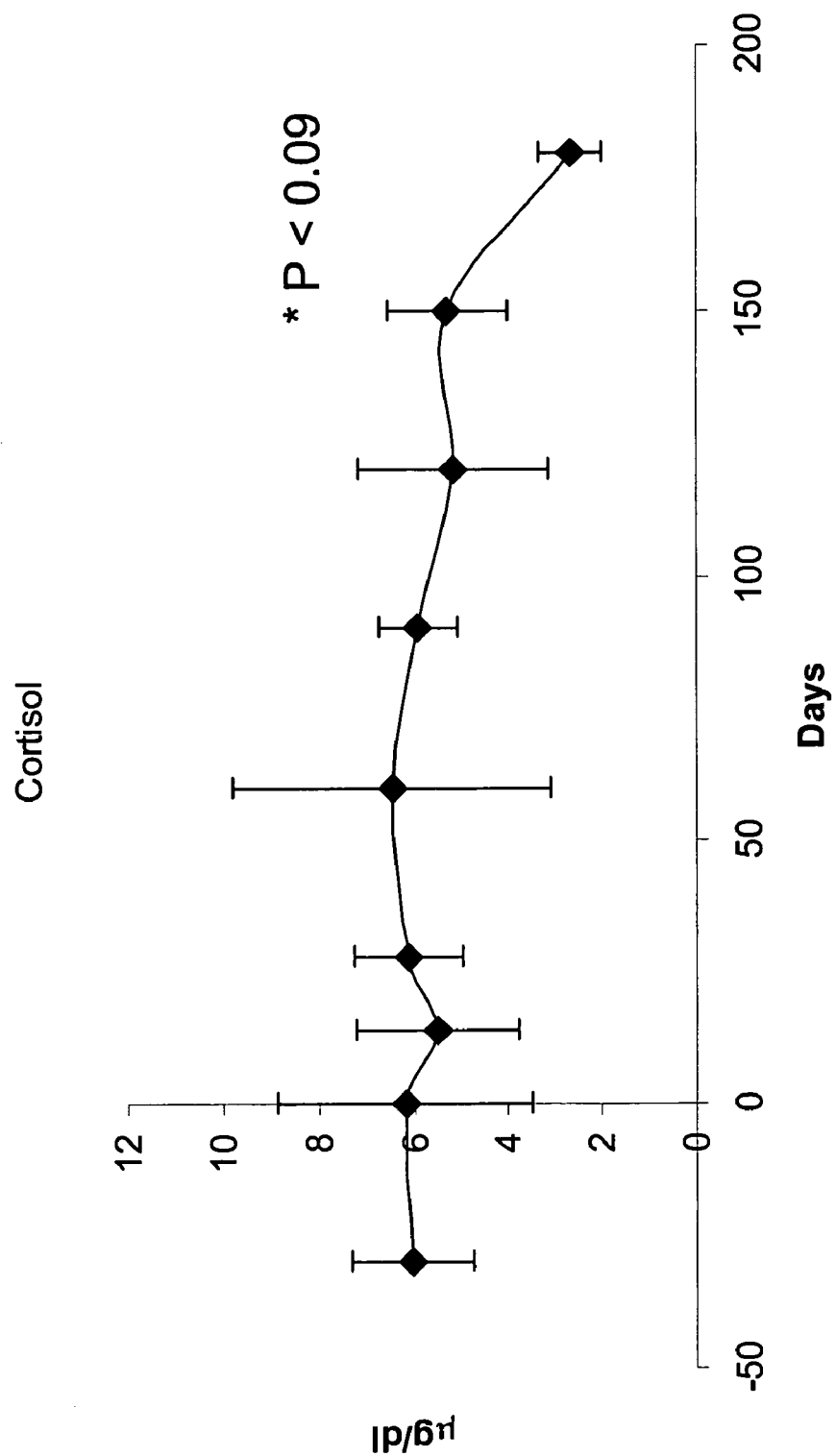
FIG. 5 shows cortisol levels are slightly decreased during a 180 days toxicology trial in healthy horses treated with a GHRH-expressing plasmid. Data is presented as mean±1SE, *P<0.09.
Figure 6:
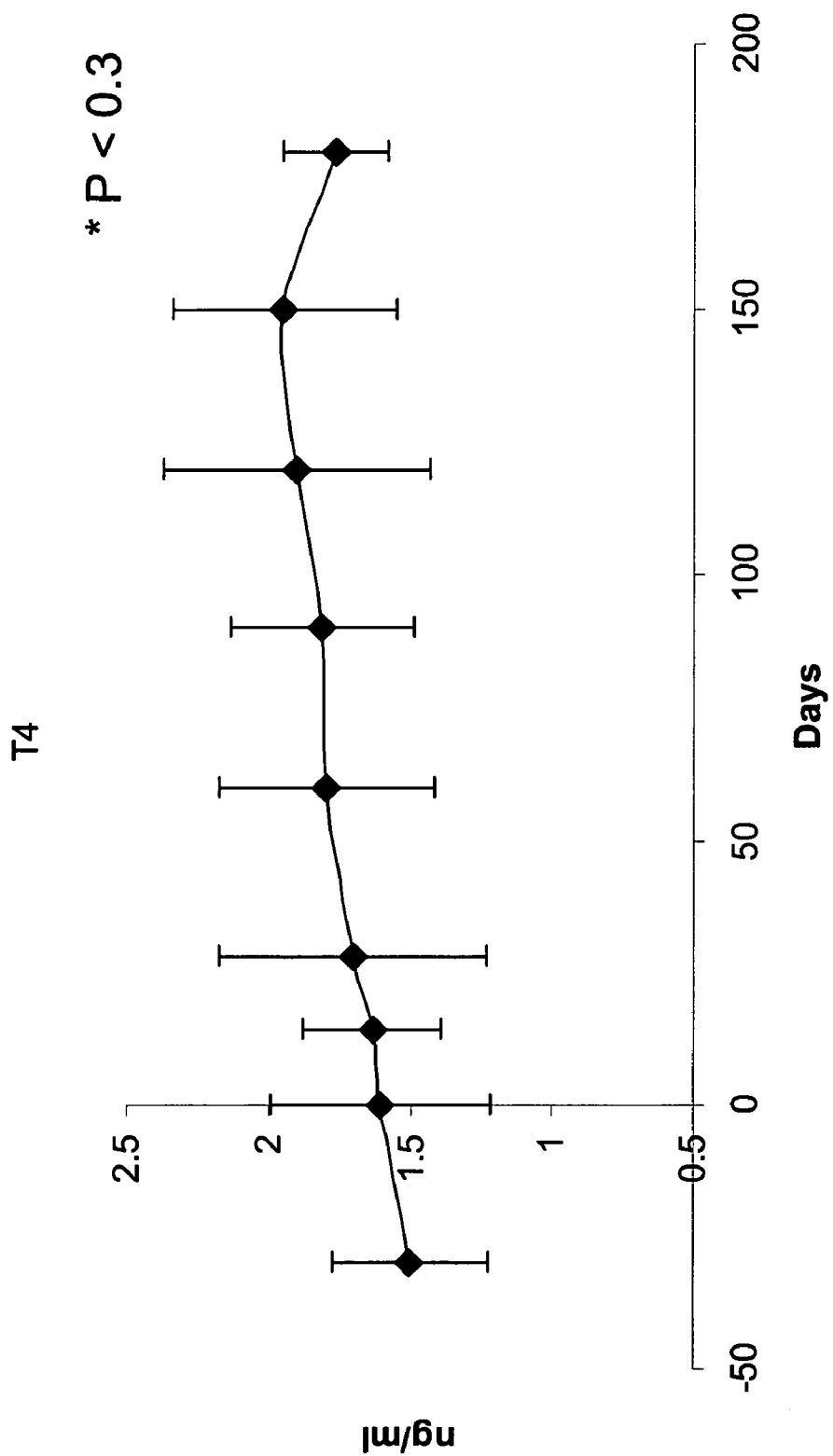
FIG. 6 shows thyroid hormone T4 levels are slightly increased during a 180 days toxicology trial in healthy horses treated with a GHRH-expressing plasmid. Data is presented as mean±1 SE, *P<0.3.
Figure 7:
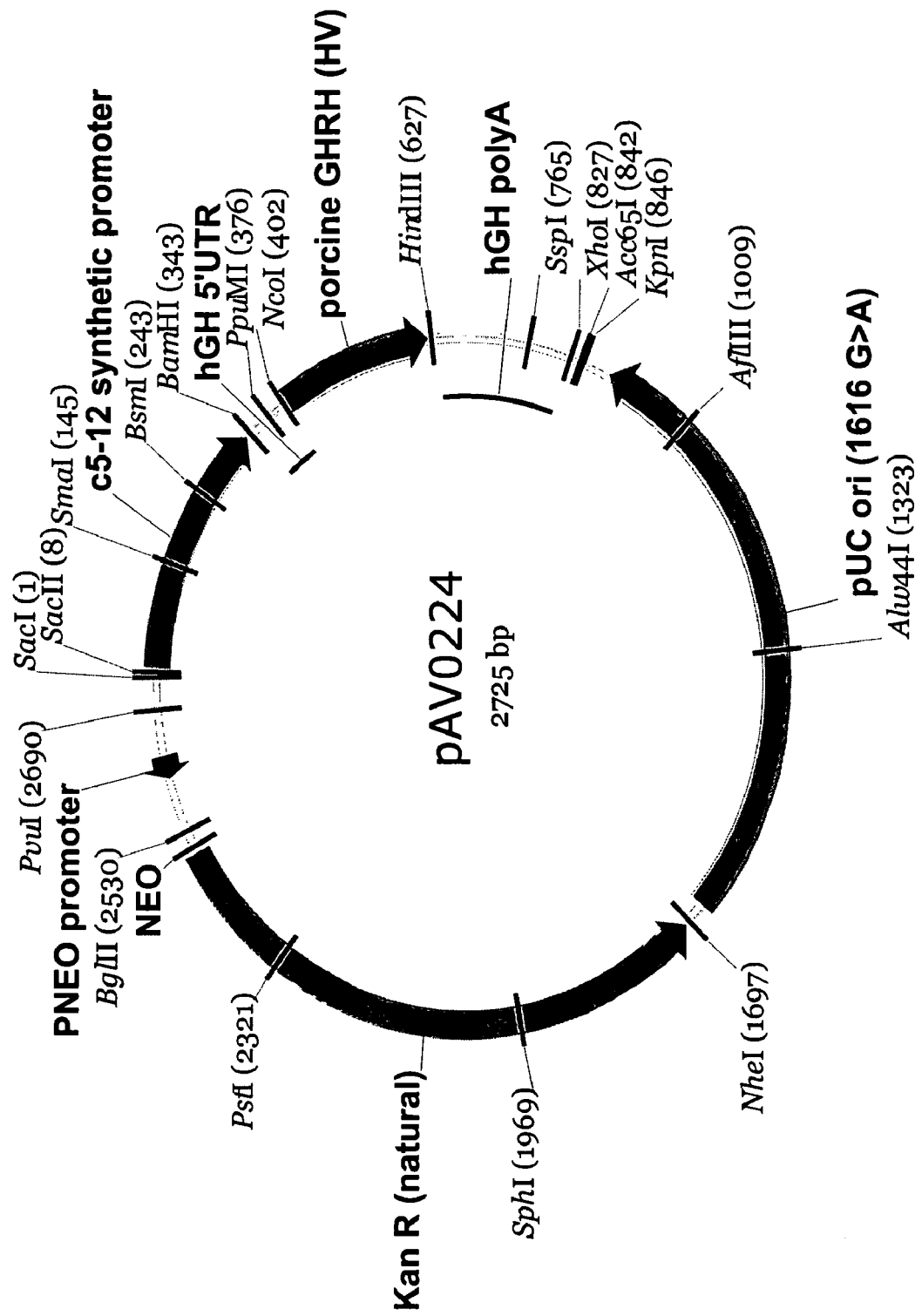
FIG. 7 shows a restriction map of pAV0224 expression plasmid.

Evidence of the effectiveness of plasmid GHRH therapy was provided by an increase in body mass (FIG. 1), increase erythrocyte production, as hematocrit (FIG. 4), red blood cell production (FIG. 3), and hemoglobin (FIG. 2) and changes in the pattern of clinical parameters, as decreases in ACTH and cortisol levels (FIG. 5) and slight increases in thyroid hormones (FIG. 6). The gain in mass observed in this study occurred over the course of the summer months when heat stress usually makes weight gain difficult.

Example 3

Clinical Response of Arthritic Horses to GHRH Plasmid Therapy

The purpose of this study was to provide data regarding the clinical response of arthritic horses to GHRH plasmid therapy followed by electroporation for horses with chronic laminitis/arthritic conditions.

This study was designed as a parallel and sequential controlled, randomized study utilizing 8 horses with chronic laminitis/arthritic conditions. In this study 4 horses were followed for a control period of at least 90 days before being subjected to GHRH/electroporation therapy. Animal were treated at day 0 with 2.5 mg pSP-wt-GHRH (pAV0225) (SEQID#26) FIG. 8, followed at 80 seconds by electroporation using the newly optimized electroporator device and needles described in U.S. patent application Ser. No. 10/657,725 filed on Sep. 8, 2003, titled "CONSTANT CURRENT ELECTROPORATION DEVICE AND METHODS OF USE," with Smith et al., listed as inventors, the entirty of which is hereby encorporated by reference. The electroporation device comprises an electro-kinetic device ("EKD") whose operation is specified by software or firmware. The EKD produces a series of programmable constant-current pulse patterns between electrodes in an array based on user control and input of the pulse parameters and allows the storage and acquisition of current waveform data. The electroporation device also comprises a replaceable electrode disk having an array of needle electrodes, a central injection channel for an injection needle, and a removable guide disk. The electroporator settings were 1 Amp-intensity of the electric field, 5 pulses, 52 milliseconds/pulse, 1 second interval between pulses. Needles were 21 gauge, 1 inch in length, and completed inserted into the muscle trough the intact skin. The plasmid was formulated in a 0.01% poly-L-glutamate solution, as described (Draghia-Akli et al., 2002b; Draghia-Akli and Smith, 2003). The injection was performed under light anesthesia to avoid involuntary movements of the animals. Following treatment subjects were followed 6 months with clinical evaluations being completed at 30 day intervals. An additional 4 horses with similar clinical disease served as non-treated controls. Evaluation parameters consisted of 1) radiographic evaluation, 2) physical lameness assessment, 3) quantitative force plate evaluation defining voluntary limb load and load distribution profile, 4) body condition score, 5) body mass, 6) a complete blood count, and 7) a standardized chemistry panel.

Subject Description: Experimental subjects used in this pilot study consisted of horses affected with chronic laminitis/arthritis and horses affected with traumatic induced chronic arthritis. The laminitis/arthritis subjects were naturally occurring chronic laminitis (at least 1 year in duration) patients that had developed arthritic symptoms either as a consequence of the laminitis or had a co-existing arthritic condition at the time the subject was first seen. Horses with arthritis without laminitis subjects with long-standing mild-to-severe degenerative joint disease associated with known trauma/athletic injury. Two subjects (one control and one treatment subject) also demonstrated a severe loss of body condition due to a combination of age and disease.

Results: GHRH treated laminitis/arthritic affected horses (n=2) both demonstrated a significant improvement in lameness status as detected by both physical and force plate assessment. By 6-months following treatment neither subject required systemic analgesics and were rated as pasture sound. Physical and radiographic evaluation of the feet demonstrated significant improvement and lameness associated with the arthritic condition was no longer evident.

Treated Subject 1 was lame at the initiation of the study. At radiological examination the subject presented with rotated bones than needed corrective shoes. Also, there was a vertical displacement of the cannon bone relative to hoof capsule. At the beginning of the study, Subject 1 was for one year on classical medication, receiving Phenylbutazone 4.4 mg/kg twice a day, Legend® (Bayer) as needed and thyroid hormones for stress-related hypothyroid condition. At 120 days after one GHRH-plasmid therapy, Subject 1 had discontinued all medication. The x-ray examination revealed that there was no more capsular rotation, side bones were in the right location, without signs of lameness. Subject 1 was capable of being riden again.

Treated Subject 2 was lame at the initiation of the study, with necrotic laminitis. At radiological examination the subject presented with capsular displacement of the cannon bone relative to hoof capsule, and a larger than normal joint space. At the beginning of the study, Subject 1 was for one year on classical medication, receiving Phenylbutazone 4.4 mg/kg twice a day. At 180 days after one GHRH-plasmid therapy, Subject 2 had discontinued medication. The x-ray examination revealed that there was no more capsular rotation, side bones were in the right location, without signs of lameness.

The ability to maintain an adequate body condition and body mass improved significantly following treatment. One of the laminitis/arthritis control horses (n=2) had to be euthanized due to increasing lameness and marked loss of body condition. The second control subject was still lame at the end of the study and demonstrates the difficulty in maintaining body condition typical of the chronically affected laminitis condition. The CBC and chemistry profiles of both groups remained in the normal range throughout the study.

GHRH treated non-laminitis arthritic subjects (n=2) demonstrated an initial improvement in arthritic status. Given the severity of the degenerative joint disease present in these horses at the initiation of the study both horses were still lame following the 6-month treatment period. One of the treated subjects had to be euthanized near the end of the treatment period due to collapse of the arthritic affected joint. Both horses demonstrated a marked improvement in body condition following treatment. One of the two non-treated control horses had to be euthanized early in this study due to the severity of pain associated with the arthritic condition and the second was demonstrated no improvement in either its arthritis or in the ability to maintain body condition.

There appeared to be an improvement in both the laminitis/arthritis affected horses. The arthritis in this class of patients is felt to be due either to chronic mal-positioning of the joints due to the digital disease or to systemic related changes that accompany the chronic laminitis syndrome. Current rehabilitation research in this area is focused on evaluation of the Legends® (Bayer) as therapeutic agent in this class of patients. The marked improvement of the laminar disease in these horses was surprising but not illogical as changes in epidermal growth factor receptors have been noted in the chronic disease.

The clinical response of the non-laminitic arthritic subjects is interpreted as be generally favorable. The treated subject that had to be euthanized near the end of the 6-month treatment period was felt to be due to the natural progression of the arthritic condition which was already severe at the initiation of the study. This subject demonstrated a significant improvement in body condition and attitude following treatment.

Similar to the previous study there was no data that supported or reflected a toxic or untoward effect of the GHRH/electroporation treatment.

Statistics. The data in the above examples were analyzed using SAS statistics analysis package. Values shown in the figures are the mean±s.d. Specific p values were obtained by analysis of variance with a Tukey post-hoc test. A $p<0.05$ was set as the level of statistical significance.

In contrast to injections with porcine recombinant somatotropin (rpST) or bST, which can produce unwanted side effects (e.g. hemorrhagic ulcers, vacuolations of liver and kidney or even death of the animals (Smith et al., 1991)), the plasmid mediated GHRH gene supplementation is well tolerated having no observed side effects in the animals. Regulated tissue/fiber-type-specific hGH-containing plasmids have been used previously for the delivery and stable production of GH in livestock and GH-deficient hosts. The methods used to deliver the hGH-containing plasmas comprise transgenesis, myoblast transfer or liposome-mediated intravenous injection (Barr and Leiden, 1991; Dahler et al., 1994; Pursel et al., 1990). Nevertheless, these techniques have significant disadvantages that preclude them from being used in a large-scale operation and/or on food animals, including: 1) possible toxicity or immune response associated with liposome delivery; 2) need for extensive ex vivo manipulation in the transfected myoblast approach; and/or 3) risk of important side effects or inefficiency in transgenesis (Dhawan et al., 1991; Miller et al., 1989). Compared to these techniques, plasmid mediated gene supplementation and DNA injection is simple and effective, with no complication related to the delivery system or to excess expression.

The embodiments provided herein illustrate that enhanced welfare of large mammals injected with a GHRH plasmid. Treated subjects display a significantly improvement in arthritis/lameness status and other conditions that result from their advanced disease. Treated subjects did not experience any side effects from the therapy, including associated pathology or death. Although not wanting to be bound by theory, the profound enhancement in animal welfare indicates that ectopic expression of myogenic GHRH vectors will likely replace classical GH therapy regimens and may stimulate the GH axis in a more physiologically appropriate manner.

One skilled in the art readily appreciates that this invention is well adapted to carry out the objectives and obtain the ends and advantages mentioned as well as those inherent therein. Growth hormone, growth hormone releasing hormone, analogs, plasmids, vectors, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

REFERENCES CITED

The entire content of each of the following U.S. patent documents and published references is hereby incorporated by reference.

U.S. PATENT DOCUMENTS

U.S. patent application Ser. No. 10/657,725 filed on Sep. 8, 2003, titled "CONSTANT CURRENT ELECTROPORATION DEVICE AND METHODS OF USE," with Smith et al., listed as inventors.
U.S. Pat. No. 5,847,066 issued on Dec. 8, 1998 with Coy et al. listed as inventors.
U.S. Pat. No. 5,846,936 issued on Dec. 8, 1998 with Felix et al. listed as inventors.
U.S. Pat. No. 5,792,747 issued on Aug. 11, 1998 with Schally et al. listed as inventors.
U.S. Pat. No. 5,776,901 issued on Jul. 7, 1998 with Bowers et al. listed as inventors.
U.S. Pat. No. 5,756,264 issued on May 26, 1998 with Schwartz et al. listed as inventors.
U.S. Pat. No. 5,696,089 issued on Dec. 9, 1997 with Felix et al. listed as inventors.
U.S. Pat. No. 5,486,505 issued on Jan. 23, 1996 with Bowers et al. listed as inventors.
U.S. Pat. No. 5,292,721 issued on Mar. 8, 1994 with Boyd et al. listed as inventors.
U.S. Pat. No. 5,137,872 issued on Aug. 11, 1992 with Seely et al. listed as inventors.
U.S. Pat. No. 5,134.210 issued on Jul. 28, 1992 with Boyd et al. listed as inventors.
U.S. Pat. No. 5,084,442 issued on Jan. 28, 1992 with Felix et al. listed as inventors.
U.S. Pat. No. 5,061,690 issued on Oct. 29, 1991 with Kann et al. listed as inventors.
U.S. Pat. No. 5,036,045 issued on Jul. 30, 1991 with Thorner listed as the inventor.
U.S. Pat. No. 5,023,322 issued on Jun. 11, 1991 with Kovacs et al. listed as inventors.
U.S. Pat. No. 4,839,344 issued on Jun. 13, 1989 with Bowers et al. listed as inventors.
U.S. Pat. No. 4,410,512 issued on Oct. 18, 1983 with Bowers et al. listed as inventors.
U.S. Pat. No. RE33,699 issued on Sep. 24, 1991 with Drengler listed as the inventor.
U.S. Pat. No. 4,833,166 issued on May 23, 1989 with Grosvenor et al. listed as inventors.
U.S. Pat. No. 4,228,158 issued on Oct. 14, 1980 with Momany et al. listed as inventors.
U.S. Pat. No. 4,228,156 issued on Oct. 14, 1980 with Momany et al. listed as inventors.
U.S. Pat. No. 4,226,857 issued on Oct. 7, 1980 with Momany et al. listed as inventors.
U.S. Pat. No. 4,224,316 issued on Sep. 23, 1980 with Momany et al. listed as inventors.
U.S. Pat. No. 4,223,021 issued on Sep. 16, 1980 with Momany et al. listed as inventors.
U.S. Pat. No. 4,223,020 issued on Sep. 16, 1980 with Momany et al. listed as inventors.
U.S. Pat. No. 4,223,019 issued on Sep. 16, 1980 with Momany et al. listed as inventors.
U.S. Pat. No. 5,702,359 titled "Needle electrodes for mediated delivery of drugs and genes," issued on Dec. 30, 1997, with Hofmann, et al., listed as inventors.
U.S. Pat. No. 5,439,440 titled "Electroporation system with voltage control feedback for clinical applications," issued on Aug. 8, 1995 with Hofmann listed as inventor.
PCT application WO/96/12520 titled "Electroporetic Gene and Drug Therapy by Induced Electric Fields," published on May 5, 1996 with Hofmann et al., listed as inventors.
PCT application WO/96/12006 titled "Flow Through Electroporation Apparatus and Method," published on Apr. 25, 1996 with Hofmann et al., listed as inventors.
PCT application WO/95/19805 titled "Electroporation and Iontophoresis Apparatus and Method For insertion of Drugs and genes inot Cells," published on Jul. 27, 1995 with Hofmann listed as inventor.
PCT application WO/97/07826 titled "In Vivo Electroporation of Cells," published on Mar. 6, 1997, with Nicolau et al., listed as inventors.

REFERENCE LIST

Acsadi, G., G. Dickson, D. R. Love, A. Jani, F. S. Walsh, A. Gurusinghe, Wolff, J A, and K. E. Davies. 1991. Human dystrophin expression in mdx mice after intramuscular injection of DNA constructs. Nature 352:815-818.
Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bemabeu. 1996. Cloning of the human platelet endothelial cell adhesion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucl. Acids Res. 20:4795-4801.

Argente, J., J. Pozo, and J. A. Chowen. 1996. The growth hormone axis: control and effects. Hormone Research 45 Suppl 1:9-11.

Babiuk, L. A., R. Pontarollo, S. Babiuk, B. Loehr, and van Drunen Littel-van den Hurk. 2003. Induction of immune responses by DNA vaccines in large animals. Vaccine 21:649-658.

Barr, E. and J. M. Leiden. 1991. Systemic delivery of recombinant proteins by genetically modified myoblasts. Science 254:1507-1509.

Bercu, B. B. and R. F. Walker. 1997. Growth Hormone Secretagogues In Children With Altered Growth. Acta Paediatrica 86:102-106.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Blethen, S. L. and A. C. Rundle. 1996. Slipped capital femoral epiphysis in children treated with growth hormone. A summary of the National Cooperative Growth Study experience. Horm. Res. 46:113-116.

Bohlen, P., F. Esch, P. Brazeau, N. Ling, and R. Guillemin. 1983. Isolation and characterization of the porcine hypothalamic growth hormone releasing factor. Biochem. Biophys. Res. Commun. 116:726-734.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Carbonelli, D. L., E. Corley, M. Seigelchifer, and J. Zorzopulos. 1999. A plasmid vector for isolation of strong promoters in Escherichia coli. FEMS Microbiol. Lett. 177:75-82.

Caroni, P. and C. Schneider. 1994. Signaling by insulin-like growth factors in paralyzed skeletal muscle: rapid induction of IGF1 expression in muscle fibers and prevention of interstitial cell proliferation by IGF-BP5 and IGF-BP4. J. Neurosci. 14:3378-3388.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U.S.A 94:3596-3601.

Chevalier, R. L., S. Goyal, A. Kim, A. Y. Chang, D. Landau, and D. LeRoith. 2000. Renal tubulointerstitial injury from ureteral obstruction in the neonatal rat is attenuated by IGF-1. Kidney Int. 57:882-890.

Chung, C. S., T. D. Etherton, and J. P. Wiggins. 1985. Stimulation of swine growth by porcine growth hormone. J. Anim Sci. 60:118-130.

Cocea, L. 1997. Duplication of a region in the multiple cloning site of a plasmid vector to enhance cloning-mediated addition of restriction sites to a DNA fragment. Biotechniques 23:814-816.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. J. Clin. Endocrinol. Metab. 76:134-138.

Dahler, A., R. P. Wade, G. E. Muscat, and M. J. Waters. 1994. Expression vectors encoding human growth hormone (hGH) controlled by human muscle-specific promoters: prospects for regulated production of hGH delivered by myoblast transfer or intravenous injection. Gene 145:305-310.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Davis, H. L., R. G. Whalen, and B. A. Demeneix. 1993. Direct gene transfer into skeletal muscle in vivo: factors affecting efficiency of transfer and stability of expression. Hum. Gene Ther. 4:151-159.

Dhawan, J., L. C. Pan, G. K. Pavlath, M. A. Travis, A. M. Lanctot, and H. M. Blau. 1991. Systemic delivery of human growth hormone by injection of genetically engineered myoblasts. Science 254:1509-1512.

Dialynas, E., H. Brown-Borg, and A. Bartke. 1999. Immune function in transgenic mice overexpressing growth hormone (GH) releasing hormone, GH or GH antagonist. Proc. Soc. Exp. Biol. Med. 221:178-183.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early MRNA in murine cytomegalovirus. Proc. Natl. Acad. Sci. U.S.A 82:8325-8329.

Draghia-Akli, R., K. M. Ellis, L. A. Hill, P. B. Malone, and M. L. Fiorotto. 2003. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone In Severely Debilitated Dogs With Cancer. Mol. Ther. 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technol. Cancer Res. Treat. 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Draghia-Akli, R. and L. C. Smith. 2003. Electrokinetic Enhancement of Plasmid Delivery In Vivo. In: N. S. Templeton and D. D. Lasic (Eds.) Gene Therapy—Therapeutic Mechanisms and Strategies. pp. 245-263. Marcel Dekker, Inc., New York.

Dubreuil, P., D. Petitclerc, G. Pelletier, P. Gaudreau, C. Farmer, Mowles, TF, and P. Brazeau. 1990. Effect of dose and frequency of administration of a potent analog of human growth hormone-releasing factor on hormone secretion and growth in pigs. J. Anim Sci. 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. J. Clin. Endocrinol. Metab. 75:1115-1120.

Erikstrup, C., L. M. Pedersen, L. Heickendorff, T. Ledet, and L. M. Rasmussen. 2001. Production of hyaluronan and chondroitin sulphate proteoglycans from human arterial smooth muscle—the effect of glucose, insulin, IGF-I or growth hormone. Eur. J Endocrinol. 145:193-198.

Esch, F. S., P. Bohlen, N. C. Ling, P. E. Brazeau, W. B. Wehrenberg, M. O. Thomer, M. J. Cronin, and R. Guillemin. 1982. Characterization of a 40 residue peptide from a human pancreatic tumor with growth hormone releasing activity. Biochem. Biophys. Res. Commun. 109: 152-158.

Etherton, T. D., J. P. Wiggins, C. S. Chung, C. M. Evock, J. F. Rebhun, and P. E. Walton. 1986. Stimulation of pig growth performance by porcine growth hormone and growth hormone-releasing factor. J. Anim Sci. 63:1389-1399.

Evans, W. S., M. L. Vance, D. L. Kaiser, R. P. Sellers, J. L. Borges, T. R. Downs, L. A. Frohman, J. Rivier, W. Vale, and M. O. Thomer. 1985. Effects of intravenous, subcutaneous, and intranasal administration of growth hormone (GH)-releasing hormone-40 on serum GH concentrations in normal men. J. Clin. Endocrinol. Metab. 61:846-850.

Farmer, C., D. Petitclerc, G. Pelletier, and P. Brazeau. 1992. Lactation performance of sows injected with growth hormone-releasing factor during gestation and(or) lactation. J. Anim Sci. 70:2636-2642.

Farmer, C., S. Robert, and J. J. Matte. 1996. Lactation performance of sows fed a bulky diet during gestation and receiving growth hormone-releasing factor during lactation. J. Anim. Sci. 74:1298-1306.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Frisbie, D. D., S. C. Ghivizzani, P. D. Robbins, C. H. Evans, and C. W. McIlwraith. 2002. Treatment of experimental equine osteoarthritis by in vivo delivery of the equine interleukin-1 receptor antagonist gene. Gene Ther. 9:12-20.

Frisbie, D. D. and C. W. McIlwraith. 2000. Evaluation of gene therapy as a treatment for equine traumatic arthritis and osteoarthritis. Clin. Orthop. S273-S287.

Frohman, L. A., T. R. Downs, E. P. Heimer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., J. L. Thominet, C. B. Webb, M. L. Vance, H. Uderman, J. Rivier, W. Vale, and M. O. Thomer. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Fubini, S. L., H. N. Erb, K. P. Freeman, and R. J. Todhunter. 1999. Prognostic factors affecting survival of 507 horses with joint disease: (1983 to 1990). Can. J Vet. Res. 63:253-260.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and. 1995. The insulin gene promoter. A simplified nomenclature. Diabetes 44:1002-1004.

Gopinath, R. and T. D. Etherton. 1989a. Effects of porcine growth hormone on glucose metabolism of pigs: I. Acute and chronic effects on plasma glucose and insulin status. J. Anim. Sci. 67:682-688.

Gopinath, R. and T. D. Etherton. 1989b. Effects of porcine growth hormone on glucose metabolism of pigs: II. Glucose tolerance, peripheral tissue insulin sensitivity and glucose kinetics. J. Anim Sci. 67:689-697.

Gouze, E., S. C. Ghivizzani, G. D. Palmer, J. N. Gouze, P. D. Robbins, and C. H. Evans. 2001. Gene therapy for rheumatoid arthritis. Expert. Opin. Biol. Ther. 1:971-978.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Horlick, R. A. and P. A. Benfield. 1989. The upstream muscle-specific enhancer of the rat muscle creatine kinase gene is composed of multiple elements. Mol. Cell. Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jardieu, P., R. Clark, D. Mortensen, and K. Dorshkind. 1994. In vivo administration of insulin-like growth factor-I stimulates primary B lymphopoiesis and enhances lymphocyte recovery after bone marrow transplantation. J Immunol. 152:4320-4327.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Khorram, O., M. Garthwaite, and T. Golos. 2001. The influence of aging and sex hormones on expression of growth hormone-releasing hormone in the human immune system. J Clin. Endocrinol. Metab 86:3157-3161.

Klamut, H. J., L. 0. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10:193-205.

Klindt, J., J. T. Yen, F. C. Buonomo, A. J. Roberts, and T. Wise. 1998. Growth, body composition, and endocrine responses to chronic administration of insulin-like growth factor I and(or) porcine growth hormone in pigs. J. Anim Sci. 76:2368-2381.

Koo, G. C., C. Huang, R. Camacho, C. Trainor, J. T. Blake, A. Sirotina-Meisher, K. D. Schleim, T. J. Wu, K. Cheng, R. Nargund, and G. McKissick. 2001. Immune enhancing effect of a growth hormone secretagogue. J Immunol. 166: 4195-4201.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lapierre, H., G. Pelletier, D. Petitclerc, P. Dubreuil, J. Morisset, P. Gaudreau, Y. Couture, and P. Brazeau. 1991. Effect of human growth hormone-releasing factor and(or) thyrotropin-releasing factor on growth, carcass composition, diet digestibility, nutrient balance, and plasma constituents in dairy calves. J. Anim. Sci. 69:587-598.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Ledwith, B. J., S. Manam, P. J. Troilo, A. B. Barnum, C. J. Pauley, T. G. Griffiths, L. B. Harper, C. M. Beare, W. J. Bagdon, and W. W. Nichols. 2000a. Plasmid DNA vaccines: investigation of integration into host cellular DNA following intramuscular injection in mice. Intervirology 43:258-272.

Ledwith, B. J., S. Manam, P. J. Troilo, A. B. Barnum, C. J. Pauley, T. G. Griffiths, L. B. Harper, H. B. Schock, H. Zhang, J. E. Faris, P. A. Way, C. M. Beare, W. J. Bagdon, and W. W. Nichols. 2000b. Plasmid DNA vaccines: assay for integration into host genomic DNA. Dev. Biol. (Basel) 104:33-43.:33-43.

Lee, S. H., W. Wang, S. Yajima, P. A. Jose, and M. M. Mouradian. 1997. Tissue-specific promoter usage in the DIA dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11: 1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, J. L. and D. LeRoith. 1999. Insulin-like growth factor I is essential for postnatal growth in response to growth hormone. Endocrinology 140:5178-5184.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macejak, D. G. and P. Sarnow. 1991. Internal initiation of translation mediated by the 5' leader of a cellular mRNA. Nature 353:90-94.

Malone, E. D. 2002. Managing chronic arthritis. Vet. Clin. North Am. Equine Pract. 18:411-437.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Mi, Z., S. C. Ghivizzani, E. R. Lechman, D. Jaffurs, J. C. Glorioso, C. H. Evans, and P. D. Robbins. 2000. Adenovirus-mediated gene transfer of insulin-like growth factor 1 stimulates proteoglycan synthesis in rabbit joints. Arthritis Rheum. 43:2563-2570.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Miller, K. F., D. J. Bolt, V. G. Pursel, R. E. Hammer, C. A. Pinkert, R. D. Palmiter, and R. L. Brinster. 1989. Expression of human or bovine growth hormone gene with a mouse metallothionein-1 promoter in transgenic swine alters the secretion of porcine growth hormone and insulin-like growth factor-I. J. Endocrinol. 120:481-488.

Moore, R. A. 2002. The hidden costs of arthritis treatment and the cost of new therapy—the burden of non-steroidal anti-inflammatory drug gastropathy. Rheumatology. (Oxford) 41 Supp 1:7-15; discussion 35-42.

Mukherjee, P., B. Wu, L. Mayton, S. H. Kim, P. D. Robbins, and P. H. Wooley. 2003. TNF receptor gene therapy results in suppression of IgG2a anticollagen antibody in collagen induced arthritis. Ann. Rheum. Dis. 62:707-714.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Murray, R. C., R. M. DeBowes, E. M. Gaughan, C. F. Zhu, and K. A. Athanasiou. 1998. The effects of intra-articular methylprednisolone and exercise on the mechanical properties of articular cartilage in the horse. Osteoarthritis. Cartilage. 6:106-114.

Murray, R. D. and S. M. Shalet. 2000. Growth hormone: current and future therapeutic applications. Expert. Opin. Pharmacother. 1:975-990.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. 0. Rogers, S. R. Fuhrmann, H. Liang, M. Oakley, A. Taye, B. K. Sim, and S. L. Hoffmnan. 2001. Codon optimization of gene fragments encoding Plasmodium falciparum merzoite proteins enhances DNA vaccine protein expression and immunogenicity in mice. Infect. Immun. 69:7250-7253.

Naughton, M. J. and S. A. Shumaker. 2003. The case for domains of function in quality of life assessment. Qual. Life Res. 12 Suppl 1:73-80.:73-80.

Neidel, J. 2001. Changes in systemic levels of insulin-like growth factors and their binding proteins in patients with rheumatoid arthritis. Clin. Exp. Rheumatol. 19:81-84.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pavasant, P., T. Shizari, and C. B. Underhill. 1996. Hyaluronan synthesis by epiphysial chondrocytes is regulated by growth hormone, insulin-like growth factor-1, parathyroid hormone and transforming growth factor-beta 1. Matrix Biol. 15:423-432.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic MRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U.S.A 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. J. Mol. Cell. Cardiology 26:1393-1401.

Pursel, V. G., D. J. Bolt, K. F. Miller, C. A. Pinkert, R. E. Hammer, R. D. Palmiter, and R. L. Brinster. 1990. Expression and performance in transgenic pigs. J. Reprod. Fertil. Suppl 40:235-45:235-245.

Rabinovsky, E. D., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Reginster, J. Y. 2002. The prevalence and burden of arthritis. Rheumatology. (Oxford) 41 Supp 1:3-6.:3-6.

Robbins, K., S. McCabe, T. Scheiner, J. Strasser, R. Clark, and P. Jardieu. 1994. Immunological effects of insulin-like growth factor-I—enhancement of immunoglobulin synthesis. Clin. Exp. Immunol. 95:337-342.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10: 187-192.

Skroch, P., C. Buchman, and M. Karin. 1993. Regulation of human and yeast metallothionein gene transcription by heavy metal ions. Prog. Clin. Biol. Res. 380:113-28.:113-128.

Smith, L. C. and J. L. Nordstrom. 2000. Advances in plasmid gene delivery and expression in skeletal muscle. Curr. Opin. Mol. Ther. 2:150-154.

Smith, V. G., A. D. Leman, W. J. Seaman, and F. VanRavenswaay. 1991. Pig weaning weight and changes in hematology and blood chemistry of sows injected with recombinant porcine somatotropin during lactation. J. Anim Sci. 69:3501-3510.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Steel, C. M., A. R. Hunt, P. L. Adams, I. D. Robertson, C. Chicken, J. V. Yovich, and J. A. Stick. 1999. Factors associated with prognosis for survival and athletic use in foals with septic arthritis: 93 cases (1987-1994). J Am. Vet. Med. Assoc. 215:973-977.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. J. Clin. Endocrinol. Metab. 59:846-849.

Thorner, M. O., M. L. Hartman, M. L. Vance, S. S. Pezzoli, and E. J. Ampleford. 1995. Neuroendocrine regulation of growth hormone secretion. Neurosci. Biobehav. Reviews 19:465-468.

Thorner, M. O., M. L. Vance, W. S. Evans, A. D. Rogol, J. Rivier, W. Vale, Blizzard, and RM. 1986. Clinical studies with GHRH in man. Hormone Research 24:91-98.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA injection in combination with electroporation: a novel method for vaccination of farmed ruminants. Scand. J Immunol. 57:229-238.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, P M, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2 (XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion. Circulation 94:3281-3290.

Tur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

van Rooij, E. M., B. L. Haagmans, H. L. Glansbeek, Y. E. de Visser, M. G. de Bruin, W. Boersma, and A. T. Bianchi. 2000. A DNA vaccine coding for glycoprotein B of pseudorabies virus induces cell-mediated immunity in pigs and reduces virus excretion early after infection. Vet. Immunol. Immunopathol. 74:121-136.

Vance, M. L. 1990. Growth-hormone-releasing hormone. Clinical Chemistry 36:415-420.

Vance, M. L., D. L. Kaiser, W. S. Evans, R. Furlanetto, W. Vale, J. Rivier, and M. O. Thorner. 1985. Pulsatile growth hormone secretion in normal man during a continuous 24-hour infusion of human growth hormone releasing factor (1-40). Evidence for intermittent somatostatin secretion. J. Clin. Invest. 75:1584-1590.

Veldhuis, J. D., A. Iranmanesh, and A. Weltman. 1997. Elements In The Pathophysiology Of Diminished Growth Hormone (GH) Secretion In Aging Humans. Endocrine 7:41-48.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two years of replacement therapy in adults with growth hormone deficiency. Clin. Endocrinol. (Oxf) 47:485-494.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

What is claimed is:

1. A method of alleviating symptoms of arthritis in a subject having arthritis comprising:

(i) delivering directly into a muscle tissue of the subject an effective amount of a nucleic acid expression construct in an amount in a range of about 0.1-5 mg and poly-L-glutamate, the construct comprising pig pAV0225 (SEQ ID NO: 26) encoding a growth-hormone-releasing-hormone ("GHRH") to alleviate a symptom of arthritis;

(ii) electroporating the muscle tissue wherein the step of electroporating comprises:

a. penetrating the muscle tissue in the subject with a plurality of needle electrodes, wherein the plurality of needle electrodes are arranged in a spaced relationship and the muscle tissue of the subject comprise muscle cells; and b. applying an electrical pulse to the plurality of needle electrodes, wherein the electrical pulse allow the nucleic acid expression construct to traverse a muscle cell membrane;

wherein the delivering step further comprises delivering between the plurality of needle electrodes;

wherein the subject comprises a horse; and wherein the symptoms of arthritis comprise lameness.

2. A method of alleviating symptoms of arthritis in a subject having arthritis comprising:

(i) delivering directly into a muscle tissue of the subject an effective amount of a nucleic acid expression construct in an amount in a range of about 0.1-5 mg, the construct comprising a nucleotide sequence that encodes a growth-hormone-releasing-hormone ("GHRH") consisting of an amino acid sequence of SEQ ID NO.: 2 to alleviate a symptom of arthritis;

(ii) electroporating the muscle tissue wherein the step of etectroporating comprises:

a. penetrating the muscle tissue in the subject with a plurality of needle electrodes, wherein the plurality of needle electrodes are arranged in a spaced relationship and the muscle tissue of the subject comprise muscle cells; and b. applying an electrical pulse to the plurality of needle electrodes, wherein the electrical pulse allow the nucleic acid expression construct to traverse a muscle cell membrane;

wherein the delivering step further comprises delivering between the plurality of needle electrodes;

and wherein the symptom of arthritis comprises lameness.

3. The method of claim 2, wherein the delivering step comprises delivering directly into a muscle tissue of the subject an effective amount of the nucleic acid expression construct and poly-L-glutamate.

\* \* \* \* \*

SEQUENCE LISTING

```
<160> NUMBER OF SEQ ID NOS: 40

<210> SEQ ID NO 1
<211> LENGTH: 40
<212> TYPE: PRT
<213> ORGANISM: artificial sequence
<220> FEATURE:
<223> OTHER INFORMATION: This is a HV-growth hormone releasing hormone
      ("GHRH") analog.

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
<213> ORGANISM: Artificial sequence
<220> FEATURE:
<223> OTHER INFORMATION: This is an amino acid sequence for Pig-GHRH

<400> SEQUENCE: 2

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 3
<211> LENGTH: 40
<212> TYPE: PRT
<213> ORGANISM: artificial sequence
<220> FEATURE:
<223> OTHER INFORMATION: This is an amino acid sequence for Bovine-GHRH

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is an amino acid sequence for Dog-GHRH

<400> SEQUENCE: 4

Tyr Ala Asp Ala Ile Phe Thr Asn Ser Tyr Arg Lys Val Leu Gly Gln
1               5                   10                  15
```

-continued

Leu Ser Ala Arg Lys Leu Leu Gln Asp Ile Met Ser Arg Gln Gln Gly
            20                  25                  30

Glu Arg Asn Arg Glu Gln Gly Ala
        35                  40

<210> SEQ ID NO 5
<211> LENGTH: 40
<212> TYPE: PRT
<213> ORGANISM: Artificial Sequence
<220> FEATURE:
<223> OTHER INFORMATION: This is an amino acid sequence for Cat-GHRH

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 6
<211> LENGTH: 40
<212> TYPE: PRT
<213> ORGANISM: artificial sequence
<220> FEATURE:
<223> OTHER INFORMATION: This is a TI- growth hormone releasing hormone
      ("GHRH") analog.

<400> SEQUENCE: 6

Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 7
<211> LENGTH: 40
<212> TYPE: PRT
<213> ORGANISM: artificial sequence
<220> FEATURE:
<223> OTHER INFORMATION: This is an amino acid sequence for Ovine-GHRH

<400> SEQUENCE: 7

Tyr Ala Asp Ala Ile Phe Thr Asn Ser Tyr Arg Lys Ile Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 8
<211> LENGTH: 43
<212> TYPE: PRT
<213> ORGANISM: artificial sequence
<220> FEATURE:
<223> OTHER INFORMATION: This is an amino acid sequence for Chicken-GHRH

<400> SEQUENCE: 8

His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys Arg Val Gly
            20                  25                  30

```
Ser Gly Leu Gly Asp Glu Ala Glu Pro Leu Ser
        35                  40

<210> SEQ ID NO 9
<211> LENGTH: 40
<212> TYPE: PRT
<213> ORGANISM: artificial sequence
<220> FEATURE:
<223> OTHER INFORMATION: This is an amino acid sequence for Horse GHRH.
<220> FEATURE:
<221> NAME/KEY: misc_feature
<222> LOCATION: (1)..(1)
<223> OTHER INFORMATION: "Xaa" can be any naturally occurring amino acid
<220> FEATURE:
<221> NAME/KEY: misc_feature
<222> LOCATION: (30)..(30)
<223> OTHER INFORMATION: "Xaa" can be any naturally occurring amino acid
<220> FEATURE:
<221> NAME/KEY: misc_feature
<222> LOCATION: (31)..(31)
<223> OTHER INFORMATION: "Xaa" can be any naturally occurring amino acid
<220> FEATURE:
<221> NAME/KEY: misc_feature
<222> LOCATION: (32)..(32)
<223> OTHER INFORMATION: "Xaa" can be any naturally occurring amino acid
<220> FEATURE:
<221> NAME/KEY: misc_feature
<222> LOCATION: (33)..(33)
<223> OTHER INFORMATION: "Xaa" can be any naturally occurring amino acid
<220> FEATURE:
<221> NAME/KEY: misc_feature
<222> LOCATION: (34)..(34)
<223> OTHER INFORMATION: "Xaa" can be any naturally occurring amino acid
<220> FEATURE:
<221> NAME/KEY: misc_feature
<222> LOCATION: (35)..(35)
<223> OTHER INFORMATION: "Xaa" can be any naturally occurring amino acid
<220> FEATURE:
<221> NAME/KEY: misc_feature
<222> LOCATION: (36)..(36)
<223> OTHER INFORMATION: "Xaa" can be any naturally occurring amino acid
<220> FEATURE:
<221> NAME/KEY: misc_feature
<222> LOCATION: (37)..(37)
<223> OTHER INFORMATION: "Xaa" can be any naturally occurring amino acid
<220> FEATURE:
<221> NAME/KEY: misc_feature
<222> LOCATION: (38)..(38)
<223> OTHER INFORMATION: "Xaa" can be any naturally occurring amino acid
<220> FEATURE:
<221> NAME/KEY: misc_feature
<222> LOCATION: (39)..(39)
<223> OTHER INFORMATION: "Xaa" can be any naturally occurring amino acid
<220> FEATURE:
<221> NAME/KEY: misc_feature
<222> LOCATION: (40)..(40)
<223> OTHER INFORMATION: "Xaa" can be any naturally occurring amino acid

<400> SEQUENCE: 9

Xaa Ala Asp Ala Ile Phe Thr Asn Asn Tyr Arg Lys Val Leu Gly Gln
1               5                   10                  15

Leu Ser Ala Arg Lys Ile Leu Gln Asp Ile Met Ser Arg Xaa Xaa Xaa
            20                  25                  30

Xaa Xaa Xaa Xaa Xaa Xaa Xaa Xaa
        35                  40

<210> SEQ ID NO 10
<211> LENGTH: 40
<212> TYPE: PRT
<213> ORGANISM: artificial sequence
<220> FEATURE:
<223> OTHER INFORMATION: This is an amino acid sequence for human
      (1-40)-GHRH
```

```
<400> SEQUENCE: 10

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala
        35                  40

<210> SEQ ID NO 11
<211> LENGTH: 40
<212> TYPE: PRT
<213> ORGANISM: artificial sequence
<220> FEATURE:
<223> OTHER INFORMATION: This is a TV-growth hormone releasing hormone
      ("GHRH") analog.

<400> SEQUENCE: 11

Tyr Val Asp Ala Ile Phe Thr Asn Ser Tyr Arg Lys Val Leu Ala Gln
 1               5                  10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 12
<211> LENGTH: 40
<212> TYPE: PRT
<213> ORGANISM: artificial sequence
<220> FEATURE:
<223> OTHER INFORMATION: This is a TA-growth hormone releasing hormone
      ("GHRH") analog.

<400> SEQUENCE: 12

Tyr Ala Asp Ala Ile Phe Thr Asn Ser Tyr Arg Lys Val Leu Ala Gln
 1               5                  10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 13
<211> LENGTH: 44
<212> TYPE: PRT
<213> ORGANISM: artificial sequence
<220> FEATURE:
<223> OTHER INFORMATION: This is a human (1-44) growth hormone releasing
      hormone ("GHRH").

<400> SEQUENCE: 13

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 14
<211> LENGTH: 40
<212> TYPE: PRT
<213> ORGANISM: artificial sequence
<220> FEATURE:
<223> OTHER INFORMATION: This is the artificial sequence for GHRH
      (1-40)OH.
<220> FEATURE:
```

```
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
<222> LOCATION: (28)..(28)
<223> OTHER INFORMATION: Xaa at position 28 may be serine or asparagine.
<220> FEATURE:
<221> NAME/KEY: MISC_FEATURE
<222> LOCATION: (34)..(34)
<223> OTHER INFORMATION: Xaa at position 34 may be arginine or serine.
<220> FEATURE:
<221> NAME/KEY: MISC_FEATURE
<222> LOCATION: (36)..(36)
<223> OTHER INFORMATION: Xaa at position 36 may be arginine or
      glutamine.
<220> FEATURE:
<221> NAME/KEY: MISC_FEATURE
<222> LOCATION: (38)..(38)
<223> OTHER INFORMATION: Xaa at position 38 may be arginine or glutamine

<400> SEQUENCE: 14

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Xaa Asn Xaa Glu Xaa Gly Ala
        35                  40

<210> SEQ ID NO 15
<211> LENGTH: 323
<212> TYPE: DNA
<213> ORGANISM: artificial sequence
<220> FEATURE:
<223> OTHER INFORMATION: This is a nucleic acid sequence of a eukaryotic
      promoter c5-12.

<400> SEQUENCE: 15
cggccgtccg ccctcggcac catcctcacg acacccaaat atggcgacgg gtgaggaatg      60
gtggggagtt atttttagag cggtgaggaa ggtgggcagg cagcaggtgt tggcgctcta    120
aaaataactc ccgggagtta tttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323

<210> SEQ ID NO 16
<211> LENGTH: 190
<212> TYPE: DNA
<213> ORGANISM: artificial sequence
<220> FEATURE:
<223> OTHER INFORMATION: Nucleic acid sequence of a human growth hormone
      poly A tail.

<400> SEQUENCE: 16
```

```
gggtggcatc cctgtgaccc ctccccagtg cctctcctgg ccctggaagt tgccactcca    60
gtgcccacca gccttgtcct aataaaatta agttgcatca ttttgtctga ctaggtgtcc   120
ttctataata ttatggggtg gagggggtg gtatggagca aggggcaagt tgggaagaca    180
acctgtaggg                                                          190

<210> SEQ ID NO 17
<211> LENGTH: 795
<212> TYPE: DNA
<213> ORGANISM: artificial sequence
<220> FEATURE:
<223> OTHER INFORMATION: Nucleic acid sequence for antibiotic resistance
      gene kanamycin.

<400> SEQUENCE: 17
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat gggcgaagt gccggggcag    300 gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac tcatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795

<210> SEQ ID NO 18
<211> LENGTH: 219
<212> TYPE: DNA
<213> ORGANISM: artificial sequence
<220> FEATURE:
<223> OTHER INFORMATION: Sequence for an analog porcine GHRH sequence.

<400> SEQUENCE: 18
atggtgctct gggtgttctt ctttgtgatc ctcaccctca gcaacagctc ccactgctcc    60
ccacctcccc ctttgaccct caggatgcgc ggcacgtag atgccatctt caccaacagc   120
taccggaagg tgctggccca gctgtccgcc cgcaagctgc tccaggacat cctgaacagg   180
cagcagggag agaggaacca agagcaagga cataatga                           219

<210> SEQ ID NO 19
<211> LENGTH: 246
<212> TYPE: DNA
<213> ORGANISM: artificial sequence
<220> FEATURE:
<223> OTHER INFORMATION: Sequence for an analog mouse GHRH sequence.

<400> SEQUENCE: 19
gccatggtgc tctgggtgct ctttgtgatc ctcatcctca ccagcggcag ccactgcagc    60
ctgcctccca gccctccctt caggatgcag aggcacgtgg acgccatctt caccaccaac   120
```

```
tacaggaagc tgctgagcca gctgtacgcc aggaaggtga tccaggacat catgaacaag    180
cagggcgaga ggatccagga gcagagggcc aggctgagct gataagcttg cgatgagttc    240
ttctaa                                                               246

<210> SEQ ID NO 20
<211> LENGTH: 234
<212> TYPE: DNA
<213> ORGANISM: artificial sequence
<220> FEATURE:
<223> OTHER INFORMATION: Sequence for an analog rat GHRH sequence.

<400> SEQUENCE: 20
gccatggccc tgtgggtgtt cttcgtgctg ctgaccctga ccagcggaag ccactgcagc    60
ctgcctccca gccctccctt cagggtgcgc cggcacgccg acgccatctt caccagcagc    120
tacaggagga tcctgggcca gctgtacgct aggaagctcc tgcacgagat catgaacagg    180
cagcagggcg agaggaacca ggagcagagg agcaggttca actgataagc ttgc          234

<210> SEQ ID NO 21
<211> LENGTH: 29
<212> TYPE: DNA
<213> ORGANISM: artificial sequence
<220> FEATURE:
<223> OTHER INFORMATION: Nucleic acid sequence of a prokaryotic PNEO
      promoter.

<400> SEQUENCE: 21
accttaccag agggcgcccc agctggcaa                                      29

<210> SEQ ID NO 22
<211> LENGTH: 3534
<212> TYPE: DNA
<213> ORGANISM: artificial sequence
<220> FEATURE:
<223> OTHER INFORMATION: Plasmid vector having an analog GHRH sequence.

<400> SEQUENCE: 22
gttgtaaaac gacggccagt gaattgtaat acgactcact atagggcgaa ttggagctcc    60
accgcggtgg cggccgtccg ccctcggcac catcctcacg acacccaaat atggcgacgg    120
gtgaggaatg gtggggagtt attttttagag cggtgaggaa ggtgggcagg cagcaggtgt   180
tggcgctcta aaataactc ccgggagtta tttttagagc ggaggaatgg tggacaccca    240
aatatggcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcaccct cagcaacagc tcccactgct ccccacctcc    540 cccctttgacc ctcaggatgc ggcggcacgt agatgccatc ttcaccaaca gctaccggaa    600
ggtgctggcc cagctgtccg cccgcaagct gctccaggac atcctgaaca gcagcaggg    660 agagaggaac caagagcaag gagcataatg actgcaggaa ttcgatatca agcttatcgg    720
ggtggcatcc ctgtgacccc tccccagtgc ctctcctggc cctggaagtt gccactccag    780
tgcccaccag ccttgtccta ataaaattaa gttgcatcat tttgtctgac taggtgtcct    840
tctataatat tatggggtgg aggggggtgg tatggagcaa gggggcaagtt gggaagacaa    900 cctgtagggc ctgcggggtc tattgggaac caagctggag tgcagtggca caatcttggc    960
tcactgcaat ctccgcctcc tgggttcaag cgattctcct gcctcagcct cccgagttgt   1020
```

```
tgggattcca ggcatgcatg accaggctca gctaattttt gttttttttgg tagagacggg    1080 gtttcaccat attggccagg ctggtctcca actcctaatc tcaggtgatc tacccacctt    1140
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga gggggggccc ggtaccagct    1380
tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagacacg    2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca gcgtatgca    2880 gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
```

| | |
|---|---:|
| actgttggga agggcgatcg gtgcgggcct cttcgctatt acgccagctg gcgaaagggg | 3480 |
| gatgtgctgc aaggcgatta agttgggtaa cgccagggtt ttcccagtca cgac | 3534 |

<210> SEQ ID NO 23
<211> LENGTH: 2722
<212> TYPE: DNA
<213> ORGANISM: artificial sequence
<220> FEATURE:
<223> OTHER INFORMATION: Plasmid vector having a codon optimized mouse
GHRH sequence

<400> SEQUENCE: 23

| | |
|---|---:|
| ccaccgcggt ggcggccgtc cgccctcggc accatcctca cgacacccaa atatggcgac | 60 |
| gggtgaggaa tggtggggag ttatttttag agcggtgagg aaggtgggca ggcagcaggt | 120 |
| gttggcgctc taaaaataac tcccgggagt tatttttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |
| ggcggcccac gagctacccg gaggagcggg aggcgccaag cggatcccaa ggcccaactc | 360 |
| cccgaaccac tcagggtcct gtggacagct caccttagctg ccatggtgct ctgggtgctc | 420 |
| tttgtgatcc tcatcctcac cagcggcagc cactgcagcc tgcctcccag ccctcccttc | 480 |
| aggatgcaga ggcacgtgga cgccatcttc accaccaact acaggaagct gctgagccag | 540 |
| ctgtacgcca ggaaggtgat ccaggacatc atgaacaagc agggcgagag gatccaggag | 600 |
| cagagggcca ggctgagctg ataagcttat cggggtggca tccctgtgac ccctccccag | 660 |
| tgcctctcct ggccctggaa gttgccactc cagtgcccac cagccttgtc ctaataaaat | 720 |
| taagttgcat cattttgtct gactaggtgt ccttctataa tattatgggg tggagggggg | 780 |
| tggtatggag caaggggcaa gttgggaaga caacctgtag ggctcgaggg ggggcccggt | 840 |
| accagctttt gttcccttta gtgagggtta atttcgagct tggtcttccg cttcctcgct | 900 |
| cactgactcg ctgcgctcgg tcgttcggct gcggcgagcg gtatcagctc actcaaaggc | 960 |
| ggtaatacgg ttatccacag aatcagggga taacgcagga agaacatgt gagcaaaagg | 1020 |
| ccagcaaaag gccaggaacc gtaaaaaggc cgcgttgctg gcgttttttcc ataggctccg | 1080 |
| cccccctgac gagcatcaca aaaatcgacg ctcaagtcag aggtggcgaa acccgacagg | 1140 |
| actataaaga taccaggcgt ttccccctgg aagctccctc gtgcgctctc ctgttccgac | 1200 |
| cctgccgctt accggatacc tgtccgcctt tctcccttcg ggaagcgtgg cgctttctca | 1260 |
| tagctcacgc tgtaggtatc tcagttcggt gtaggtcgtt cgctccaagc tgggctgtgt | 1320 |
| gcacgaaccc ccgttcagc ccgaccgctg cgccttatcc ggtaactatc gtcttgagtc | 1380 |
| caacccggta agacacgact tatcgccact ggcagcagcc actggtaaca ggattagcag | 1440 |
| agcgaggtat gtaggcggtg ctacagagtt cttgaagtgg tggcctaact acggctacac | 1500 |
| tagaagaaca gtatttggta tctgcgctct gctgaagcca gttaccttcg gaaaaagagt | 1560 |
| tggtagctct tgatccggca acaaaccac cgctggtagc ggtggttttt tgtttgcaa | 1620 |
| gcagcagatt acgcgcagaa aaaaaggatc tcaagaagat cctttgatct tttctacggg | 1680 |
| gtctgacgct cagctagcgc tcagaagaac tcgtcaagaa ggcgatagaa ggcgatgcgc | 1740 |
| tgcgaatcgg gagcggcgat accgtaaagc acgaggaagc ggtcagccca ttcgccgcca | 1800 |
| agctcttcag caatatcacg ggtagccaac gctatgtcct gatagcggtc cgccacaccc | 1860 |
| agccggccac agtcgatgaa tccagaaaag cggccatttt ccaccatgat attcggcaag | 1920 |

```
caggcatcgc catgagtcac gacgagatcc tcgccgtcgg gcatgcgcgc cttgagcctg    1980
gcgaacagtt cggctggcgc gagcccctga tgctcttcgt ccagatcatc ctgatcgaca    2040
agaccggctt ccatccgagt acgtgctcgc tcgatgcgat gtttcgcttg gtggtcgaat    2100
gggcaggtag ccgatcaag cgtatgcagc cgccgcattg catcagccat gatggatact    2160
ttctcggcag gagcaaggtg agatgacagg agatcctgcc ccggcacttc gcccaatagc    2220
agccagtccc ttcccgcttc agtgacaacg tcgagcacag ctgcgcaagg aacgccgtc     2280 gtggccagcc acgatagccg cgctgcctcg tcctgcagtt cattcagggc accggacagg    2340
tcggtcttga caaaaagaac cgggcgcccc tgcgctgaca gccggaacac ggcggcatca    2400
gagcagccga ttgtctgttg tgcccagtca tagccgaata gcctctccac ccaagcggcc    2460
ggagaacctg cgtgcaatcc atcttgttca atcatgcgaa acgatcctca tcctgtctct    2520
tgatcagatc ttgatcccct gcgccatcag atccttggcg gcaagaaagc catccagttt    2580
actttgcagg gcttcccaac cttaccagag ggcgccccag ctggcaattc cggttcgctt    2640
gctgtccata aaccgccca gtctagcaac tgttgggaag ggcgatcgtg taatacgact    2700
cactataggg cgaattggag ct                                            2722
```

<210> SEQ ID NO 24
<211> LENGTH: 2725
<212> TYPE: DNA
<213> ORGANISM: artificial sequence
<220> FEATURE:
<223> OTHER INFORMATION: Plasmid vector having a codon optimized rat
      GHRH sequence

<400> SEQUENCE: 24

```
ccaccgcggt ggcggccgtc cgccctcggc accatcctca cgacacccaa atatggcgac      60
gggtgaggaa tggtggggag ttattttttag agcggtgagg aaggtgggca ggcagcaggt    120
gttggcgctc taaaaataac tcccgggagt tattttttaga gcggaggaat ggtggacacc    180
caaatatggc gacggttcct caccccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggccct gtgggtgttc    420
ttcgtgctgc tgaccctgac cagcggaagc cactgcagcc tgcctcccag ccctcccttc    480
agggtgcgcc ggcacgccga cgccatcttc accagcagct acaggaggat cctgggccag    540
ctgtacgcta ggaagctcct gcacgagatc atgaacaggc agcagggcga gaggaaccag    600
gagcagagga gcaggttcaa ctgataagct tatcggggtg catccctgt gaccctcccc    660 cagtgcctct cctggccctg aagttgcca ctccagtgcc caccagcctt gtcctaataa    720
aattaagttg catcattttg tctgactagg tgtccttcta taatattatg ggtggaggg    780 gggtggtatg gagcaagggg caagttggga agacaacctg tagggctcga ggggggccc    840 ggtaccagct tttgttccct ttagtgaggg ttaatttcga gcttggtctt ccgcttcctc    900
gctcactgac tcgctgcgct cggtcgttcg gctgcggcga cggtatcag ctcactcaaa    960 ggcggtaata cggttatcca cagaatcagg ggataacgca ggaaagaaca tgtgagcaaa    1020
aggccagcaa aaggccagga accgtaaaaa ggccgcgttg ctggcgtttt tccataggct    1080
ccgcccccct gacgagcatc acaaaaatcg acgctcaagt cagaggtggc gaaacccgac    1140
aggactataa agataccagg cgtttccccc tggaagctcc ctcgtgcgct ctcctgttcc    1200
gaccctgccg cttaccggat acctgtccgc ctttctccct tcgggaagcg tggcgctttc    1260
```

```
tcatagctca cgctgtaggt atctcagttc ggtgtaggtc gttcgctcca agctgggctg   1320
tgtgcacgaa ccccccgttc agcccgaccg ctgcgcctta tccggtaact atcgtcttga   1380
gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt ttttgtttg    1620 caagcagcag attacgcgca gaaaaaaagg atctcaagaa gatcctttga tcttttctac   1680
ggggtctgac gctcagctag cgctcagaag aactcgtcaa gaaggcgata gaaggcgatg   1740
cgctgcgaat cgggagcggc gataccgtaa agcacgagga gcggtcagc ccattcgccg    1800 ccaagctctt cagcaatatc acgggtagcc aacgctatgt cctgatagcg gtccgccaca   1860
cccagccggc cacagtcgat gaatccagaa aagcggccat tttccaccat gatattcggc   1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc acccaagcg    2460 gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                         2725
```

<210> SEQ ID NO 25
<211> LENGTH: 2725
<212> TYPE: DNA
<213> ORGANISM: artificial sequence
<220> FEATURE:
<223> OTHER INFORMATION: This is the codon optimized HV-GHRH expression
      plasmid.

<400> SEQUENCE: 25

```
ccaccgcggt ggcggccgtc cgccctcggc accatcctca cgacacccaa atatggcgac    60
gggtgaggaa tggtggggag ttattttag agcggtgagg aaggtgggca ggcagcaggt    120
gttggcgctc taaaaataac tcccgggagt tattttaga gcggaggaat ggtggacacc    180
caaatatggc gacggttcct cacccgtcgc catatttggg tgtccgccct cggccggggc   240
cgcattcctg ggggccgggc ggtgctcccg cccgcctcga taaaaggctc cggggccggc   300
ggcggcccac gagctacccg gaggagcggg aggcgcaag cggatcccaa ggcccaactc    360
cccgaaccac tcagggtcct gtggacagct cacctagctg ccatggtgct ctgggtgttc   420
ttctttgtga tcctcaccct cagcaacagc tcccactgct ccccacctcc ccctttgacc   480
ctcaggatgc ggcggcacgt agatgccatc ttcaccaaca gctaccggaa ggtgctggcc   540
```

```
cagctgtccg cccgcaagct gctccaggac atcctgaaca ggcagcaggg agagaggaac    600
caagagcaag gagcataatg acatcaagct tatcggggtg catccctgt gaccctccc     660 cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga ggggggggcc    840
ggtaccagct tttgttccct ttagtgaggg ttaatttcga gcttggtctt ccgcttcctc    900
gctcactgac tcgctgcgct cggtcgttcg gctgcggcga gcggtatcag ctcactcaaa    960
ggcggtaata cggttatcca cagaatcagg ggataacgca ggaaagaaca tgtgagcaaa   1020
aggccagcaa aaggccagga accgtaaaaa ggccgcgttg ctggcgtttt tccataggct   1080
ccgcccccct gacgagcatc acaaaaatcg acgctcaagt cagaggtggc gaaacccgac   1140
aggactataa agataccagg cgtttccccc tggaagctcc ctcgtgcgct ctcctgttcc   1200
gaccctgccg cttaccggat acctgtccgc ctttctccct tcgggaagcg tggcgctttc   1260
tcatagctca cgctgtaggt atctcagttc ggtgtaggtc gttcgctcca agctgggctg   1320
tgtgcacgaa ccccccgttc agcccgaccg ctgcgcctta ccggtaact atcgtcttga    1380 gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt tttttgttta   1620
caagcagcag attacgcgca gaaaaaaagg atctcaagaa gatcctttga tcttttctac   1680
ggggtctgac gctcagctag cgctcagaag aactcgtcaa gaaggcgata gaaggcgatg   1740
cgctgcgaat cgggagcggc gataccgtaa agcacgagga agcggtcagc ccattcgccg   1800
ccaagctctt cagcaatatc acgggtagcc aacgctatgt cctgatacgc gtccgccaca   1860
cccagccggc cacagtcgat gaatccagaa aagcggccat tttccaccat gatattcggc   1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc cacccaagcg   2460
gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                         2725
```

<210> SEQ ID NO 26
<211> LENGTH: 2721
<212> TYPE: DNA
<213> ORGANISM: artificial sequence
<220> FEATURE:

<223> OTHER INFORMATION: This is the codon optimized pig-GHRH expression
plasmid.

<400> SEQUENCE: 26

```
ccaccgcggt ggcggccgtc cgccctcggc accatcctca cgacacccaa atatggcgac      60
gggtgaggaa tggtggggag ttattttag agcggtgagg aaggtgggca ggcagcaggt      120
gttggcgctc taaaataac tcccgggagt tattttaga gcggaggaat ggtggacacc      180
caaatatggc gacggttcct cacccgtcgc catatttggg tgtccgccct cggccggggc      240
cgcattcctg ggggcgggc ggtgctcccg cccgcctcga taaaaggctc cggggccggc      300
ggcggcccac gagctacccg gaggagcggg aggcgccaag cggatcccaa ggcccaactc      360
cccgaaccac tcagggtcct gtggacagct cacctagctg ccatggtgct ctgggtgttc      420
ttctttgtga tcctcaccct cagcaacagc tcccactgct ccccacctcc cccttttgacc     480
ctcaggatgc ggcggtatgc agatgccatc ttcaccaaca gctaccggaa ggtgctgggc      540
cagctgtccg cccgcaagct gctccaggac atcatgagca ggcagcaggg agagaggaac      600
caagagcaag gagcataatg aaagcttatc ggggtggcat ccctgtgacc cctccccagt      660
gcctctcctg gccctggaag ttgccactcc agtgcccacc agccttgtcc taataaaatt      720
aagttgcatc atttttgtctg actaggtgtc cttctataat attatggggt ggaggggggt      780
ggtatggagc aaggggcaag ttgggaagac aacctgtagg gctcgagggg gggcccggta      840
ccagcttttg ttccctttag tgagggttaa tttcgagctt ggtcttccgc ttcctcgctc      900
actgactcgc tgcgctcggt cgttcggctg cggcgagcgg tatcagctca ctcaaaggcg      960
gtaatacggt tatccacaga atcaggggat aacgcaggaa agaacatgtg agcaaaaggc     1020
cagcaaaagg ccaggaaccg taaaaaggcc gcgttgctgg cgttttttcca taggctccgc     1080
ccccctgacg agcatcacaa aaatcgacgc tcaagtcaga ggtggcgaaa cccgacagga     1140
ctataaagat accaggcgtt tcccctgga agctccctcg tgcgctctcc tgttccgacc     1200
ctgccgctta ccggatacct gtccgccttt ctcccttcgg gaagcgtggc gctttctcat     1260
agctcacgct gtaggtatct cagttcggtg taggtcgttc gctccaagct gggctgtgtg     1320
cacgaacccc ccgttcagcc cgaccgctgc gccttatccg gtaactatcg tcttgagtcc     1380
aacccggtaa gacacgactt atcgccactg gcagcagcca ctggtaacag gattagcaga     1440
gcgaggtatg taggcggtgc tacagagttc ttgaagtggt ggcctaacta cggctacact     1500
agaagaacag tatttggtat ctgcgctctg ctgaagccag ttaccttcgg aaaaagagtt     1560
ggtagctctt gatccggcaa acaaaccacc gctggtagcg gtggtttttt tgtttacaag     1620
cagcagatta cgcgcagaaa aaaggatct caagaagatc ctttgatctt ttctacgggg     1680
tctgacgctc agctagcgct cagaagaact cgtcaagaag gcgatagaag gcgatgcgct     1740
gcgaatcggg agcggcgata ccgtaaagca cgaggaagcg gtcagcccat tcgccgccaa     1800
gctcttcagc aatatcacgg gtagccaacg ctatgtcctg atagcggtcc gccacaccca     1860
gccggccaca gtcgatgaat ccagaaaagc ggccattttc caccatgata ttcggcaagc     1920
aggcatcgcc atgagtcacg acgagatcct cgccgtcggg catgcgcgcc ttgagcctgg     1980
cgaacagttc ggctggcgcg agccctgat gctcttcgtc cagatcatcc tgatcgacaa     2040
gaccggcttc catccgagta cgtgctcgct cgatgcgatg tttcgcttgg tggtcgaatg     2100
ggcaggtagc cggatcaagc gtatgcagcc gccgcattgc atcagccatg atggatactt     2160
tctcggcagg agcaaggtga gatgacagga gatcctgccc cggcacttcg cccaatagca     2220
gccagtccct tcccgcttca gtgacaacgt cgagcacagc tgcgcaagga acgcccgtcg     2280
```

```
tggccagcca cgatagccgc gctgcctcgt cctgcagttc attcaggca ccggacaggt    2340 cggtcttgac aaaaagaacc gggcgcccct gcgctgacag ccggaacacg gcggcatcag    2400
agcagccgat tgtctgttgt gcccagtcat agccgaatag cctctccacc caagcggccg    2460
gagaacctgc gtgcaatcca tcttgttcaa tcatgcgaaa cgatcctcat cctgtctctt    2520
gatcagatct tgatccctg cgccatcaga tccttggcgg caagaaagcc atccagttta    2580 cttttgcaggg cttcccaacc ttaccagagg gcgccccagc tggcaattcc ggttcgcttg    2640
ctgtccataa aaccgcccag tctagcaact gttgggaagg gcgatcgtgt aatacgactc    2700
actatagggc gaattggagc t    2721
```

<210> SEQ ID NO 27
<211> LENGTH: 2716
<212> TYPE: DNA
<213> ORGANISM: artificial sequence
<220> FEATURE:
<223> OTHER INFORMATION: This is the codon optimized dog-GHRH expression plasmid.

<400> SEQUENCE: 27

```
ccaccgcggt ggcggccgtc cgccctcggc accatcctca cgacacccaa atatggcgac      60
gggtgaggaa tggtggggag ttattttttag agcggtgagg aaggtgggca ggcagcaggt     120
gttggcgctc taaaaataac tcccgggagt tatttttaga gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct ctgggtgttc     420
ttcctggtga tcctcaccct cagcagtggt tcccactctt ccccgccatc cctgcccatc     480
agaatccctc ggtatgcaga cgccatcttc accaacagct accggaaggt gctgggccag     540
ctgtccgccc gcaagctcct scaggacatc atgagccggc agcagggaga gagaaaccgg     600
gagcaaggag catagtaagc ttatcggggt ggcatccctg tgaccctcc ccagtgcctc     660 tcctggccct ggaagttgcc actccagtgc ccaccagcct tgtcctaata aaattaagtt     720
gcatcatttt gtctgactag gtgtccttct ataatattat ggggtggagg gggtggtat     780 ggagcaaggg gcaagttggg aagacaacct gtagggctcg agggggggcc cggtaccagc     840
ttttgttccc tttagtgagg gttaatttcg agcttggtct tccgcttcct cgctcactga     900
ctcgctgcgc tcggtcgttc ggctgcggcg agcggtatca gctcactcaa aggcggtaat     960
acggttatcc acagaatcag gggataacgc aggaaagaac atgtgagcaa aaggccagca    1020
aaaggccagg aaccgtaaaa aggccgcgtt gctggcgttt ttccataggc tccgccccc    1080 tgacgagcat cacaaaaatc gacgctcaag tcagaggtgg cgaaacccga caggactata    1140
aagataccag gcgtttcccc ctggaagctc cctcgtgcgc tctcctgttc cgaccctgcc    1200
gcttaccgga tacctgtccg cctttctccc ttcgggaagc gtggcgcttt ctcatagctc    1260
acgctgtagg tatctcagtt cggtgtaggt cgttcgctcc aagctgggct gtgtgcacga    1320 acccccgtt cagcccgacc gctgcgcctt atccggtaac tatcgtcttg agtccaaccc    1380
ggtaagacac gacttatcgc cactggcagc agccactggt aacaggatta gcagagcgag    1440
gtatgtaggc ggtgctacag agttcttgaa gtggtggcct aactacggct acactagaag    1500
aacagtattt ggtatctgcg ctctgctgaa gccagttacc ttcggaaaaa gagttggtag    1560
```

```
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta aagcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga tactttctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga aagccatcca gtttactttg   2580
cagggcttcc aaccttacc agagggcgcc ccagctggca attccggttc gcttgctgtc   2640
cataaaaccg cccagtctag caactgttgg gaagggcgat cgtgtaatac gactcactat   2700
agggcgaatt ggagct                                                   2716

<210> SEQ ID NO 28
<211> LENGTH: 2716
<212> TYPE: DNA
<213> ORGANISM: artificial sequence
<220> FEATURE:
<223> OTHER INFORMATION: This is the codon optimized bovine-GHRH
      expression plasmid.

<400> SEQUENCE: 28
ccaccgcggt ggcggccgtc cgccctcggc accatcctca cgacacccaa atatggcgac     60
gggtgaggaa tggtggggag ttattttag agcggtgagg aaggtgggca ggcagcaggt    120
gttggcgctc taaaataac tcccgggagt tattttaga gcggaggaat ggtgacacc     180
caaatatggc gacggttcct caccgtcgc catatttggg tgtccgccct cggccggggc    240
cgcattcctg ggggcgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct gtgggtgttc    420
ttcctggtga ccctgacctt gagcagcggc tcccacggct ccctgccctc ccagcctctg    480
cgcatccctc gctacgccga cgccatcttc accaacagct accgcaaggt gctcggccag    540
ctcagcgccc gcaagctcct gcaggacatc atgaaccggc agcagggcga gcgcaaccag    600
gagcagggag cctgataagc ttatcggggt ggcatccctg tgacccctcc ccagtgcctc    660
tcctggccct ggaagttgcc actccagtgc ccaccagcct tgtcctaata aaattaagtt    720
gcatcatttt gtctgactag gtgtccttct ataatattat ggggtggagg gggtggtat    780
ggagcaaggg gcaagttggg aagacaacct gtagggctcg agggggggcc cggtaccagc    840
ttttgttccc tttagtgagg gttaatttcg agcttggtct tccgcttcct cgctcactga    900
```

```
ctcgctgcgc tcggtcgttc ggctgcggcg agcggtatca gctcactcaa aggcggtaat    960
acggttatcc acagaatcag gggataacgc aggaaagaac atgtgagcaa aaggccagca   1020
aaaggccagg aaccgtaaaa aggccgcgtt gctggcgttt ttccataggc tccgcccccc   1080
tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta aagcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga ctttctctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga aagccatcca gtttactttg   2580
cagggcttcc caaccttacc agagggcgcc ccagctggca attccggttc gcttgctgtc   2640
cataaaaccg cccagtctag caactgttgg aagggcgat cgtgtaatac gactcactat   2700
agggcgaatt ggagct                                                   2716
```

<210> SEQ ID NO 29
<211> LENGTH: 2716
<212> TYPE: DNA
<213> ORGANISM: artificial sequence
<220> FEATURE:
<223> OTHER INFORMATION: This is the codon optimized cat-GHRH expression
    plasmid.

<400> SEQUENCE: 29

```
ccaccgcggt ggcggccgtc cgccctcggc accatcctca cgacacccaa atatggcgac     60
gggtgaggaa tggtggggag ttattttag agcggtgagg aaggtgggca ggcagcaggt    120
gttggcgctc taaaaataac tcccgggagt tattttaga gcggaggaat ggtggacacc    180
```

```
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttcctggtga tcctcacccs ssacagtggc tcccactgct ccccgccatc cctgcccctc    480
agaatgcctc ggtatgcaga tgccatcttc accaacagct accggaaggt gctgggtcag    540
ctgtctgccc gcaagctact gcaggacatc atgagcagac agcagggaga gagaaaccag    600
gagcaaggag cataataagc ttatcggggt ggcatccctg tgaccctcc ccagtgcctc     660 tcctggccct ggaagttgcc actccagtgc ccaccagcct tgtcctaata aaattaagtt    720
gcatcatttt gtctgactag gtgtccttct ataatattat ggggtggagg ggggtggtat    780
ggagcaaggg gcaagttggg aagacaacct gtagggctcg agggggggcc cggtaccagc    840
ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca   1020
aaaggccagg aaccgtaaaa aggccgcgtt gctggcgttt ttccataggc tccgcccccc   1080
tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta aagcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga tactttctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga aagccatcca gtttactttg   2580
```

-continued

| | |
|---|---|
| cagggcttcc caaccttacc agagggcgcc ccagctggca attccggttc gcttgctgtc | 2640 |
| cataaaaccg cccagtctag caactgttgg gaagggcgat cgtgtaatac gactcactat | 2700 |
| agggcgaatt ggagct | 2716 |

<210> SEQ ID NO 30
<211> LENGTH: 2739
<212> TYPE: DNA
<213> ORGANISM: artificial sequence
<220> FEATURE:
<223> OTHER INFORMATION: This is the codon optimized TI-GHRH expression plasmid.

<400> SEQUENCE: 30

| | |
|---|---|
| ccaccgcggt ggcggccgtc cgccctcggc accatcctca cgacacccaa atatggcgac | 60 |
| gggtgaggaa tggtggggag ttattttag agcggtgagg aagtgggca ggcagcaggt | 120 |
| gttggcgctc taaaataac tcccgggagt tattttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |
| ggcggcccac gagctacccg gaggagcggg aggcgcaag cggatcccaa ggcccaactc | 360 |
| cccgaaccac tcagggtcct gtggacagct cacctagctg ccatggtgct ctgggtgttc | 420 |
| ttctttgtga tcctcaccct cagcaacagc tcccactgct ccccacctcc ccctttgacc | 480 |
| ctcaggatgc ggcggtatat cgatgccatc ttcaccaaca gctaccggaa ggtgctggcc | 540 |
| cagctgtccg cccgcaagct gctccaggac atcctgaaca gcagcaggg agagaggaac | 600 |
| caagagcaag gagcataatg actgcaggaa ttcgatatca agcttatcgg ggtggcatcc | 660 |
| ctgtgacccc tccccagtgc ctctcctggc cctggaagtt gccactccag tgcccaccag | 720 |
| ccttgtccta ataaaattaa gttgcatcat tttgtctgac taggtgtcct tctataatat | 780 |
| tatggggtgg aggggggtgg tatggagcaa ggggcaagtt gggaagacaa cctgtagggc | 840 |
| tcgaggggg gcccggtacc agcttttgtt ccctttagtg agggttaatt tcgagcttgg | 900 |
| tcttccgctt cctcgctcac tgactcgctg cgctcggtcg ttcggctgcg gcgagcggta | 960 |
| tcagctcact caaaggcggt aatacggtta tccacagaat caggggataa cgcaggaaag | 1020 |
| aacatgtgag caaaaggcca gcaaaaggcc aggaaccgta aaaaggccgc gttgctggcg | 1080 |
| ttttccata ggctccgccc ccctgacgag catcacaaaa atcgacgctc aagtcagagg | 1140 |
| tggcgaaacc cgacaggact ataaagatac caggcgtttc ccctggaag ctccctcgtg | 1200 |
| cgctctcctg ttccgaccct gccgcttacc ggatacctgt ccgcctttct cccttcggga | 1260 |
| agcgtggcgc tttctcatag ctcacgctgt aggtatctca gttcggtgta ggtcgttcgc | 1320 |
| tccaagctgg gctgtgtgca cgaaccccc gttcagcccg accgctgcgc cttatccggt | 1380 |
| aactatcgtc ttgagtccaa cccggtaaga cacgacttat cgccactggc agcagccact | 1440 |
| ggtaacagga ttagcagagc gaggtatgta ggcggtgcta cagagttctt gaagtggtgg | 1500 |
| cctaactacg gctacactag aagaacagta tttggtatct gcgctctgct gaagccagtt | 1560 |
| accttcggaa aaagagttgg tagctcttga tccggcaaac aaaccaccgc tggtagcggt | 1620 |
| ggtttttttg tttacaagca gcagattacg cgcagaaaaa aaggatctca agaagatcct | 1680 |
| ttgatctttt ctacggggtc tgacgctcag ctagcgctca gaagaactcg tcaagaaggc | 1740 |
| gatagaaggc gatgcgctgc gaatcgggag cggcgatacc gtaaagcacg aggaagcggt | 1800 |
| cagcccattc gccgccaagc tcttcagcaa tatcacgggt agccaacgct atgtcctgat | 1860 |
| agcggtccgc cacacccagc cggccacagt cgatgaatcc agaaaagcgg ccattttcca | 1920 |

```
ccatgatatt cggcaagcag gcatcgccat gagtcacgac gagatcctcg ccgtcgggca    1980
tgcgcgcctt gagcctggcg aacagttcgg ctggcgcgag ccctgatgc tcttcgtcca     2040 gatcatcctg atcgcaaga ccggcttcca tccgagtacg tgctcgctcg atgcgatgtt     2100
tcgcttggtg gtcgaatggg caggtagccg gatcaagcgt atgcagccgc cgcattgcat    2160
cagccatgat ggatactttc tcggcaggag caaggtgaga tgacaggaga tcctgccccg    2220
gcacttcgcc caatagcagc cagtcccttc ccgcttcagt gacaacgtcg agcacagctg    2280
cgcaaggaac gcccgtcgtg gccagccacg atagccgcgc tgcctcgtcc tgcagttcat    2340
tcagggcacc ggacaggtcg gtcttgacaa aaagaaccgg gcgcccctgc gctgacagcc    2400
ggaacacggc ggcatcagag cagccgattg tctgttgtgc ccagtcatag ccgaatagcc    2460
tctccaccca agcggccgga gaacctgcgt gcaatccatc ttgttcaatc atgcgaaacg    2520
atcctcatcc tgtctcttga tcagatcttg atcccctgcg ccatcagatc cttggcggca    2580
agaaagccat ccagtttact ttgcagggct tcccaacctt accagagggc gccccagctg    2640
gcaattccgg ttcgcttgct gtccataaaa ccgcccagtc tagcaactgt tgggaagggc    2700
gatcgtgtaa tacgactcac tatagggcga attggagct                           2739
```

<210> SEQ ID NO 31
<211> LENGTH: 2716
<212> TYPE: DNA
<213> ORGANISM: artificial sequence
<220> FEATURE:
<223> OTHER INFORMATION: This is the codon optimized ovine-GHRH
      expression plasmid.

<400> SEQUENCE: 31

```
ccaccgcggt ggcggccgtc cgccctcggc accatcctca cgacacccaa atatggcgac     60
gggtgaggaa tggtgggag ttatttttag agcggtgagg aaggtgggca ggcagcaggt     120
gttggcgctc taaaaataac tcccgggagt tattttaga gcggaggaat ggtggacacc     180
caaatatggc gacggttcct caccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct gtgggtgttc     420
ttcctggtga ccctgaccct gagcagcgga agccacggca gcctgcccag ccagcccctg     480
aggatccctc ggtacgccga cgccatcttc accaacagct acaggaagat cctgggccag     540
ctgagcgcta ggaagctcct gcaggacatc atgaacaggc agcagggcga gaggaaccag     600
gagcagggcg cctgataagc ttatcggggt ggcatccctg tgaccctcc ccagtgcctc     660 tcctggccct ggaagttgcc actccagtgc ccaccagcct tgtcctaata aaattaagtt    720
gcatcatttt gtctgactag gtgtccttct ataatattat ggggtggagg gggtggtat    780 ggagcaaggg gcaagttggg aagacaacct gtagggctcg aggggggggcc cggtaccagc    840 ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca    1020
aaaggccagg aaccgtaaaa aggccgcgtt gctggcgttt ttccataggc tccgccccc    1080 tgacgagcat cacaaaaatc gacgctcaag tcagaggtgg cgaaacccga caggactata    1140
aagataccag gcgtttcccc ctggaagctc cctcgtgcgc tctcctgttc cgaccctgcc    1200
```

-continued

| | |
|---|---|
| gcttaccgga tacctgtccg cctttctccc ttcgggaagc gtggcgcttt ctcatagctc | 1260 |
| acgctgtagg tatctcagtt cggtgtaggt cgttcgctcc aagctgggct gtgtgcacga | 1320 |
| acccccgtt cagcccgacc gctgcgcctt atccggtaac tatcgtcttg agtccaaccc | 1380 |
| ggtaagacac gacttatcgc cactggcagc agccactggt aacaggatta gcagagcgag | 1440 |
| gtatgtaggc ggtgctacag agttcttgaa gtggtggcct aactacggct acactagaag | 1500 |
| aacagtattt ggtatctgcg ctctgctgaa gccagttacc ttcggaaaaa gagttggtag | 1560 |
| ctcttgatcc ggcaaacaaa ccaccgctgg tagcggtggt ttttttgttt acaagcagca | 1620 |
| gattacgcgc agaaaaaaag gatctcaaga agatcctttg atcttttcta cggggtctga | 1680 |
| cgctcagcta gcgctcagaa gaactcgtca agaaggcgat agaaggcgat gcgctgcgaa | 1740 |
| tcgggagcgg cgataccgta aagcacgagg aagcggtcag cccattcgcc gccaagctct | 1800 |
| tcagcaatat cacgggtagc caacgctatg tcctgatagc ggtccgccac acccagccgg | 1860 |
| ccacagtcga tgaatccaga aaagcggcca ttttccacca tgatattcgg caagcaggca | 1920 |
| tcgccatgag tcacgacgag atcctcgccg tcgggcatgc gcgccttgag cctggcgaac | 1980 |
| agttcggctg gcgcgagccc ctgatgctct tcgtccagat catcctgatc gacaagaccg | 2040 |
| gcttccatcc gagtacgtgc tcgctcgatg cgatgtttcg cttggtggtc gaatgggcag | 2100 |
| gtagccggat caagcgtatg cagccgccgc attgcatcag ccatgatgga tactttctcg | 2160 |
| gcaggagcaa ggtgagatga caggagatcc tgccccggca cttcgcccaa tagcagccag | 2220 |
| tcccttcccg cttcagtgac aacgtcgagc acagctgcgc aaggaacgcc cgtcgtggcc | 2280 |
| agccacgata gccgcgctgc ctcgtcctgc agttcattca gggcaccgga caggtcggtc | 2340 |
| ttgacaaaaa gaaccgggcg cccctgcgct gacagccgga acacggcggc atcagagcag | 2400 |
| ccgattgtct gttgtgccca gtcatagccg aatagcctct ccacccaagc ggccggagaa | 2460 |
| cctgcgtgca atccatcttg ttcaatcatg cgaaacgatc ctcatcctgt ctcttgatca | 2520 |
| gatcttgatc ccctgcgcca tcagatcctt ggcggcaaga aagccatcca gtttactttg | 2580 |
| cagggcttcc caaccttacc agagggcgcc ccagctggca attccggttc gcttgctgtc | 2640 |
| cataaaaccg cccagtctag caactgttgg aagggcgat cgtgtaatac gactcactat | 2700 |
| agggcgaatt ggagct | 2716 |

<210> SEQ ID NO 32
<211> LENGTH: 2725
<212> TYPE: DNA
<213> ORGANISM: artificial sequence
<220> FEATURE:
<223> OTHER INFORMATION: This is the codon optimized chicken-GHRH expression plasmid.

<400> SEQUENCE: 32

| | |
|---|---|
| ccaccgcggt ggcggccgtc cgccctcggc accatcctca cgacacccaa atatggcgac | 60 |
| gggtgaggaa tggtggggag ttattttag agcggtgagg aaggtgggca ggcagcaggt | 120 |
| gttggcgctc taaaataac tcccgggagt tattttaga gcggaggaat ggtggacacc | 180 |
| caaatatggc gacggttcct cacccgtcgc catatttggg tgtccgccct cggccggggc | 240 |
| cgcattcctg ggggcggc ggtgctcccg cccgcctcga taaaggctc cggggccggc | 300 |
| ggcggcccac gagctacccg gaggagcggg aggcgcaag cggatcccaa ggcccaactc | 360 |
| cccgaaccac tcagggtcct gtggacagct cacctagctg ccatggccct gtgggtgttc | 420 |
| tttgtgctgc tgaccctgac ctccggaagc cactgcagcc tgccacccag ccacccttc | 480 |
| cgcgtcaggc gccacgccga cggcatcttc agcaaggcct accgcaagct cctgggccag | 540 |

```
ctgagcgcac gcaactacct gcacagcctg atggccaagc gcgtgggcag cggactggga    600
gacgaggccg agcccctgag ctgataagct tatcggggtg gcatccctgt gaccccctccc   660 cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga gggggggccc    840
ggtaccagct tttgttccct ttagtgaggg ttaatttcga gcttggtctt ccgcttcctc    900
gctcactgac tcgctgcgct cggtcgttcg gctgcggcga gcggtatcag ctcactcaaa    960
ggcggtaata cggttatcca cagaatcagg ggataacgca ggaaagaaca tgtgagcaaa   1020
aggccagcaa aaggccagga accgtaaaaa ggccgcgttg ctggcgtttt tccataggct   1080
ccgcccccct gacgagcatc acaaaaatcg acgctcaagt cagaggtggc gaaacccgac   1140
aggactataa agataccagg cgtttccccc tggaagctcc ctcgtgcgct ctcctgttcc   1200
gaccctgccg cttaccggat acctgtccgc ctttctccct cgggaagcg tggcgctttc    1260 tcatagctca cgctgtaggt atctcagttc ggtgtaggtc gttcgctcca agctgggctg   1320
tgtgcacgaa ccccccgttc agcccgaccg ctgcgcctta ccggtaact atcgtcttga    1380 gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt ttttgttta    1620 caagcagcag attacgcgca gaaaaaagg atctcaagaa gatcctttga tcttttctac    1680
ggggtctgac gctcagctag cgctcagaag aactcgtcaa gaaggcgata gaaggcgatg   1740
cgctgcgaat cgggagcggc gataccgtaa agcacgagga gcggtcagc ccattcgccg    1800 ccaagctctt cagcaatatc acgggtagcc aacgctatgt cctgatagcg gtccgccaca   1860
cccagccggc cacagtcgat gaatccagaa agcggccat tttccaccat gatattcggc    1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc acccaagcg    2460 gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                        2725
```

<210> SEQ ID NO 33
<211> LENGTH: 5
<212> TYPE: DNA
<213> ORGANISM: artificial sequence
<220> FEATURE:
<223> OTHER INFORMATION: This is the codon optimized Horse-GHRH
      expression plasmid.

<400> SEQUENCE: 33 aaaaa                                                                    5

<210> SEQ ID NO 34
<211> LENGTH: 225
<212> TYPE: DNA
<213> ORGANISM: artificial sequence
<220> FEATURE:
<223> OTHER INFORMATION: Sequence for an analog bovine GHRH sequence.

<400> SEQUENCE: 34
gccatggtgc tgtgggtgtt cttcctggtg accctgaccc tgagcagcgg ctcccacggc      60
tccctgccct cccagcctct cgcatccct cgctacgccg acgccatctt caccaacagc      120
taccgcaagg tgctcggcca gctcagcgcc cgcaagctcc tgcaggacat catgaaccgg      180
cagcagggcg agcgcaacca ggagcaggga gcctgataag cttgc                      225

<210> SEQ ID NO 35
<211> LENGTH: 225
<212> TYPE: DNA
<213> ORGANISM: artificial sequence
<220> FEATURE:
<223> OTHER INFORMATION: Sequence for an analog ovine GHRH sequence.

<400> SEQUENCE: 35
gccatggtgc tgtgggtgtt cttcctggtg accctgaccc tgagcagcgg aagccacggc      60
agcctgccca gccagcccct gaggatcccc aggtacgccg acgccatctt caccaacagc      120
tacaggaaga tcctgggcca gctgagcgct aggaagctcc tgcaggacat catgaacagg      180
cagcagggcg agaggaacca ggagcagggc gcctgataag cttgc                      225

<210> SEQ ID NO 36
<211> LENGTH: 246
<212> TYPE: DNA
<213> ORGANISM: artificial sequence
<220> FEATURE:
<223> OTHER INFORMATION: Sequence for an analog chicken GHRH sequence.

<400> SEQUENCE: 36
gccatggtgc tctgggtgct ctttgtgatc ctcatcctca ccagcggcag ccactgcagc      60
ctgcctccca gccctccctt caggatgcag aggcacgtgg acgccatctt caccaccaac      120
tacaggaagc tgctgagcca gctgtacgcc aggaaggtga tccaggacat catgaacaag      180
cagggcgaga ggatccagga gcagagggcc aggctgagct gataagcttg cgatgagttc      240
ttctaa                                                                  246

<210> SEQ ID NO 37
<211> LENGTH: 190
<212> TYPE: DNA
<213> ORGANISM: artificial sequence
<220> FEATURE:
<223> OTHER INFORMATION: Nucleic acid sequence of human growth hormone
      poly A tail.

<400> SEQUENCE: 37
gggtggcatc cctgtgaccc ctccccagtg cctctcctgg ccctggaagt tgccactcca      60
gtgcccacca gccttgtcct aataaaatta agttgcatca ttttgtctga ctaggtgtcc      120
ttctataata ttatggggtg gagggggtg gtatggagca aggggcaagt tgggaagaca      180

```
acctgtaggg                                                                      190

<210> SEQ ID NO 38
<211> LENGTH: 55
<212> TYPE: DNA
<213> ORGANISM: artificial sequence
<220> FEATURE:
<223> OTHER INFORMATION: Nucleic acid sequence of human growth hormone
      5' UTR

<400> SEQUENCE: 38
caaggcccaa ctccccgaac cactcagggt cctgtggaca gctcacctag ctgcc           55

<210> SEQ ID NO 39
<211> LENGTH: 782
<212> TYPE: DNA
<213> ORGANISM: artificial sequence
<220> FEATURE:
<223> OTHER INFORMATION: Nucleic acid sequence of a plasmid pUC-18
      origin of replicaiton

<400> SEQUENCE: 39
tcttccgctt cctcgctcac tgactcgctg cgctcggtcg ttcggctgcg gcgagcggta       60
tcagctcact caaaggcggt aatacggtta tccacagaat caggggataa cgcaggaaag      120
aacatgtgag caaaaggcca gcaaaaggcc aggaaccgta aaaaggccgc gttgctggcg      180
tttttccata ggctccgccc ccctgacgag catcacaaaa atcgacgctc aagtcagagg      240
tggcgaaacc cgacaggact ataaagatac caggcgtttc ccctggaag ctccctcgtg       300 cgctctcctg ttccgaccct gccgcttacc ggatacctgt ccgcctttct cccttcggga      360
agcgtggcgc tttctcatag ctcacgctgt aggtatctca gttcggtgta ggtcgttcgc      420
tccaagctgg gctgtgtgca cgaacccccc gttcagcccg accgctgcgc cttatccggt      480
aactatcgtc ttgagtccaa cccggtaaga cacgacttat cgccactggc agcagccact      540
ggtaacagga ttagcagagc gaggtatgta ggcggtgcta cagagttctt gaagtggtgg      600
cctaactacg gctacactag aaggacagta tttggtatct gcgctctgct gaagccagtt      660
accttcggaa aaagagttgg tagctcttga tccggcaaac aaaccaccgc tggtagcggt      720
ggtttttttg tttgcaagca gcagattacg cgcagaaaaa aaggatctca agaagatcct      780
tt                                                                    782

<210> SEQ ID NO 40
<211> LENGTH: 5
<212> TYPE: DNA
<213> ORGANISM: artificial sequence
<220> FEATURE:
<223> OTHER INFORMATION: This is a NEO ribosomal binding site

<400> SEQUENCE: 40 tcctc                                                                    5
```